US009512188B2

(12) United States Patent
Schaffer et al.

(10) Patent No.: US 9,512,188 B2
(45) Date of Patent: Dec. 6, 2016

(54) ISOLATED POLYNUCLEOTIDES AND METHODS AND PLANTS USING SAME FOR REGULATING PLANT ACIDITY

(75) Inventors: Arthur A. Schaffer, Hashmonaim (IL); Shahar Cohen, Rishon-LeZion (IL); Yosef Burger, Haifa (IL); Nurit Katzir, Kiryat-Tivon (IL)

(73) Assignee: The State of Israel, Ministry of Agriculture & Rural Development, Agricultural Research Organization (ARO) (Volcani Center), Rishon-LeZion (IL)

( * ) Notice: Subject to any disclaimer, the term of this patent is extended or adjusted under 35 U.S.C. 154(b) by 378 days.

(21) Appl. No.: 13/809,927

(22) PCT Filed: Jul. 12, 2011

(86) PCT No.: PCT/IL2011/000554
§ 371 (c)(1),
(2), (4) Date: Jan. 14, 2013

(87) PCT Pub. No.: WO2012/007945
PCT Pub. Date: Jan. 19, 2012

(65) Prior Publication Data
US 2013/0133106 A1 May 23, 2013

Related U.S. Application Data

(60) Provisional application No. 61/363,291, filed on Jul. 12, 2010.

(51) Int. Cl.
*C07K 14/415* (2006.01)
*C12N 15/82* (2006.01)
*C12Q 1/68* (2006.01)

(52) U.S. Cl.
CPC ......... *C07K 14/415* (2013.01); *C12N 15/8218* (2013.01); *C12N 15/8243* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 5,476,998 | A | 12/1995 | Kataoka et al. | |
|---|---|---|---|---|
| 5,534,660 | A * | 7/1996 | Chuck et al. | 800/282 |
| 6,803,500 | B1 | 10/2004 | Iida et al. | |
| 2009/0293144 | A1 | 11/2009 | Quattrocchio et al. | |

FOREIGN PATENT DOCUMENTS

| WO | WO 2009/013750 | | 1/2009 |
| WO | WO 2009/013750 A2 * | | 1/2009 |
| WO | WO 2012/007945 | | 1/2012 |

OTHER PUBLICATIONS

Tuskan G.A. et al., 2006, Science 313: 1596-1604.*
Tuskan G.A. et al., Database UNIPROT:B9IGX9, Database Accession No. B9IGX9, Mar. 24, 2009.*
Harel-Beja et al., 2010, Theor. Appl. Genet. 121: 511-533.*
Keskin et al., 2004, Protein Science 13: 1043-1055.*
Thornton et al., 2000, Nature Structural Biology, structural genomic supplement, Nov. 2000: 991-994.*
Guo et al., 2004, Proceedings of the National Academy of Sciences USA 101: 9205-9210.*
Obando-Ulloa et al., 2009, Scientia Horticulturae 121: 425-433.*
Cohen et al., 2014, Nature Communications doi: 10.1038/ncomms5026.*
Supplementary European Search Report and the European Search Opinion Dated Jan. 21, 2014 From the European Patent Office Re. Application No. 11806392.4.
Gonzalez-Ibeas et al. "*Cucumis melo* Subsp. *Melo* EST, Clone CI_67-G02-M13R", Database EMBL, [Online], XP002718147, Retrieved From EBI Accession No. EM_EST:AM735938, Database Accession No. AM735938, Sep. 25, 2007. Sequence.
Gonzalez-Ibeas et al. "MELOGEN: An EST Database for Melon Functional Genomics", BMC Genomics, XP021028119, 8(306): 1-17, Sep. 3, 2007. Sequence AM735938.
Tuskan et al. "SubName: Full=Auxin Efflux Carrier Component, Auxin Transport Protein", Database UniProt [Online], XP002718146, Retrieved From EBI Accession No. UNIPROT:B9IGX9, Database Accession No. B9IGX9, Mar. 24, 2009.
Tuskan et al. "The Genome of Black Cottonwood, *Populus trichocarpa* (Torr. & Gray)", Science, XP002591579, 313(5793): 1596-1604, Sep. 15, 2006.
International Preliminary Report on Patentability Dated Jan. 24, 2013 From the International Bureau of WIPO Re. Application No. PCT/IL2011/000554.
International Search Report and the Written Opinion Dated Feb. 21, 2012 From the International Searching Authority Re. Application No. PCT/IL2011/000554.
Invitation to Pay Additional Fees Dated Nov. 22, 2011 From the International Searching Authority Re. Application No. PCT/IL2011/000554.
Bohlmann "WS01910.B21_P02 PT-DX-N-A-10 Populus Trichocarpa cDNA Clone WS01910_P02 3-, mRNA Sequence", University of British Columbia, NCBI GenBank: FASTA, Accession No. CV228694, Sep. 21, 2004. Provided to as Additional Information Cited by Table 1 of WO 2009/013750 (Ronen et al.).
Boualem et al. "A Conserved Mutation in an Ethylene Biosynthesis Enzyme Leads to Andromonoecy in Melons", Science, 321: 836-838, Aug. 8, 2008. & Supporting Online Material.
Burger et al. "Development of Sweet Melon (*Cucumis melo*) Genotypes Combining High Sucrose and Organic Acid Content", Journal of the American Society of Horticultural Science, 128(4): 537-540, 2003.

(Continued)

*Primary Examiner* — Amjad Abraham
*Assistant Examiner* — Bratislav Stankovic

(57) ABSTRACT

Provided are isolated polynucleotides comprising a nucleic acid sequence encoding a polypeptide, wherein the polypeptide modulates acidity of a plant. Also provided are nucleic acid constructs and plant cells comprising same and methods of using same for modulating acidity of a plant.

6 Claims, 9 Drawing Sheets
(5 of 9 Drawing Sheet(s) Filed in Color)

(56) References Cited

OTHER PUBLICATIONS

Clavero "Control of Bacillus Coagulans and Clostridium Pasteurianum in Tomato Products", Acta Horticulturae, Proceedings of the 7th Symposium on Processing Tomato, 542: 75-81, 2001.

Danin-Poleg et al. "Construction of a Genetic Map of Melon With Molecular Markers and Horticultural Traits, and Localization of Genes Associated With ZYMV Resistance", Euphytica, 125: 373-384, 2002.

Ferrar et al. "Inhibition of Diphenol Oxidases: A Comparative Study", Journal of Food Biochemistry, 20: 15-30, 1996.

Harel-Beja et al. "A Genetic Map of Melon Highly Enriched With Fruit Quality QTLs and EST Markers, Including Sugar and Carotenoid Metabolism Genes", Theoretical and Applied Genetics, TAG, 121(3): 511-533, Apr. 17, 2010.

Haynes et al. "Effects of Soil Acidification on the Chemical Extractability of Fe, Mn, Zn and Cu and the Growth and Micronutrient Uptake of Highbush Blueberry Plants", Plant and Soil, 84: 201-212, 1985.

Henikoff et al. "TILLING. Traditional Mutagenesis Meets Functional Genomics", Plant Physiology, 135: 630-636, Jun. 2004.

Panda et al. "Aluminium Stress Signaling in Plants", Plant Signaling & Behavior, 4(7): 592-597, Jul. 2009.

Peters et al. "Forward Genetics and Map-Based Cloning Approaches", Trends in Plant Science, 8(10): 484-491, Oct. 2003.

Quattrocchio et al. "PH4 of Petunia Is an R2R3 MTB Protein That Activates Vacuolar Acidification Through Interactions With Basic-Helix-Loop-Helix Transcription Factors of the Anthocyanin Pathway", The Plant Cell, 18: 1274-1291, May 2006.

Rayle et al. "The Acid Growth Theory of Auxin-Induced Cell Elongation Is Alive and Well", Plant Physiology, 99: 1271-1274, 1992. p. 1271, col. 1, Para 1-2.

Silber et al. "Rhizosphere pH as a Result of Nitrogen Levels and NH4/NO3 Ration and Its Effect on Zinc Availability and on Growth of Rice Flower (*Ozothamnus diosmifolius*)", Plant and Soil, 262: 205-213, 2004.

Tabata et al. "Summaries. Sub-Name: Full=Putative Uncharacterized Protein T7H20_40", UNIPROT Direct Submission [Online], ID Q9LZN2_ARATH, Accession No. Q9LZN2, Oct. 1, 2000.

Tuskan et al. "Populus Trichocarpa Auxin Efflux Carrier Component, Auxin Transport Protein, mRNA", NCBI GenBank: FASTA [Online], Reference Sequence: XM_002323654.1, Accession No. XM_002323654, Dec. 4, 2009.

Walker et al. "Diphenol Oxidases, Enzyme-Catalysed Browning and Plant Disease Resistance", Biotechnology and Genetic Engineering Reviews, 15: 457-498, Apr. 1998.

Zeng et al. "The Influence of pH and Organic Matter Content in Paddy Soil on Heavy Metal Availability and Their Uptake by Rice Plants", Environmental Pollution, 159: 84-91, 2011.

Translation Dated Aug. 13, 2015 of Office Action Dated Jul. 22, 2015 From the Israel Patent Office Re. Application No. 224181.

Office Action Dated Apr. 5, 2016 From the Israel Patent Office Re. Application No. 224181 and Its Translation Into English.

\* cited by examiner

FIG. 1A

>sour melon
ATGGACATGG AAAGATTTCT CTCAGCCATC GTCTCGGAAG TTCAAGCGGG AGGGAACTCT
CTGCTTGTCA CTATTAAGAT TGCTGTGTTA CCCATAGCCA AAGTTTTCAC TATGTGCTTT
CTGGGTTTTC TTATGGCATC TAAATATGTC AACATCTTGC CTGCAAGTGG AAGGAAGCTT
TTGAATGGGT TGGTCTTTTC GCTTTTGCTT CCATGTTTAA TATTCTCTCA GCTCGGGCAA
GCTATTACTC TCGAGAAAAT GCTTAAATGG TGGTTTATTC CTGCAAACGT TGTTCTGGCT
TCGATATCAG GTTCCCTAAT TGGATTAATT GTGCATTAA TTGTTCGTCC TCCATACCCC
TTCTTCAAGT TCACAATTGT ACAAATTGGA ATTGGGAACA TTGGAAATGT GCCTCTCGTT
CTCATTGCAG CTCTATGTAG AGATGATATG AATCCTTTTG GTGATGAAGA GAAATGTAGC
ACTGATGGGA TTGCTTATAT TTCATATGGC CAGTGGGTTG GTGCAATTAT CCTGTACACC
TATGTTTATG CGATGCTGGC ACCTCCACCT GAGGGTACAT TTGACATCAA AGATCAAAAT
ATTCCAGTTA AGAATCTGCT AAAGGATAAT ACGCCTGCAC ATGTTCCCTT GCTCATTCAG
GAGGTAGCTT CAAAATATCC GGATGCTCCT AAGAAGGAAG AGACTAAGGG CTTCCTTATG
TATTGGTTTG ACAAATTGAA GCTCAAGCAA ATTTTCAGC CTCCTATCAT TGCTTCGGTC
CTAGCTATGT TATTGGGTGC AACTCCATTC TTAAGGCGAT TGATCTTTAC TCCTGATGCT
CCATTGTTTT TCTTCACTGA TAGCTGCATA ATGCTCGGGG AGGCTATGAT TCCATGTATC
CTGTTGGCAT TGGGAGGAAA CCTCGTTGAA GGTCCTGGAA GTTCAAAACT CGGGCTACGG
ACTACCGCTG CTGTTATTTT TGCAAGGTTG GTTTTGGTTC CTCCTGCAGG GGTTGGCATA
GTCATGTTAG CCGACAAGCT TGGCTTCCTT CCTCCAGATG ATAAAATGTT CCGATTCGTT
CTTCTTCTTC AGCATTCGAT GCCAACATCT GTCCTCTCGA GTGCTGTGGC TACTTTGAGG
GGTTGTGGTA GAGAATCTGC TGCTATTCTT TTCTGGGTTC ATATATTTGC CGTCATCTCA
ATGGCAGGGT GGTTCATCCT CTACTTCAGG ATACTCTTCT AA (SEQ ID NO:1)

FIG. 1B

> sour melon
MERFLSAIVS EVQAGGNSLL VTIKIAVLPI AKVFTMCFLG FLMASKYVNI LPASGRKLLN
GLVFSLLLPC LIFSQLGQAI TLEKMLKWWF IPANVVLASI SGSLIGLIVA LIVRPPYPFF
KFTIVQIGIG NIGNVPLVLI AALCRDDMNP FGDEEKCSTD GIAYISYGQW VGAIILYTYV
YAMLAPPPEG TFDIKDQNIP VKNLLKDNTP AHVPLLIQEV ASKYPDAPKK EETKGFLMYW
FDKLKLKQIF QPPIIASVLA MLLGATPFLR RLIFTPDAPL FFFTDSCIML GEAMIPCILL
ALGGNLVEGP GSSKLGLRTT AAVIFARLVL VPPAGVGIVM LADKLGFLPP DDKMFRFVLL
LQHSMPTSVL SSAVATLRGC GRESAAILFW VHIFAVISMA GWFILYFRIL F (SEQ ID
NO:2)

FIG. 1C
>non-sour melon
ATGGACATGG AAAGATTTCT CTCAGCCATC GTCTCGGAAG TTCAAGCGGG AGGGAACTCT
CTGCTTGTCA CTATTAAGAT TGCTGTGTTA CCCATAGCCA AAGTTTTCAC TATGTGCTTT
CTGGGTTTTC TTATGGCATC TAAATATGTC AACATCTTGC CTGCAAGTGG AAGGAAGCTT
TTGAATGGGT TGGTCTTTTC GCTTTTGCTT CCATGTTTAA TATTCTCTCA GCTCGGGCAA
GCTATTACTC TCGAGAAAAT GCTTAAATGG TGGTTTATTC CTGCAAACGT TGTTCTGGCT
TCGATATCAG GTTCCCTAAT TGGATTAATT GTTGCATTAA TTGTTGCATT AATTGTTCGT
CCTCCATACC CCTTCTTCAA GTTCACAATT GTACAAATTG GAATTGGGAA CATTGGAAAT
GTGCCTCTCG TTCTCATTGC AGCTCTATGT AGAGATGATA TGAATCCTTT TGGTGATGAA
GAGAAATGTA GCACTGATGG GATTGCTTAT ATTTCATATG CCAGTGGGT TGGTGCAATT
ATCCTGTACA CCTATGTTTA TGCGATGCTG GCACCTCCAC TGAGGGTAC ATTTGACATC
AAAGATCAAA ATATTCCAGT TAAGAATCTG CTAAAGGATA ATACGCCTGC ACATGTTCCC
TTGCTCATTC AGGAGGTAGC TTCAAAATAT CCGGATGCTC CTAAGAAGGA AGAGACTAAG
GGCTTCCTTA TGTATTGGTT TGACAAATTG AAGCTCAAGC AAATTTTTCA GCCTCCTATC
ATTGCTTCGG TCCTAGCTAT GTTATTGGGT GCAACTCCAT TCTTAAGGCG ATTGATCTTT
ACTCCTGATG CTCCATTGTT TTTCTTCACT GATAGCTGCA TAATGCTCGG GGAGGCTATG
ATTCCATGTA TCCTGTTGGC ATTGGGAGGA AACCTCGTTG AAGGTCCTGG AAGTTCAAAA
CTCGGGCTAC GGACTACCGC TGCTGTTATT TTTGCAAGGT TGGTTTTGGT TCCTCCTGCA
GGGGTTGGCA TAGTCATGTT AGCCGACAAG CTTGGCTTCC TTCCTCCAGA TGATAAAATG
TTCCGATTCG TTCTTCTTCT TCAGCATTCG ATGCCAACAT CTGTCCTCTC GAGTGCTGTG
GCTACTTTGA GGGGTTGTGG TAGAGAATCT GCTGCTATTC TTTTCTGGGT TCATATATTT
GCCGTCATCT CAATGGCAGG GTGGTTCATC CTCTACTTCA GGATACTCTT CTAA (SEQ ID
NO:3)

FIG. 1D
>non-sour Melon
MERFLSAIVS EVQAGGNSLL VTIKIAVLPI AKVFTMCFLG FLMASKYVNI LPASGRKLLN
GLVFSLLLPC LIFSQLGQAI TLEKMLKWWF IPANVVLASI SGSLIGLIVA LIVALIVRPP
YPFFKFTIVQ IGIGNIGNVP LVLIAALCRD DMNPFGDEEK CSTDGIAYIS YGQWVGAIIL
YTYVYAMLAP PPEGTFDIKD QNIPVKNLLK DNTPAHVPLL IQEVASKYPD APKKEETKGF
LMYWFDKLKL KQIFQPPIIA SVLAMLLGAT PFLRRLIFTP DAPLFFFTDS CIMLGEAMIP
CILLALGGNL VEGPGSSKLG LRTTAAVIFA RLVLVPPAGV GIVMLADKLG FLPPDDKMFR
FVLLLQHSMP TSVLSSAVAT LRGCGRESAA ILFWVHIFAV ISMAGWFILY FRILF (SEQ ID
NO:4)

FIG. 1E

```
Non-sour variety  MDMERFLSAIVSEVQAGGNSLLVTIKIAVLPIAKVFTMCFLGFLMASKYV   50
Sour variety      MDMERFLSAIVSEVQAGGNSLLVTIKIAVLPIAKVFTMCFLGFLMASKYV   50

Non-sour variety  NILPASGRKLLNGLVFSLLLPCLIFSQLGQAITLEKMLKWWFIPANVVLA  100
Sour variety      NILPASGRKLLNGLVFSLLLPCLIFSQLGQAITLEKMLKWWFIPANVVLA  100

Non-sour variety  SISGSLIGLIVALIVALIVRPPYPFFKFTIVQIGIGNIGNVPLVLIAALC  150
Sour variety      SISGSLIG....LIVALIVRPPYPFFKFTIVQIGIGNIGNVPLVLIAALC  146

Non-sour variety  RDDMNPFGDEEKCSTDGIAYISYGQWVGAIILYTYVYAMLAPPPEGTFDI  200
Sour variety      RDDMNPFGDEEKCSTDGIAYISYGQWVGAIILYTYVYAMLAPPPEGTFDI  196

Non-sour variety  KDQNIPVKNLLKDNTPAHVPLLIQEVASKYPDAPKKEETKGFLMYWFDKL  250
Sour variety      KDQNIPVKNLLKDNTPAHVPLLIQEVASKYPDAPKKEETKGFLMYWFDKL  246

Non-sour variety  KLKQIFQPPIIASVLAMLLGATPFLRRLIFTPDAPLFFFTDSCIMLGEAM  300
Sour variety      KLKQIFQPPIIASVLAMLLGATPFLRRLIFTPDAPLFFFTDSCIMLGEAM  296

Non-sour variety  IPCILLALGGNLVEGPGSSKLGLRTTAAVIFARLVLVPPAGVGIVMLADK  350
Sour variety      IPCILLALGGNLVEGPGSSKLGLRTTAAVIFARLVLVPPAGVGIVMLADK  346

Non-sour variety  LGFLPPDDKMFRFVLLQHSMPTSVLSSAVATLRGCGRESAAILFWVHIF  400
Sour variety      LGFLPPDDKMFRFVLLQHSMPTSVLSSAVATLRGCGRESAAILFWVHIF  396

Non-sour variety  AVISMAGWFILYFRILF (SEQ ID NO:4)                    417
Sour variety      AVISMAGWFILYFRILF (SEQ ID NO:2)
```

FIG. 2A
>Tomato TC200226
MDRVSRILFSVLTEPQRGGQSFITSIKIAVLPIAKVFTLCFLGFLMASKYVNILPANGRK
LLNGLVFSLLLPCLIFSQLGQAITYEKLLQWWFIPVNIVLATIFGSIIGLIVATIVRPPY
PYFKFTIIQIGIGNIGNVPLVLIAALCRDPSNPFGDSEICARDGNAYISFGQWVGAIILY
TFVFQMLSPPPEGSFDVEDANLPIKVPNKERLPSHPSGSSAEQVPLLATNVAPADSSSSN
KEKVKQFFKFLYETLKLKQLIQPPIIASIIAIIIGCVPVLKRLIFTSDAPLYFFTDSCLI
LGDAMIPCILLALGGNLVDGPGPGSSKIGLKFTVAIVFAPVVFGSSNWTQIVMLADKLGF
LPADDKMFRFVLLLQYSMPTSILAGAVANLRGCGKEAASILFWVHIFAVISMAGWIILYL
NILF (SEQ ID NO:5)

FIG. 2B
>Cucumber Csa01116
MENFLSAIVSEVQAGGNSLLVTIKIAVLPIAKVFTMCFLGFLMASKYVNILPASGRKLLNGLVFSLLLPCLIFSQLGQAI
TLEKMLKWWFIPANVVLASISGSLIGLIVASIVRPPYPFFKFTIVQIGIGNIGNVPLVLIAALCRDDMNPFGDEEKCSTD
GIAYISYGQWVGAIILYTYVYAMLAPPPEGTFDIKDQNISVKNLLKDNTPAHVPLLIQEVPSTYPDAPKKEEKYDMEYEK
CNNDNKTSTYFHNGIILSTLGIFPHSLTFGIFQKTKGFLIYWFDKLKLKQMFQPPIVASVLAMLLGATPFLRRLIFTPDA
PLFFFTDSCIMLGEAMIPCILLALGGNLVEGPGSSKLGLRTTAAIIFARLVLVPPAGLGIVMLADKLGFLPPDDKMFRFV
LLLQHSMPTSVLSSAVATLRGCGKDSAAILFWVHIFSVISMAGWFILYFRILF (SEQ ID NO:6)

FIG. 2C
>Sweet Melon
MERPLSAIVSEVQAGGNSLLVTIKIAVLPIAKVFTMCFLGFLMASKYVNILPASGRKLLNGLVFSLLLPCLIFSQLGQAI
TLEKMLKWWFIPANVVLASISGSLIGLIVALIVALIVRPPYPFFKFTIVQIGIGNIGNVPLVLIAALCRDDMNPFGDEEK
CSTDGIAYISYGQWVGAIILYTYVYAMLAPPPEGTFDIKDQNIPVKNLLKDNTPAHVPLLIQEVASKYPDAPKKEETKGF
LMYWFDKLKLKQIFQPPIIASVLAMLLGATPFLRRLIFTPDAPLFFFTDSCIMLGEAMIPCILLALGGNLVEGPGSSKLG
LRTTAAVIFARLVLVPPAGVGIVMLADKLGFLPPDDKMFRFVLLLQHSMPTSVLSSAVATLRGCGRESAAILFWVHIFAV
ISMAGWFILYFRILF (SEQ ID NO:4)

FIG. 2D
>apple TC80539
MERILAAVEVVNQAGGESLLGTIKIAVLPIAKVFTVCSLGLLMASKYVNIFPASGRKLLNGLVFSLLLPCLIFSQLGQAI
TLQKMLEWWFIPVNVVIGSTTGSIIGYIVASLVHPPYPFFKFTIVQIGIGNIGNVPLVLISALCRDKSNPFGDSTTCKTD
GTAYISFGQWVGAIILYTYVFQMLSPPPEGTFDVEEKELPIKSPRNGTTPDQVPLLTPDENEEETARKEEVAETESNASN
KPKITKFFLFIYEKLKLKQVLQPPIIASILAMVLGTIPFLKKLIFTSDGPLFFFTDSCIILGEAMIPCILLALGGNLVDG
PGSSKLGLRTTAAIIFARLVLVPPVGLGVVMLADKLGFLPPNDQMFRFVLLLQHTMPTSVLAGAVANLRGCGREAAAVLF
WVHIFAIFSMAGWIVLYLNILF (SEQ ID NO:8)

FIG. 2E
>Poplar EEF05451
MERPLLAVDTMGANQVGGGQTLLGTIKIAVLPIAKVFTMCFLGFLMASKYVNILPASGRKLLNGLVFSLLLPCLIFSQLG
QAVTLQKMLEWWFIPVNVVLSSICGSLIGFIVASIVRPPYPFFKFSIVQIGIGNIGNVPLVLIAALCRDTSNPFGDSEKC
STDGTAYISFGQWVGAIILYTYVFNMLAPPPEGTFDIDEPNLPIKKPAKDAPMEQVPLLAQEEAPAEPDAPKRGKIKQIL
VFLYDKLKLKQILQPPIIASILAMFLGAVPFLKQLIFTTDSPLFFFTDSCNILGEAMIPCILLALGGNLVDGPGSSKLGF
RTTAAIIFGRLVLVPPTGLGIVMLADKLGFLPAGDKMFRFVLLLQHTMPTSVLSGAVANLRGCGREAAAVLFWVHIFAIF
SMAGWIVLYLNILF (SEQ ID NO:9)

FIG. 2F
>Arabidopsis NP_195819
MIARILAALADSMEMPVAAGGGSVLGTIKIAVMPIAKVFTMCFLGLLMASKYVNILPPSGRKLLNGLVFSLLLPCLIFSQ
LGQAVTLQKMLQWWFIPVNVVLGTISGSIIGFIVASIVRPPYPYFKFTIIQIGVGNIGNVPLVLLAALCRDTSNPFGDSE
KCSIDGTAYISFGQWVGAIILYTYVYQMFAPPPEGFDAEEENLALKTLPVDAAPEQVPLLTQNFPKDFSPTQDLLPVQST
EPRGRGVSRKGKIAQIFVFLYEKLKLKQIVQPAIVASILAMILGAIPFTKKLIFTNGAPLFFFTDSCMILGDAMIPCILL
ALGGNLINGPGSSKLGFKTTAAIIIGRLVLVPPVGLGIVTVADKLGFLPADDKMFRFVLLLQHTMPTSVLSGAVANLRGC
GRESAAVLFWVHIFAIFSMAGWMVLYINILF (SEQ ID NO:10)

```
SourMelon    ---MERFLSAIVS----EVQAGGNSLLVTIKIAVLPIAKVFTMCFLGFLMASKYVNILPA  53
SweetMelon   ---MERFLSAIVS----EVQAGGNSLLVTIKIAVLPIAKVFTMCFLGFLMASKYVNILPA  53
Cucumber     ---MENFLSAIVS----EVQAGGNSLLVTIKIAVLPIAKVFTMCFLGFLMASKYVNILPA  53
Poplar       ---MERFLLAV-DTMGANQVGGCQTLLGTIKIAVLPIAKVFTMCFLGFLMASKYVNILPA  56
Arabidopsis  --MIARILAALADSMEMPVAAGGKSVLGTIKIAVMPIAKVFTMCFLGLLMASKYVNILPP  56
Apple        ---MERILAAV----EVVNQAGGESLLGTIKIAVLPIAKVFTVCSLGLLMASKYVNIFPA  53
Tomato       MDRVSRILFSVLT----EPQRGGQSFITSIKIAVLPIAKVPTLCFLGFLMASKYVNILPA  56
                  :.:* :*          *.* .: :*****.**:.:** **.********.*.

SourMelon    SGRKLLNGLVFSLLLPCLIFSQLGQAITLEKMLKWWNFIPANVVLASISGSLIG----LIV  109
SweetMelon   SGRKLLNGLVFSLLLPCLIFSQLGQAITLEKMLKWWNFIPANVVLASISGSLIG LIVA IV  113
Cucumber     SGRKLLNGLVFSLLLPCLIFSQLGQAITLEKMLKWWNFIPANVVLASISGSLIG----LIV  108
Poplar       SGRKLLNGLVFSLLLPCLIFSQLGQAVTLQKMLKWWNFIPVNVVLSSICGSLIG----FIV  112
Arabidopsis  SGRKLLNGLVFSLLLPCLIFSQLGQAVTLQKMLQWWNFIPVNVVLGTISGSIIG----FIV  114
Apple        SGRKLLNGLVFSLLLPCLIFSQLGQAITLQKMLKWWNFIPVNVVIGSSTGSIIG----YIV  109
Tomato       NGRKLLNGLVFSLLLPCLIFSQLGQAITYEKLLQWWNFIPVNIVLATIFGSIIG----LIV  112
             .************************ .*:.*:*:***** *:::.: **:*     :*

SourMelon    ALIVRPPYPFFKFTIVQIGIGNIGNVPLVLIAALCRDDMNPFGDEEKCSTDGIAYISYGQ  169
SweetMelon   ALIVRPPYPFFKFTIVQIGIGNIGNVPLVLIAALCRDDMNPFGDEEKCSTDGIAYISYGQ  173
Cucumber     ASIVRPPYPFFKFTIVQIGIGNIGNVPLVLIAALCRDDMNPFGDEEKCSTDGIAYISYGQ  168
Poplar       ASIVRPPYPFFKFSIVQIGIGNIGNVPLVLIAALCRDTGNPFGDSEKCSTDGTAYISEGQ  172
Arabidopsis  ASIVRPPYPYFKFTIIQIGVGNIGNVPLVLLAALCRDKSNPFGDSEKCSIDGTAYISEGQ  174
Apple        ASLVRPPYPFFKFTIVQIGIGNIGNVPLVLISALCRDKSNPFGDSTCKTDGTAYISEGQ  169
Tomato       ATIVRPPYPYPFKFTIIQIGIGNIGNVPLVLIAALCRDPSNPFGDSELCARDGNAYISPGQ  172
             *.:.*******:*:::::**:********:: **** .. ****.   ***:*** **

SourMelon    WVGAIILYTYVYAMLAPPPEGTFDIKDQNIPVKNLLKD----------NTPAHVPLLIQEVA  221
SweetMelon   WVGAIILYTYVYAMLAPPPEGTFDIKDQNIPVKNLLKD----------NTPAHVPLLIQEVA  225
Cucumber     WVGAIILYTYVYAMLAPPPEGTFDIKDQNIPVKNLLKD----------NTPAHVPLLIQEVP  221
Poplar       WVGAIILYTYVFNMLAPPPEGTFDIDEPNLPIKKPAKD----------APMEQVPLLAQ---  221
Arabidopsis  WVGAIILYTYVYQMFAPPPEG-FDAEENLALKTLPVD-----------AAPEQVPLLTQNFP  223
Apple        WVGAIILYTYVFQMLSPPPEGTFDVERELPIKSPRNG-----------TTPDQVPLITPD--  218
Tomato       WVGAIILYTFVFQMLSPPPEGSFDVEDANLPIKVPNKERLPSHPSGSSAEQVPLLATNVA  232
             ********:.:*::*:****.**.  :*. *. .                 :.****.

SourMelon    ---SKYPDAPKKEE------------------------------------TKGF  236
SweetMelon   ---SKYPDAPKKEE------------------------------------TKGF  240
Cucumber     ---STYPDAPKKEEKYDMEYEKCNNDNKTSTYFHNGIILSTLGIFPHSLTFGITQKTKGF  278
Poplar       ----EEAPAEP------------------------------DAPK-------RGKIKQI  239
Arabidopsis  KDFSPTQDLLPVQS----------------------------------TEPRGRGVSRKGKIAQI  256
Apple        ---ENEEETARKEE----------------------------------VAETESNASNKPKITKF  247
Tomato       ----PADSSSSNKE--------------------------------------KVKQF  247
                   :                                               :

SourMelon    LMYWFDKLKLKQIFQPPIIASVLAMLLGATPFLRRLIFTPDAPLFFFTDSCIMLGEAMIP  296
SweetMelon   LMYWFDKLKLKQIFQPPIIASVLAMLLGATPFLRRLIFTPDAPLFFFTDSCIMLGEAMIP  300
Cucumber     LIYWFDKLKLKQMFQPPIVASVLAMLLGATPFLRRLIFTPDAPLFFFTDSCIMLGEAMIP  338
Poplar       LVELYDKLKLKQILQPPIIASILAMFLGAVPFLKQLIFTTDSPLFFFTDSCNILGEAMIP  299
Arabidopsis  FVELYEKLKLKQIVQPAIVASILAMILGAIPFTKKLIFTNGAPLFFFTDSCMILGDAMIP  316
Apple        FLETYEKLKLKQVLQPPIIASILAMVLGTIPFLKKLIFTSDGPLFFFTDSCILGEAMIP  307
Tomato       FKFPLYETLKLKQLIQPPIIASIIAIIIGVPVLKRLIFTSGDAPLYFFTDSCLILGDAMIP  307
             : : :::*****: :*.*:**::*::.*. .:*: ****  :**:*******  :**:****

SourMelon    CILLALGGNLVEGPG--SSKLGLRTTAAVIFARLVLVPPAGVGIVMLADKLGFLPPDDKM  354
SweetMelon   CILLALGGNLVEGPG--SSKLGLRTTAAVIFARLVLVPPAGVGIVMLADKLGFLPPDDKM  356
Cucumber     CILLALGGNLVEGPG--SSKLGLRTTAAIIFARLVLVPPAGLGIVMLADKLGFLPPDDKM  396
Poplar       CILLALGGNLVDGPG--SSKLGFRTTAAIIFGRLVLVPPRGLGIVMLADKLGFLPAGDKM  357
Arabidopsis  CILLALGGNLINGPG--SSKLGFKTTAAIIIGRLVLVPPVGLGIVTVADKLGFLPADDKM  374
Apple        CILLALGGNLVDGPG--SSKLGLRTTAAIIFARLVLVPPVGLGIVMLADKLGFLPPNDQM  365
Tomato       CILLALGGNLVDGPGPGSSKIGLKTTVAIVFAPVWFGSSNMTQIVMLADKLGFLPADDKM  367
             ***********::**  ***:*::**.*::. :::. *.     *: **********:.**

SourMelon    FREVLLLQHSMPTSVLSSAVATLRGCGRESAAILFWVHIFAVISMAGWNFILYFRILE  411  (SEQ ID NO:2)
SweetMelon   FREVLLLQHSMPTSVLSSAVANLRGCGRESAAILFWVHIFAVISMAGWNFILYFRILE  415  (SEQ ID NO:4)
Cucumber     FREVLLLQHSMPTSVLSSAVATLRGCGKDSAAILFWVHIFSVIMAGWNFILYFRILE  453  (SEQ ID NO:6)
Poplar       FREVLLLQHTMPTSVLSGAVANLRGCGREAAAVLFWVHIPAIFSMAGWIVLYINILF  414  (SEQ ID NO:8)
Arabidopsis  FREVLLLQHTMPTSVLSAGAVANLRGCGREAAAVLFWVHIFAIFSMAGWMVLYINILF  431  (SEQ ID NO:10)
Apple        FREVLLLQHTMPTSVLAGAVANLRGCGREAAAVLFWVHIFAIFSMAGWMVLYINILF  422  (SEQ ID NO:8)
Tomato       FREVLLLQYSMPTSILAGAVANLRGCGREAASILFWVHIFAVISMAGWIILYINILF  424  (SEQ ID NO:5)
             ********:.****::*..**.*****::**::*****:.*:::*****: :**:**.**
```

FIG. 3

Protein of sour melon
```
# Sequence Length: 411
# Sequence Number of predicted TMHs:  10
# Sequence Exp number of AAs in TMHs: 206.37398
# Sequence Exp number, first 60 AAs:   25.36188
# Sequence Total prob of N-in:         0.63207
# Sequence POSSIBLE N-term signal sequence
Sequence      TMHMM2.0    inside      1     20
Sequence      TMHMM2.0    TMhelix     21    43
Sequence      TMHMM2.0    outside     44    57
Sequence      TMHMM2.0    TMhelix     58    77
Sequence      TMHMM2.0    inside      78    89
Sequence      TMHMM2.0    TMhelix     90    112
Sequence      TMHMM2.0    outside     113   121
Sequence      TMHMM2.0    TMhelix     122   144
Sequence      TMHMM2.0    inside      145   162
Sequence      TMHMM2.0    TMhelix     163   185
Sequence      TMHMM2.0    outside     186   251
Sequence      TMHMM2.0    TMhelix     252   274
Sequence      TMHMM2.0    inside      275   280
Sequence      TMHMM2.0    TMhelix     281   303
Sequence      TMHMM2.0    outside     304   322
Sequence      TMHMM2.0    TMhelix     323   342
Sequence      TMHMM2.0    inside      343   354
Sequence      TMHMM2.0    TMhelix     355   377
Sequence      TMHMM2.0    outside     378   386
Sequence      TMHMM2.0    TMhelix     387   409
Sequence      TMHMM2.0    inside      410   411
```

FIG. 4A

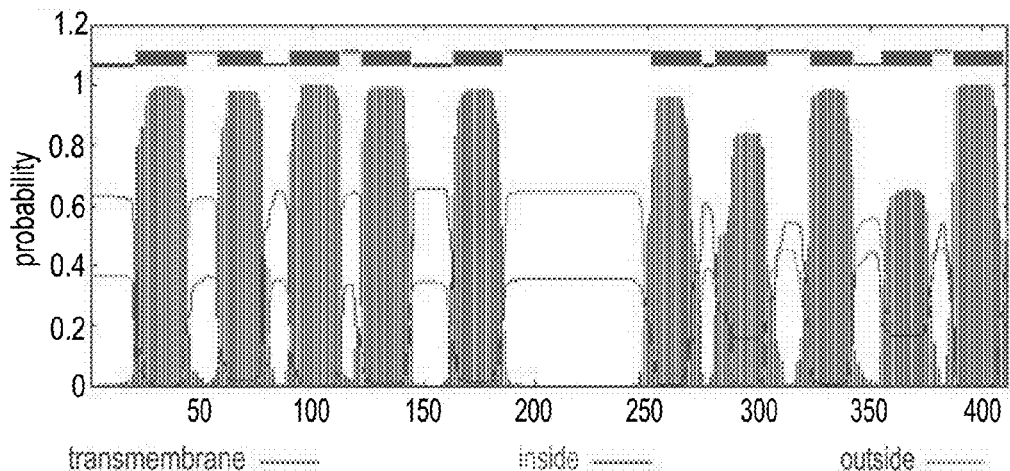

FIG. 4B

Protein of Non-sour melon
```
# Sequence Length: 415
# Sequence Number of predicted TMHs:  9
# Sequence Exp number of AAs in TMHs: 209.1751
# Sequence Exp number, first 60 AAs:   24.97444
# Sequence Total prob of N-in:          0.29853
# Sequence POSSIBLE N-term signal sequence
Sequence        TMHMM2.0        outside      1    19
Sequence        TMHMM2.0        TMhelix     20    42
Sequence        TMHMM2.0        inside      43    57
Sequence        TMHMM2.0        TMhelix     58    80
Sequence        TMHMM2.0        outside     81    94
Sequence        TMHMM2.0        TMhelix     95   117
Sequence        TMHMM2.0        inside     118   123
Sequence        TMHMM2.0        TMhelix    124   146
Sequence        TMHMM2.0        outside    147   165
Sequence        TMHMM2.0        TMhelix    166   188
Sequence        TMHMM2.0        inside     189   257
Sequence        TMHMM2.0        TMhelix    258   277
Sequence        TMHMM2.0        outside    278   291
Sequence        TMHMM2.0        TMhelix    292   311
Sequence        TMHMM2.0        inside     312   323
Sequence        TMHMM2.0        TMhelix    324   346
Sequence        TMHMM2.0        outside    347   388
Sequence        TMHMM2.0        TMhelix    389   411
Sequence        TMHMM2.0        inside     412   415
```
FIG. 4C

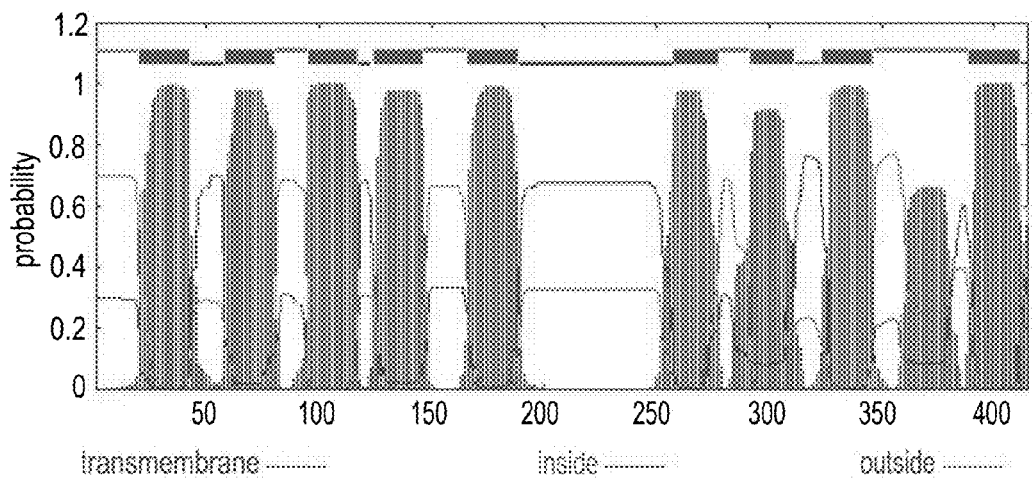

FIG. 4D

SEQUENCE LISTING

```
<160> NUMBER OF SEQ ID NOS: 42

<210> SEQ ID NO 1
<211> LENGTH: 1242
<212> TYPE: DNA
<213> ORGANISM: Cucumis melo

<400> SEQUENCE: 1
atggacatgg aaagatttct ctcagccatc gtctcggaag ttcaagcggg agggaactct      60
ctgcttgtca ctattaagat tgctgtgtta cccatagcca aagttttcac tatgtgcttt     120
ctgggttttc ttatggcatc taaatatgtc aacatcttgc ctgcaagtgg aaggaagctt     180
ttgaatgggt tggtcttttc gcttttgctt ccatgtttaa tattctctca gctcgggcaa     240
gctattactc tcgagaaaat gcttaaatgg tggtttattc ctgcaaacgt tgttctggct     300
tcgatatcag gttccctaat tggattaatt gttgcattaa ttgttcgtcc tccatacccc     360
ttcttcaagt tcacaattgt acaaattgga attgggaaca ttggaaatgt gcctctcgtt     420
ctcattgcag ctctatgtag agatgatatg aatcctttg gtgatgaaga gaatgtagc      480 actgatggga ttgcttatat ttcatatggc cagtgggttg gtgcaattat cctgtacacc     540
tatgtttatg cgatgctggc acctccacct gagggtacat ttgacatcaa agatcaaaat     600
attccagtta agaatctgct aaaggataat acgcctgcac atgttccctt gctcattcag     660
gaggtagctt caaatatcc ggatgctcct aagaaggaag agactaaggg cttccttatg     720
tattggtttg acaaattgaa gctcaagcaa attttcagc ctcctatcat tgcttcggtc      780
ctagctatgt tattgggtgc aactccattc ttaaggcgat tgatctttac tcctgatgct     840
ccattgtttt tcttcactga tagctgcata atgctcgggg aggctatgat tccatgtatc     900
ctgttggcat tgggaggaaa cctcgttgaa ggtcctggaa gttcaaaact cgggctacgg     960
actaccgctg ctgttatttt tgcaaggttg gttttggttc ctcctgcagg ggttggcata    1020
gtcatgttag ccgacaagct tggcttcctt cctccagatg ataaaatgtt ccgattcgtt    1080
cttcttcttc agcattcgat gccaacatct gtcctctcga gtgctgtggc tactttgagg    1140
ggttgtggta gagaatctgc tgctattctt ttctgggttc atatatttgc cgtcatctca    1200
```

```
atggcagggt ggttcatcct ctacttcagg atactcttct aa                    1242
```

<210> SEQ ID NO 2
<211> LENGTH: 411
<212> TYPE: PRT
<213> ORGANISM: Cucumis melo

<400> SEQUENCE: 2

Met Glu Arg Phe Leu Ser Ala Ile Val Ser Glu Val Gln Ala Gly Gly
1               5                   10                  15

Asn Ser Leu Leu Val Thr Ile Lys Ile Ala Val Leu Pro Ile Ala Lys
            20                  25                  30

Val Phe Thr Met Cys Phe Leu Gly Phe Leu Met Ala Ser Lys Tyr Val
        35                  40                  45

Asn Ile Leu Pro Ala Ser Gly Arg Lys Leu Leu Asn Gly Leu Val Phe
    50                  55                  60

Ser Leu Leu Leu Pro Cys Leu Ile Phe Ser Gln Leu Gly Gln Ala Ile
65                  70                  75                  80

Thr Leu Glu Lys Met Leu Lys Trp Trp Phe Ile Pro Ala Asn Val Val
                85                  90                  95

Leu Ala Ser Ile Ser Gly Ser Leu Ile Gly Leu Ile Val Ala Leu Ile
            100                 105                 110

Val Arg Pro Pro Tyr Pro Phe Phe Lys Phe Thr Ile Val Gln Ile Gly
        115                 120                 125

Ile Gly Asn Ile Gly Asn Val Pro Leu Val Leu Ile Ala Ala Leu Cys
    130                 135                 140

Arg Asp Asp Met Asn Pro Phe Gly Asp Glu Glu Lys Cys Ser Thr Asp
145                 150                 155                 160

Gly Ile Ala Tyr Ile Ser Tyr Gly Gln Trp Val Gly Ala Ile Ile Leu
                165                 170                 175

Tyr Thr Tyr Val Tyr Ala Met Leu Ala Pro Pro Glu Gly Thr Phe
            180                 185                 190

Asp Ile Lys Asp Gln Asn Ile Pro Val Lys Asn Leu Leu Lys Asp Asn
        195                 200                 205

Thr Pro Ala His Val Pro Leu Leu Ile Gln Glu Val Ala Ser Lys Tyr
    210                 215                 220

Pro Asp Ala Pro Lys Lys Glu Glu Thr Lys Gly Phe Leu Met Tyr Trp
225                 230                 235                 240

Phe Asp Lys Leu Lys Leu Lys Gln Ile Phe Gln Pro Ile Ile Ala
                245                 250                 255

Ser Val Leu Ala Met Leu Leu Gly Ala Thr Pro Phe Leu Arg Arg Leu
            260                 265                 270

Ile Phe Thr Pro Asp Ala Pro Leu Phe Phe Thr Asp Ser Cys Ile
        275                 280                 285

Met Leu Gly Glu Ala Met Ile Pro Cys Ile Leu Leu Ala Leu Gly Gly
    290                 295                 300

Asn Leu Val Glu Gly Pro Gly Ser Ser Lys Leu Gly Leu Arg Thr Thr
305                 310                 315                 320

Ala Ala Val Ile Phe Ala Arg Leu Val Leu Val Pro Ala Gly Val
                325                 330                 335

Gly Ile Val Met Leu Ala Asp Lys Leu Gly Phe Leu Pro Pro Asp Asp
            340                 345                 350

Lys Met Phe Arg Phe Val Leu Leu Leu Gln His Ser Met Pro Thr Ser
        355                 360                 365

Val Leu Ser Ser Ala Val Ala Thr Leu Arg Gly Cys Gly Arg Glu Ser
        370                 375                 380

Ala Ala Ile Leu Phe Trp Val His Ile Phe Ala Val Ile Ser Met Ala
385                 390                 395                 400

Gly Trp Phe Ile Leu Tyr Phe Arg Ile Leu Phe
                405                 410

<210> SEQ ID NO 3
<211> LENGTH: 1254
<212> TYPE: DNA
<213> ORGANISM: Cucumis melo

<400> SEQUENCE: 3

```
atggacatgg aaagatttct ctcagccatc gtctcggaag ttcaagcggg agggaactct      60
ctgcttgtca ctattaagat tgctgtgtta cccatagcca agttttcac tatgtgcttt      120
ctgggttttc ttatggcatc taaatatgtc aacatcttgc ctgcaagtgg aaggaagctt     180
ttgaatgggt tggtcttttc gcttttgctt ccatgtttaa tattctctca gctcgggcaa    240
gctattactc tcgagaaaat gcttaaatgg tggtttattc ctgcaaacgt tgttctggct    300
tcgatatcag gttccctaat tggattaatt gttgcattaa ttgttgcatt aattgttcgt    360
cctccatacc ccttcttcaa gttcacaatt gtacaaattg aattgggaa cattggaaat    420
gtgcctctcg ttctcattgc agctctatgt agagatgata tgaatccttt tggtgatgaa    480
gagaaatgta gcactgatgg gattgcttat atttcatatg ccagtgggt tggtgcaatt    540
atcctgtaca cctatgttta tgcgatgctg gcacctccac ctgagggtac atttgacatc    600
aaagatcaaa atattccagt taagaatctg ctaaaggata tacgcctgc acatgttccc    660
ttgctcattc aggaggtagc ttcaaaatat ccggatgctc ctaagaagga agagactaag   720
ggcttcctta tgtattggtt tgacaaattg aagctcaagc aaattttca gcctcctatc    780
attgcttcgg tcctagctat gttattgggt gcaactccat tcttaaggcg attgatcttt    840
actcctgatg ctccattgtt tttcttcact gatagctgca taatgctcgg ggaggctatg    900
attccatgta tcctgttggc attgggagga aacctcgttg aaggtcctgg aagttcaaaa    960
ctcgggctac ggactaccgc tgctgttatt tttgcaaggt tggttttggt tcctcctgca   1020
ggggttggca tagtcatgtt agccgacaag cttggcttcc ttcctccaga tgataaaatg   1080
ttccgattcg ttcttcttct tcagcattcg atgccaacat ctgtcctctc gagtgctgtg   1140
gctactttga ggggttgtgg tagagaatct gctgctattc ttttctgggt tcatatattt   1200
gccgtcatct caatggcagg gtggttcatc ctctacttca ggatactctt ctaa         1254
```

<210> SEQ ID NO 4
<211> LENGTH: 415
<212> TYPE: PRT
<213> ORGANISM: Cucumis melo

<400> SEQUENCE: 4

Met Glu Arg Phe Leu Ser Ala Ile Val Ser Glu Val Gln Ala Gly Gly
1               5                   10                  15

Asn Ser Leu Leu Val Thr Ile Lys Ile Ala Val Leu Pro Ile Ala Lys
            20                  25                  30

Val Phe Thr Met Cys Phe Leu Gly Phe Leu Met Ala Ser Lys Tyr Val
        35                  40                  45

Asn Ile Leu Pro Ala Ser Gly Arg Lys Leu Leu Asn Gly Leu Val Phe
    50                  55                  60

```
Ser Leu Leu Leu Pro Cys Leu Ile Phe Ser Gln Leu Gly Gln Ala Ile
 65                  70                  75                  80

Thr Leu Glu Lys Met Leu Lys Trp Trp Phe Ile Pro Ala Asn Val Val
                 85                  90                  95

Leu Ala Ser Ile Ser Gly Ser Leu Ile Gly Leu Ile Val Ala Leu Ile
            100                 105                 110

Val Ala Leu Ile Val Arg Pro Pro Tyr Pro Phe Phe Lys Phe Thr Ile
        115                 120                 125

Val Gln Ile Gly Ile Gly Asn Ile Gly Asn Val Pro Leu Val Leu Ile
    130                 135                 140

Ala Ala Leu Cys Arg Asp Asp Met Asn Pro Phe Gly Asp Glu Glu Lys
145                 150                 155                 160

Cys Ser Thr Asp Gly Ile Ala Tyr Ile Ser Tyr Gly Gln Trp Val Gly
                165                 170                 175

Ala Ile Ile Leu Tyr Thr Tyr Val Tyr Ala Met Leu Ala Pro Pro Pro
            180                 185                 190

Glu Gly Thr Phe Asp Ile Lys Asp Gln Asn Ile Pro Val Lys Asn Leu
        195                 200                 205

Leu Lys Asp Asn Thr Pro Ala His Val Pro Leu Leu Ile Gln Glu Val
    210                 215                 220

Ala Ser Lys Tyr Pro Asp Ala Pro Lys Lys Glu Glu Thr Lys Gly Phe
225                 230                 235                 240

Leu Met Tyr Trp Phe Asp Lys Leu Lys Leu Lys Gln Ile Phe Gln Pro
                245                 250                 255

Pro Ile Ile Ala Ser Val Leu Ala Met Leu Leu Gly Ala Thr Pro Phe
            260                 265                 270

Leu Arg Arg Leu Ile Phe Thr Pro Asp Ala Pro Leu Phe Phe Phe Thr
        275                 280                 285

Asp Ser Cys Ile Met Leu Gly Glu Ala Met Ile Pro Cys Ile Leu Leu
    290                 295                 300

Ala Leu Gly Gly Asn Leu Val Glu Gly Pro Gly Ser Ser Lys Leu Gly
305                 310                 315                 320

Leu Arg Thr Thr Ala Ala Val Ile Phe Ala Arg Leu Val Leu Val Pro
                325                 330                 335

Pro Ala Gly Val Gly Ile Val Met Leu Ala Asp Lys Leu Gly Phe Leu
            340                 345                 350

Pro Pro Asp Asp Lys Met Phe Arg Phe Val Leu Leu Gln His Ser
        355                 360                 365

Met Pro Thr Ser Val Leu Ser Ser Ala Val Ala Thr Leu Arg Gly Cys
    370                 375                 380

Gly Arg Glu Ser Ala Ala Ile Leu Phe Trp Val His Ile Phe Ala Val
385                 390                 395                 400

Ile Ser Met Ala Gly Trp Phe Ile Leu Tyr Phe Arg Ile Leu Phe
                405                 410                 415

<210> SEQ ID NO 5
<211> LENGTH: 424
<212> TYPE: PRT
<213> ORGANISM: Lycopersicon esculentum

<400> SEQUENCE: 5

Met Asp Arg Val Ser Arg Ile Leu Phe Ser Val Leu Thr Glu Pro Gln
1               5                   10                  15

Arg Gly Gly Gln Ser Phe Ile Thr Ser Ile Lys Ile Ala Val Leu Pro
```

```
            20                  25                  30
Ile Ala Lys Val Phe Thr Leu Cys Phe Leu Gly Phe Leu Met Ala Ser
            35                  40                  45

Lys Tyr Val Asn Ile Leu Pro Ala Asn Gly Arg Lys Leu Leu Asn Gly
 50                  55                  60

Leu Val Phe Ser Leu Leu Pro Cys Leu Ile Phe Ser Gln Leu Gly
 65                  70                  75                  80

Gln Ala Ile Thr Tyr Glu Lys Leu Leu Gln Trp Trp Phe Ile Pro Val
                 85                  90                  95

Asn Ile Val Leu Ala Thr Ile Phe Gly Ser Ile Ile Gly Leu Ile Val
                100                 105                 110

Ala Thr Ile Val Arg Pro Pro Tyr Pro Tyr Phe Lys Phe Thr Ile Ile
                115                 120                 125

Gln Ile Gly Ile Gly Asn Ile Gly Asn Val Pro Leu Val Leu Ile Ala
                130                 135                 140

Ala Leu Cys Arg Asp Pro Ser Asn Pro Phe Gly Asp Ser Glu Ile Cys
145                 150                 155                 160

Ala Arg Asp Gly Asn Ala Tyr Ile Ser Phe Gly Gln Trp Val Gly Ala
                165                 170                 175

Ile Ile Leu Tyr Thr Phe Val Phe Gln Met Leu Ser Pro Pro Pro Glu
                180                 185                 190

Gly Ser Phe Asp Val Glu Asp Ala Asn Leu Pro Ile Lys Val Pro Asn
                195                 200                 205

Lys Glu Arg Leu Pro Ser His Pro Ser Gly Ser Ser Ala Glu Gln Val
                210                 215                 220

Pro Leu Leu Ala Thr Asn Val Ala Pro Ala Asp Ser Ser Ser Ser Asn
225                 230                 235                 240

Lys Glu Lys Val Lys Gln Phe Lys Phe Leu Tyr Glu Thr Leu Lys
                245                 250                 255

Leu Lys Gln Leu Ile Gln Pro Pro Ile Ile Ala Ser Ile Ile Ala Ile
                260                 265                 270

Ile Ile Gly Cys Val Pro Val Leu Lys Arg Leu Ile Phe Thr Ser Asp
                275                 280                 285

Ala Pro Leu Tyr Phe Phe Thr Asp Ser Cys Leu Ile Leu Gly Asp Ala
                290                 295                 300

Met Ile Pro Cys Ile Leu Leu Ala Leu Gly Gly Asn Leu Val Asp Gly
305                 310                 315                 320

Pro Gly Pro Gly Ser Ser Lys Ile Gly Leu Lys Thr Thr Val Ala Ile
                325                 330                 335

Val Phe Ala Pro Val Val Phe Gly Ser Ser Asn Trp Thr Gln Ile Val
                340                 345                 350

Met Leu Ala Asp Lys Leu Gly Phe Leu Pro Ala Asp Asp Lys Met Phe
                355                 360                 365

Arg Phe Val Leu Leu Leu Gln Tyr Ser Met Pro Thr Ser Ile Leu Ala
                370                 375                 380

Gly Ala Val Ala Asn Leu Arg Gly Cys Gly Lys Glu Ala Ala Ser Ile
385                 390                 395                 400

Leu Phe Trp Val His Ile Phe Ala Val Ile Ser Met Ala Gly Trp Ile
                405                 410                 415

Ile Leu Tyr Leu Asn Ile Leu Phe
                420
```

<210> SEQ ID NO 6

<211> LENGTH: 453
<212> TYPE: PRT
<213> ORGANISM: Cucumis sativus

<400> SEQUENCE: 6

```
Met Glu Asn Phe Leu Ser Ala Ile Val Ser Glu Val Gln Ala Gly Gly
1               5                   10                  15

Asn Ser Leu Leu Val Thr Ile Lys Ile Ala Val Leu Pro Ile Ala Lys
            20                  25                  30

Val Phe Thr Met Cys Phe Leu Gly Phe Leu Met Ala Ser Lys Tyr Val
        35                  40                  45

Asn Ile Leu Pro Ala Ser Gly Arg Lys Leu Leu Asn Gly Leu Val Phe
    50                  55                  60

Ser Leu Leu Leu Pro Cys Leu Ile Phe Ser Gln Leu Gly Gln Ala Ile
65                  70                  75                  80

Thr Leu Glu Lys Met Leu Lys Trp Trp Phe Ile Pro Ala Asn Val Val
                85                  90                  95

Leu Ala Ser Ile Ser Gly Ser Leu Ile Gly Leu Ile Val Ala Ser Ile
            100                 105                 110

Val Arg Pro Pro Tyr Pro Phe Phe Lys Phe Thr Ile Val Gln Ile Gly
        115                 120                 125

Ile Gly Asn Ile Gly Asn Val Pro Leu Val Leu Ile Ala Ala Leu Cys
    130                 135                 140

Arg Asp Asp Met Asn Pro Phe Gly Asp Glu Glu Lys Cys Ser Thr Asp
145                 150                 155                 160

Gly Ile Ala Tyr Ile Ser Tyr Gly Gln Trp Val Gly Ala Ile Ile Leu
                165                 170                 175

Tyr Thr Tyr Val Tyr Ala Met Leu Ala Pro Pro Glu Gly Thr Phe
            180                 185                 190

Asp Ile Lys Asp Gln Asn Ile Ser Val Lys Asn Leu Leu Lys Asp Asn
        195                 200                 205

Thr Pro Ala His Val Pro Leu Leu Ile Gln Glu Val Pro Ser Thr Tyr
    210                 215                 220

Pro Asp Ala Pro Lys Lys Glu Glu Lys Tyr Asp Met Glu Tyr Glu Lys
225                 230                 235                 240

Cys Asn Asn Asp Asn Lys Thr Ser Thr Tyr Phe His Asn Gly Ile Ile
                245                 250                 255

Leu Ser Thr Leu Gly Ile Phe Pro His Ser Leu Thr Phe Gly Ile Thr
            260                 265                 270

Gln Lys Thr Lys Gly Phe Leu Ile Tyr Trp Phe Asp Lys Leu Lys Leu
        275                 280                 285

Lys Gln Met Phe Gln Pro Pro Ile Val Ala Ser Val Leu Ala Met Leu
    290                 295                 300

Leu Gly Ala Thr Pro Phe Leu Arg Arg Leu Ile Phe Thr Pro Asp Ala
305                 310                 315                 320

Pro Leu Phe Phe Phe Thr Asp Ser Cys Ile Met Leu Gly Glu Ala Met
                325                 330                 335

Ile Pro Cys Ile Leu Leu Ala Leu Gly Gly Asn Leu Val Glu Gly Pro
            340                 345                 350

Gly Ser Ser Lys Leu Gly Leu Arg Thr Thr Ala Ala Ile Ile Phe Ala
        355                 360                 365

Arg Leu Val Leu Val Pro Pro Ala Gly Leu Gly Ile Val Met Leu Ala
    370                 375                 380

Asp Lys Leu Gly Phe Leu Pro Pro Asp Asp Lys Met Phe Arg Phe Val
```

```
                385                 390                 395                 400
Leu Leu Leu Gln His Ser Met Pro Thr Ser Val Leu Ser Ala Val
                    405                 410                 415

Ala Thr Leu Arg Gly Cys Gly Lys Asp Ser Ala Ile Leu Phe Trp
            420                 425                 430

Val His Ile Phe Ser Val Ile Ser Met Ala Gly Trp Phe Ile Leu Tyr
        435                 440                 445

Phe Arg Ile Leu Phe
    450

<210> SEQ ID NO 7
<211> LENGTH: 22
<212> TYPE: DNA
<213> ORGANISM: Artificial sequence
<220> FEATURE:
<223> OTHER INFORMATION: Sigle strand DNA oligonucleotide

<400> SEQUENCE: 7
atggacatgg aaagatttct ct                                           22

<210> SEQ ID NO 8
<211> LENGTH: 422
<212> TYPE: PRT
<213> ORGANISM: Malus domestica

<400> SEQUENCE: 8

Met Glu Arg Ile Leu Ala Ala Val Glu Val Asn Gln Ala Gly Gly
1               5                   10                  15

Glu Ser Leu Leu Gly Thr Ile Lys Ile Ala Val Leu Pro Ile Ala Lys
            20                  25                  30

Val Phe Thr Val Cys Ser Leu Gly Leu Leu Met Ala Ser Lys Tyr Val
        35                  40                  45

Asn Ile Phe Pro Ala Ser Gly Arg Lys Leu Leu Asn Gly Leu Val Phe
    50                  55                  60

Ser Leu Leu Leu Pro Cys Leu Ile Phe Ser Gln Leu Gly Gln Ala Ile
65                  70                  75                  80

Thr Leu Gln Lys Met Leu Glu Trp Trp Phe Ile Pro Val Asn Val Val
                85                  90                  95

Ile Gly Ser Thr Thr Gly Ser Ile Ile Gly Tyr Ile Val Ala Ser Leu
            100                 105                 110

Val His Pro Pro Tyr Pro Phe Phe Lys Phe Thr Ile Val Gln Ile Gly
        115                 120                 125

Ile Gly Asn Ile Gly Asn Val Pro Leu Val Leu Ile Ser Ala Leu Cys
    130                 135                 140

Arg Asp Lys Ser Asn Pro Phe Gly Asp Ser Thr Thr Cys Lys Thr Asp
145                 150                 155                 160

Gly Thr Ala Tyr Ile Ser Phe Gly Gln Trp Val Gly Ala Ile Ile Leu
                165                 170                 175

Tyr Thr Tyr Val Phe Gln Met Leu Ser Pro Pro Glu Gly Thr Phe
            180                 185                 190

Asp Val Glu Glu Lys Glu Leu Pro Ile Lys Ser Pro Arg Asn Gly Thr
        195                 200                 205

Thr Pro Asp Gln Val Pro Leu Leu Thr Pro Asp Glu Asn Glu Glu
    210                 215                 220

Thr Ala Arg Lys Glu Glu Val Ala Glu Thr Glu Ser Asn Ala Ser Asn
225                 230                 235                 240
```

```
Lys Pro Lys Ile Thr Lys Phe Phe Leu Phe Ile Tyr Glu Lys Leu Lys
                245                 250                 255

Leu Lys Gln Val Leu Gln Pro Pro Ile Ile Ala Ser Ile Leu Ala Met
                260                 265                 270

Val Leu Gly Thr Ile Pro Phe Leu Lys Lys Leu Ile Phe Thr Ser Asp
                275                 280                 285

Gly Pro Leu Phe Phe Phe Thr Asp Ser Cys Ile Ile Leu Gly Glu Ala
                290                 295                 300

Met Ile Pro Cys Ile Leu Leu Ala Leu Gly Asn Leu Val Asp Gly
305                 310                 315                 320

Pro Gly Ser Ser Lys Leu Gly Leu Arg Thr Thr Ala Ala Ile Ile Phe
                325                 330                 335

Ala Arg Leu Val Leu Val Pro Pro Val Gly Leu Gly Val Val Met Leu
                340                 345                 350

Ala Asp Lys Leu Gly Phe Leu Pro Pro Asn Asp Gln Met Phe Arg Phe
                355                 360                 365

Val Leu Leu Leu Gln His Thr Met Pro Thr Ser Val Leu Ala Gly Ala
                370                 375                 380

Val Ala Asn Leu Arg Gly Cys Gly Arg Glu Ala Ala Ala Val Leu Phe
385                 390                 395                 400

Trp Val His Ile Phe Ala Ile Phe Ser Met Ala Gly Trp Ile Val Leu
                405                 410                 415

Tyr Leu Asn Ile Leu Phe
                420

<210> SEQ ID NO 9
<211> LENGTH: 414
<212> TYPE: PRT
<213> ORGANISM: Populus trichocarpa

<400> SEQUENCE: 9

Met Glu Arg Phe Leu Leu Ala Val Asp Thr Met Gly Ala Asn Gln Val
1               5                   10                  15

Gly Gly Gly Gln Thr Leu Leu Gly Thr Ile Lys Ile Ala Val Leu Pro
                20                  25                  30

Ile Ala Lys Val Phe Thr Met Cys Phe Leu Gly Phe Leu Met Ala Ser
                35                  40                  45

Lys Tyr Val Asn Ile Leu Pro Ala Ser Gly Arg Lys Leu Leu Asn Gly
                50                  55                  60

Leu Val Phe Ser Leu Leu Leu Pro Cys Leu Ile Phe Ser Gln Leu Gly
65                  70                  75                  80

Gln Ala Val Thr Leu Gln Lys Met Leu Glu Trp Trp Phe Ile Pro Val
                85                  90                  95

Asn Val Val Leu Ser Ser Ile Cys Gly Ser Leu Ile Gly Phe Ile Val
                100                 105                 110

Ala Ser Ile Val Arg Pro Pro Tyr Pro Phe Phe Lys Phe Ser Ile Val
                115                 120                 125

Gln Ile Gly Ile Gly Asn Ile Gly Asn Val Pro Leu Val Leu Ile Ala
                130                 135                 140

Ala Leu Cys Arg Asp Thr Ser Asn Pro Phe Gly Asp Ser Glu Lys Cys
145                 150                 155                 160

Ser Thr Asp Gly Thr Ala Tyr Ile Ser Phe Gly Gln Trp Val Gly Ala
                165                 170                 175

Ile Ile Leu Tyr Thr Tyr Val Phe Asn Met Leu Ala Pro Pro Pro Glu
                180                 185                 190
```

```
Gly Thr Phe Asp Ile Asp Glu Pro Asn Leu Pro Ile Lys Lys Pro Ala
            195                 200                 205

Lys Asp Ala Pro Met Glu Gln Val Pro Leu Leu Ala Gln Glu Glu Ala
210                 215                 220

Pro Ala Glu Pro Asp Ala Pro Lys Arg Gly Lys Ile Lys Gln Ile Leu
225                 230                 235                 240

Val Phe Leu Tyr Asp Lys Leu Lys Leu Lys Gln Ile Leu Gln Pro Pro
            245                 250                 255

Ile Ile Ala Ser Ile Leu Ala Met Phe Leu Gly Ala Val Pro Phe Leu
            260                 265                 270

Lys Gln Leu Ile Phe Thr Thr Asp Ser Pro Leu Phe Phe Thr Asp
            275                 280                 285

Ser Cys Asn Ile Leu Gly Glu Ala Met Ile Pro Cys Ile Leu Leu Ala
            290                 295                 300

Leu Gly Gly Asn Leu Val Asp Gly Pro Gly Ser Ser Lys Leu Gly Phe
305                 310                 315                 320

Arg Thr Thr Ala Ala Ile Ile Phe Gly Arg Leu Val Leu Val Pro Pro
            325                 330                 335

Thr Gly Leu Gly Ile Val Met Leu Ala Asp Lys Leu Gly Phe Leu Pro
            340                 345                 350

Ala Gly Asp Lys Met Phe Arg Phe Val Leu Leu Gln His Thr Met
            355                 360                 365

Pro Thr Ser Val Leu Ser Gly Ala Val Ala Asn Leu Arg Gly Cys Gly
            370                 375                 380

Arg Glu Ala Ala Ala Val Leu Phe Trp Val His Ile Phe Ala Ile Phe
385                 390                 395                 400

Ser Met Ala Gly Trp Ile Val Leu Tyr Leu Asn Ile Leu Phe
            405                 410

<210> SEQ ID NO 10
<211> LENGTH: 431
<212> TYPE: PRT
<213> ORGANISM: Arabidopsis thaliana

<400> SEQUENCE: 10

Met Ile Ala Arg Ile Leu Ala Ala Leu Ala Asp Ser Met Glu Met Pro
1               5                   10                  15

Val Ala Ala Gly Gly Ser Val Leu Gly Thr Ile Lys Ile Ala Val
                20                  25                  30

Met Pro Ile Ala Lys Val Phe Thr Met Cys Phe Leu Gly Leu Leu Met
            35                  40                  45

Ala Ser Lys Tyr Val Asn Ile Leu Pro Pro Ser Gly Arg Lys Leu Leu
50                  55                  60

Asn Gly Leu Val Phe Ser Leu Leu Pro Cys Leu Ile Phe Ser Gln
65                  70                  75                  80

Leu Gly Gln Ala Val Thr Leu Gln Lys Met Leu Gln Trp Trp Phe Ile
            85                  90                  95

Pro Val Asn Val Val Leu Gly Thr Ile Ser Gly Ser Ile Ile Gly Phe
            100                 105                 110

Ile Val Ala Ser Ile Val Arg Pro Pro Tyr Pro Tyr Phe Lys Phe Thr
            115                 120                 125

Ile Ile Gln Ile Gly Val Gly Asn Ile Gly Asn Val Pro Leu Val Leu
            130                 135                 140

Leu Ala Ala Leu Cys Arg Asp Thr Ser Asn Pro Phe Gly Asp Ser Glu
```

```
            145                 150                 155                 160
Lys Cys Ser Ile Asp Gly Thr Ala Tyr Ile Ser Phe Gly Gln Trp Val
                165                 170                 175

Gly Ala Ile Ile Leu Tyr Thr Tyr Val Tyr Gln Met Phe Ala Pro Pro
            180                 185                 190

Pro Glu Gly Phe Asp Ala Glu Glu Asn Leu Ala Leu Lys Thr Leu
        195                 200                 205

Pro Val Asp Ala Ala Pro Glu Gln Val Pro Leu Leu Thr Gln Asn Phe
    210                 215                 220

Pro Lys Asp Phe Ser Pro Thr Gln Asp Leu Leu Pro Val Gln Ser Thr
225                 230                 235                 240

Glu Pro Arg Gly Arg Gly Val Ser Arg Lys Gly Lys Ile Ala Gln Ile
                245                 250                 255

Phe Val Phe Leu Tyr Glu Lys Leu Lys Leu Lys Gln Ile Val Gln Pro
            260                 265                 270

Ala Ile Val Ala Ser Ile Leu Ala Met Ile Leu Gly Ala Ile Pro Phe
        275                 280                 285

Thr Lys Lys Leu Ile Phe Thr Asn Gly Ala Pro Leu Phe Phe Phe Thr
    290                 295                 300

Asp Ser Cys Met Ile Leu Gly Asp Ala Met Ile Pro Cys Ile Leu Leu
305                 310                 315                 320

Ala Leu Gly Gly Asn Leu Ile Asn Gly Pro Gly Ser Ser Lys Leu Gly
                325                 330                 335

Phe Lys Thr Thr Ala Ala Ile Ile Ile Gly Arg Leu Val Leu Val Pro
            340                 345                 350

Pro Val Gly Leu Gly Ile Val Thr Val Ala Asp Lys Leu Gly Phe Leu
        355                 360                 365

Pro Ala Asp Asp Lys Met Phe Arg Phe Val Leu Leu Leu Gln His Thr
    370                 375                 380

Met Pro Thr Ser Val Leu Ser Gly Ala Val Ala Asn Leu Arg Gly Cys
385                 390                 395                 400

Gly Arg Glu Ser Ala Ala Val Leu Phe Trp Val His Ile Phe Ala Ile
                405                 410                 415

Phe Ser Met Ala Gly Trp Met Val Leu Tyr Ile Asn Ile Leu Phe
            420                 425                 430

<210> SEQ ID NO 11
<211> LENGTH: 23
<212> TYPE: DNA
<213> ORGANISM: Artificial sequence
<220> FEATURE:
<223> OTHER INFORMATION: Sigle strand DNA oligonucleotide

<400> SEQUENCE: 11
ttagaagagt atcctgaagt aga                                            23

<210> SEQ ID NO 12
<211> LENGTH: 18
<212> TYPE: DNA
<213> ORGANISM: Artificial sequence
<220> FEATURE:
<223> OTHER INFORMATION: Sigle strand DNA oligonucleotide

<400> SEQUENCE: 12
ctcgggcaag ctattact                                                  18

<210> SEQ ID NO 13
```

```
<211> LENGTH: 18
<212> TYPE: DNA
<213> ORGANISM: Artificial sequence
<220> FEATURE:
<223> OTHER INFORMATION: Sigle strand DNA oligonucleotide

<400> SEQUENCE: 13
gtatggagga cgaacaat                                                   18

<210> SEQ ID NO 14
<211> LENGTH: 7962
<212> TYPE: DNA
<213> ORGANISM: Cucumis melo
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (32)..(34)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (94)..(95)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (109)..(110)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
```

-continued

```
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (316)..(316)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (4305)..(4305)
<223> OTHER INFORMATION: n is a, c, g, or t
<220> FEATURE:
<221> NAME/KEY: misc_feature
<222> LOCATION: (5729)..(5729)
<223> OTHER INFORMATION: n is a, c, g, or t
<220> FEATURE:
<221> NAME/KEY: misc_feature
<222> LOCATION: (6118)..(6118)
<223> OTHER INFORMATION: n is a, c, g, or t
<220> FEATURE:
<221> NAME/KEY: misc_feature
<222> LOCATION: (6232)..(6232)
<223> OTHER INFORMATION: n is a, c, g, or t
<220> FEATURE:
<221> NAME/KEY: misc_feature
<222> LOCATION: (6571)..(6571)
<223> OTHER INFORMATION: n is a, c, g, or t
<220> FEATURE:
<221> NAME/KEY: misc_feature
<222> LOCATION: (6631)..(6631)
<223> OTHER INFORMATION: n is a, c, g, or t
<220> FEATURE:
<221> NAME/KEY: misc_feature
<222> LOCATION: (7797)..(7797)
```

```
<223> OTHER INFORMATION: n is a, c, g, or t
<220> FEATURE:
<221> NAME/KEY: misc_feature
<222> LOCATION: (7822)..(7822)
<223> OTHER INFORMATION: n is a, c, g, or t
<220> FEATURE:
<221> NAME/KEY: misc_feature
<222> LOCATION: (7838)..(7838)
<223> OTHER INFORMATION: n is a, c, g, or t
<220> FEATURE:
<221> NAME/KEY: misc_feature
<222> LOCATION: (7872)..(7872)
<223> OTHER INFORMATION: n is a, c, g, or t
<220> FEATURE:
<221> NAME/KEY: misc_feature
<222> LOCATION: (7907)..(7908)
<223> OTHER INFORMATION: n is a, c, g, or t
<220> FEATURE:
<221> NAME/KEY: misc_feature
<222> LOCATION: (7931)..(7932)
<223> OTHER INFORMATION: n is a, c, g, or t
<220> FEATURE:
<221> NAME/KEY: misc_feature
<222> LOCATION: (7941)..(7941)
<223> OTHER INFORMATION: n is a, c, g, or t
<220> FEATURE:
<221> NAME/KEY: misc_feature
<222> LOCATION: (7948)..(7949)
<223> OTHER INFORMATION: n is a, c, g, or t
<220> FEATURE:
<221> NAME/KEY: misc_feature
<222> LOCATION: (7958)..(7958)
<223> OTHER INFORMATION: n is a, c, g, or t

<400> SEQUENCE: 14
```

| | | | | | |
|---|---|---|---|---|---|
| angggttcgc | gttggccgat | tcattnatgc | annnggcncg | ncagntttnc | cgactgnaaa | 60
| gcggncagtg | agcgcnacnc | aattnatgtg | agtnngctca | ctcattngnn | accccnggnc | 120
| tttacactt | atgcttccgg | ctcgtatgtt | gtgngnaatn | gtgagcggat | aacaatttca | 180
| cacaggaanc | agctatgacc | atgattacgc | caagctattt | aggtgacact | atagaatant | 240
| caagcttgca | tgnctgcagg | tngactctag | aggatcccg | ggnaccgagc | tngaattcaa | 300
| gaacataatc | gaaatnttct | tcaactntcg | tagctaaatt | ngtaattcca | ccattaaatt | 360
| cgttgttact | ttgtggcata | tgaatgtcaa | aacttgctgt | ccttttcaat | ctacggattt | 420
| gtgcggtgaa | atattccact | tcaacgacga | acagtaggaa | ttgagcagcg | caatatttgg | 480
| cgcgcagttg | ctttactagc | aggctctcac | aaatcgccat | tgccaaacct | cagagctgct | 540
| tttcaactct | ttatcttcat | cctcttcatc | cattttcact | tttttttct | tttttgaaa | 600
| atttcagatt | aggatctgtt | cttgtttctc | tgtaagtgtt | ttctcgttaa | ttctctcttt | 660
| ttatcgctat | aatttgttgt | tatggcttct | ggggtttgtt | ttgtgggttt | tttttttt | 720
| ttatgaagct | ttattgttag | tattcagtgc | atgaacgttt | ttcaagaaat | ttgtgtcgct | 780
| atcagcattt | cttttcgac | attctatttc | tggatttagt | ttttattttg | tgttgctttg | 840
| attgtgatgc | tacttccggt | tctgaaatga | tttcattgtt | ctacttcctt | gtttttgctt | 900
| ctgattctta | attattcttt | tttttttttt | ttggattgtt | cttgttttgt | aaagtttaaa | 960
| ttatgttttg | tgatcaggaa | aactgagaag | caaaatttcc | cgaacttcat | gttttgatga | 1020
| ttaagtccga | gtgctgagat | ttagtccgtt | tggaatttgg | tgggtttaca | aaggaacccc | 1080
| tatttcatat | agaacgagtt | tcagattttg | agttttgttt | ggtggtgatc | agaagattga | 1140
| gtgacaaaga | ggagatggac | atggaaagat | ttctctcagc | catcgtctcg | gaagttcaag | 1200
| cgggagggaa | ctctctgctt | gtcactatta | agattgctgt | gttacccata | gccaaagttt | 1260
| tcactatgtg | ctttctgggt | tttcttatgg | catctaaata | tgtcaacatc | ttgcctgcaa | 1320

```
gtggaaggaa gcttttgaat ggggtatgtt tgcataaatt tcatctaatc tgtacactga    1380
acagactctg tattgttttc tgatttgatg ttttgatgga cctatctaaa cacgatgact    1440
agtattttga tgggttcaaa atgattttc attttgctt cttgtgctgc agttggtctt     1500
ttcgcttttg cttccatgtt taatattctc tcagctcggg caagctatta ctctcgagaa    1560
aatgcttaaa tggtgggagc taaatatact ttacacgtgt tcctgttttg atttgaatct    1620
tgtatacaga gaacagtcat ctaatttcat ttgtggcctt attatgtagg tggtttattc    1680
ctgcaaacgt tgttctggct tcgatatcag gttccctaat tggattaatt gttgcattaa    1740
ttgttcgtcc tccatacccc ttcttcaagt tcacaattgt acaaattgga attggtaaac    1800
cacttgatct tggaatagta cttgcacata gtttgtctgt atgatgtatg agttgtttcc    1860
tgtttgtcac ttgattggct ggtcatttca gatatctgtt aatggccatc agtttataac    1920
tccttatggc ctgtcagttt ttagttcaaa aactagaata gtatttctct tttccggatt    1980
gtgcatcaat tctttgcact aattgaatgg cactgtgagg tttgtgctgc atgtgacaca    2040
aaccaatcat gttggccgga cattgatcca caattgcaga caaataaatt aggagagctg    2100
ttcaaatgaa tatacgttgt caataactta atggatcaag gaacgaatca gagggttcca    2160
aacttgctaa ttcaacaacg cagacctagt tttaataggg aattttcaat gatttggcct    2220
tatgtgatgg atgctagcat atgctatcct tctgatacat tttccttacc tacctaaact    2280
caagatgagt ttattcattt cttgttttg tagtattttt cttttgaata atcctgtatt     2340
gagagcccca ctcccaacta attcaggtac ccatgcctat gcaggccctg aactcagtct    2400 tattttgta agtcttttag ctgactgtta gtttgattag aagtaatatc tagttctaat     2460
taagcctgcc aaagccagtg tgctactggt ataaatcata tcattaatat tatgaaaata    2520
acgatgattg aataataaag atgagtttcc tttcccactt ccctctgttg gaaggtacat    2580
tgtacttgca ttttagagta agtttcaagt aaacacttcc tgtagtgtca aacgaattgc    2640
aatatccttg accttgtgtc ttaattcacc cgttttttt ttttttcctt tctgtgtgaa     2700
agatgaagaa ttgattaaac aaataatagg gtttctgtac tttaaaatgc agtagctgta    2760
gatatgctgt gaaaatattt acttgaactt catgatttgg ttttctcata tgaacgtatt    2820
atttatgcat ccttgttgct attctatgtt ttgatgttgg cattcaggga acattggaaa    2880
tgtgcctctc gttctcattg cagctctatg tagagatgat atgaatcctt ttggtgatga    2940
agagaaatgt agcactgatg ggattgctta tatttcatat ggccagtggg tgggtttttc    3000 tgcgttttg gctcaactca tttgacttg tgcatttttc tgaagttgga tttttttttt      3060 ttaaatttt aattactctt catcatatat cattctaaat accaattatt ccatccatga     3120
cttggcttgt attcattcct aagtaacatg ttcttttat aatttaggcc ccatggcttg     3180
aagcgaacaa tatacacttt aatgaaaaag agagtggaag aagtatttga taaatacgta    3240
ccattattct aattggtatt cactattcac aatcaaattt cattttaag tactctccct     3300 tgcaattaac tcaagatggg gtgcatcttt gtgactcctt caggaaattt ttaccctatc    3360
aatggctttg ttattaagaa aagaaataat aaataaataa aaaattaaac atttgttact    3420
agcaaacaac ctaatctaaa tttactaata cctacgtgat tattttttaa tgtcaaggtt    3480
ggtgcaatta tcctgtacac ctatgtttat gcgatgctgg cacctccacc tgagggtaca    3540
tttgacatca aagatcaaaa tattccagtt aagaatctgc taaaggataa tacgcctgca    3600
catgttccct tgctcattca ggaggtagct tcaaaatatc cggatgctcc taagaaggaa    3660
```

```
gaggtgagag actttatttt tctttattgt aagcattgcc atattcagtt taatggattc    3720
atggcgaggt tcatttctat taatcaactt ataatagcat attttatatt tttctagaag    3780
actaatatga cattctttta tagaagtatg atatggaata tgaaaaatgt aataacgata    3840
acaagacctc cacctatttt cataatagta taatattgtc cactttggat ataaatcctc    3900
gtagccttac ttttggaatc acccaaaagg tctcatataa atggagataa ttgttcttcg    3960
cttaccatag atctctcctt tccctaacca acatgggact ttatttacac cagaacataa    4020
tggatgtaaa tgttatcatc ttcaattttt agcagcttct ctgtgttttg ggttattcat    4080
tagttaattt atcttgcctt agttatggtt ttgaactagt ctactctttg taatgaaaac    4140
taagctctgt tttcggatta tgcattagtt aatttctgtt gccttagttt tggttttatg    4200
aaaacaaatc tactcttagt tgtgaaacta gtatgttaaa ttgtcagaag atttttagat    4260
cagttgtgtc aatattcttg gcttcatgtt tcttttttgc tttcnagcta agcagtggaa    4320
aatcattctt tctaaaatta tgaagatttg gatgacttct tggctttatt aggttagcta    4380
acttatctta agtggcagtt tgttcattca tccttacttc tgaaaggaaa tacaaaattg    4440
gggctgtctg tcacaatttt tctttggatg cagactaagg gcttccttat gtattggttt    4500
gacaaattga agctcaagca aattttttcag cctcctatca ttgcttcggt tagtatatat    4560
ttgtgtttta atgtgctgta gtcttatcat ttgttttatg gatcatacta taactagtga    4620
atgctagata aatttcgtgg gagcatatgt ttcatcctct tttgaaattg taaactgaaa    4680
tgttgttttc ggaaaaaaat tgagtttgtt ttgttctctt gaaaagaaaa gaaaacaatg    4740
ggttgggttt agggtttgtt ctcttcatga acatctgata tgtatcccca aagttaaagt    4800
gatgtttttt attcatctaa ttatgctttt ggggttcatg ttaattgatg aggtttctga    4860
acttccagat tcagatatct ttccaagttc ttttgtcacc tttcgtaatt gattatgcaa    4920
catgttgcag gtcctagcta tgttattggg tgcaactcca ttcttaaggc gattgatctt    4980
tactcctgat gctccattgt ttttcttcac tgatagctgc ataatgctcg ggtaaatcct    5040
ggaaattttt taagagcaat gttgcttttt atttagaatt ataattcttt cgctttgctc    5100
attgatgggc ttgcactgag gttgttttct tggaaggttt cttttagtcc attttttaaga    5160 atggctgcta gatgcctaca cttaaatttc tgtataccta aatatttgat cttaaggtta    5220
tctttgggtt tctgtttcaa gtcaagagct caaattcgta gagtttgtga tgatcatgtc    5280
atgaagattc aaattagccg ttaacagagg gttccacata tctctttggc tttttgtttc    5340
ctggcctttg ttgaggatgc cagcatagtt ccaaatcaca atcaggttga cgtggagagg    5400
gcttttggta aaggcaacat ttttgttggt ataaggattc ttgtggaaaa tccaaaagca    5460
aaaccatgtg ggttcatgaa gggtgcaata taatctcgag agatctactg tcctagcacc    5520
ttcttctagc ctcattgttg ttttttgggtt gtgatggtgc tgtttaagtt ataagtcctc    5580
ccttggtgct ctgaaattat aattttttgca gccatcaggt taaaaacaaa atcttcaagg    5640
tggcatttga agaaaaatat agagcagctg gtatttagat ttcaaattct taaaacaaga    5700
gatccttctt tccttttttg ggtcttggna tctgcgtttt gattttgtgg caatttctgg    5760
gaatatttcc tactctctaa cgtttgcttt ttgagaattt aaggcgtgct atctgtgtct    5820
tccaggttga agagattgaa aagaaagtcc taagatagtg tgttttttaa ccttcaagaa    5880
ccagataaga acctaacaag aatgcttgaa ttagtacaag attcttaaaa gatattcat    5940 cactcctaag atagtgtgtt ttttaacatt gagttagatt tcatgacgga tatggacctg    6000
taatctttaa aaataggtta tggatgagtt gatttcataa aactagaatg tgggaaattt    6060
```

```
aaagggatat atacttataa aatttccatt accaatataa tctaacacct tttgttgntc      6120
agggaggcta tgattccatg tatcctgttg gcattgggag gaaacctcgt tgaaggttag      6180
tgctgttcca atgacaataa ttttctgtcg tagttgtaga gatatatagc tngactgcaa      6240
atcaagaaca aaatcttctt gaatgacttg acacatttct gctaaaattt tgatatattt      6300
aaattcccat cgcccagcag cataaatttt tgtatcggtg atttaacatg atggcaaatt      6360
gtaatgtcat ttctccccga ttcatttttgt tttctatgtt gggcctttca caaaactttc      6420
aaagcacaag tggaagaagc agaatgctaa ggtttgggta taattatatt tcttgtttgc      6480
tgtcccatca gctcaagttt gtgggtggtt tacctgtcag cttaagcgga ttggtgattt      6540
aactatttct ttagtttagt agaatcatgt naaactaccc aaaagtcctt ttattttcaa      6600
gacagcttac caaataacaa tgtctcactt ngcttgcagg tcctggaagt tcaaaactcg      6660
ggctacggac taccgctgct gttatttttg caaggttggt tttggtgcct cctgcagggg      6720
ttggcatagt catgttagcc gacaagcttg gcttccttcc tccagatgat aaaatgttcc      6780
gatttgttct tcttcttcag cattcgatgc caacatctgt cctctcgagt aagttccaat      6840
cttgacaaac aactaagaac aaacaaacga gtactcaaat tgatcagtaa tcttcacctc      6900
attattcatt tcctgaaatg aaagaattga agcttgttta agtcaaagta gatgtcattt      6960
aaggctttta actcatgaag caaattattt tctgtaggtg ctgtggctac tttgaggggt      7020
tgtggtagag aatctgctgc tattcttttc tgggttcata tatttgccgt catctcaatg      7080
gcagggtggt tcatcctcta cttcaggata ctcttctaaa gaaattgcaa ccttgtgaat      7140
aagtttcata ttccaatact tctccttatt ctttgttaaa tatgggtgtc attcgttact      7200
tgtagagaag accagtatcg tttagaaata gtatttttttt tgtttgagat gattatgtat      7260
cctaaagcta ataagcgaat tagttgcttc aatacggtgg gtgtgaacaa gagatattct      7320
attaatgaat aatccatgct tcgtagatca catggaaaaa gacattatgg agagatgaat      7380
aaagagatta tgttaattgt actttggtat agatttttcct cgatatatgt ttttggaggt      7440
agctgtccat attttatgg atttccgtt taggcaagga aagggacgg agtcgggatt        7500 ttttttcgtt tacgaagatg gagaatgcat ttccttgcccg attgcctctt aataatgttt      7560
tgtaataaat tttaggagtt ctaacctaca taagcttgac ttcaaattta cacacaaata      7620
aggtttaata ttacttaaaa aaataaaaga agttcgtaat aatacaatta taaataaaaa      7680
tgaaaataat ttaggtattt attattcatt ttagtttgga gcatttaata tgagataata      7740
catataattt tatttttttt taattgtatg agatttaatg tgagatagta tatattnatt      7800
tttaatcgta aatgtttgat tnatttcttt tctatatnag tttcattcat tttcattttt      7860
taattgtatt gntatatggc tttctacgtg atctttttct ttttttnntt ctctatgttt      7920
ttatgttgtt nnaattttgt ncagaaannt ttaatggnga ta                        7962
```

<210> SEQ ID NO 15
<211> LENGTH: 32
<212> TYPE: DNA
<213> ORGANISM: Artificial sequence
<220> FEATURE:
<223> OTHER INFORMATION: Sigle strand DNA oligonucleotide

<400> SEQUENCE: 15
ctcgagtcta gaccagtggg ttggtgcaat ta                                    32

<210> SEQ ID NO 16

```
<211> LENGTH: 32
<212> TYPE: DNA
<213> ORGANISM: Artificial sequence
<220> FEATURE:
<223> OTHER INFORMATION: Sigle strand DNA oligonucleotide

<400> SEQUENCE: 16
ggtaccatcg atcggctaac atgactatgc ca                                    32

<210> SEQ ID NO 17
<211> LENGTH: 32
<212> TYPE: DNA
<213> ORGANISM: Artificial sequence
<220> FEATURE:
<223> OTHER INFORMATION: Sigle strand DNA oligonucleotide

<400> SEQUENCE: 17
ctcgagtcta gacagccgac tctagtagtt ca                                    32

<210> SEQ ID NO 18
<211> LENGTH: 32
<212> TYPE: DNA
<213> ORGANISM: Artificial sequence
<220> FEATURE:
<223> OTHER INFORMATION: Sigle strand DNA oligonucleotide

<400> SEQUENCE: 18
ggtaccatcg atccatccag ccatagagat ca                                    32

<210> SEQ ID NO 19
<211> LENGTH: 524
<212> TYPE: DNA
<213> ORGANISM: Artificial sequence
<220> FEATURE:
<223> OTHER INFORMATION: Melon derived amplicons,  Transporter cDNA

<400> SEQUENCE: 19
ccagtgggtt ggtgcaatta tcctgtacac ctatgtttat gcgatgctgg cacctccacc      60
tgagggtaca tttgacatca aagatcaaaa tattccagtt aagaatctgc taaaggataa     120
tacgcctgca catgttccct tgctcattca ggaggtagtc tcaaaatatc cggatgctcc     180
taagaaggaa gagactaagg gcttccttat gtattggttt gacaaattga agctcaagca     240 aattttttcag cctcctatca ttgcttcggt cctagctatg ttattgggtg caactccatt     300
cttaaggcga ttgatcttta ctcctgatgc tccattgttt ttcttcactg atagctgcat     360
aatgctcggg gaggctatga ttccatgtat cctgttggca ttgggaggaa acctcgttga     420
aggtcctgga agttcaaaac tcgggctacg gactaccgct gctgttattt ttgcaaggtt     480
ggttttggtt cctcctgcag gggttggcat agtcatgtta gccg                      524

<210> SEQ ID NO 20
<211> LENGTH: 548
<212> TYPE: DNA
<213> ORGANISM: Artificial sequence
<220> FEATURE:
<223> OTHER INFORMATION: Tomato derived amplicon

<400> SEQUENCE: 20
cagccgactc tagtagttca aataaagaga aggttaaaca gttctttaaa tttctctatg      60
agacactgaa gctcaagcaa cttattcaac ctcccattat agcttctatc atagcgatta     120
tcataggatg tgtgccggtc ctgaaacgcc tcatctttac ttctgatgct ccactttact     180
tcttcactga cagctgttta attcttgggg atgccatgat tccctgcata ttgttggcct     240
```

```
taggaggcaa tctcgttgac gggccaggac ctggaagttc aaaaattggt cttaagacaa      300
ctgttgcgat tgtgtttgca cggttgtgtt tggttcctcc aactggactc agtattgtca      360
tgttagctga taagcttggc ttccttcctg ctgatgataa aatgttcaga ttcgttcttc      420
ttcttcagta ttcaatgccc acatccatac ttgctggtgc ggttgccaac ttgagagggt      480
gtgggaagga ggcagcttca atcttgtttt gggttcatat atttgctgtg atctctatgg      540
ctggatgg                                                               548

<210> SEQ ID NO 21
<211> LENGTH: 32
<212> TYPE: DNA
<213> ORGANISM: Artificial sequence
<220> FEATURE:
<223> OTHER INFORMATION: Sigle strand DNA oligonucleotide

<400> SEQUENCE: 21
ctcgagtcta gacagccgac tctagtagtt ca                                    32

<210> SEQ ID NO 22
<211> LENGTH: 21
<212> TYPE: DNA
<213> ORGANISM: Artificial sequence
<220> FEATURE:
<223> OTHER INFORMATION: Sigle strand DNA oligonucleotide

<400> SEQUENCE: 22
cgtcttacac atcacttgtc a                                                21

<210> SEQ ID NO 23
<211> LENGTH: 28
<212> TYPE: DNA
<213> ORGANISM: Artificial sequence
<220> FEATURE:
<223> OTHER INFORMATION: Sigle strand DNA oligonucleotide

<400> SEQUENCE: 23
tctagaatgg acatggaaag atttctct                                         28

<210> SEQ ID NO 24
<211> LENGTH: 28
<212> TYPE: DNA
<213> ORGANISM: Artificial sequence
<220> FEATURE:
<223> OTHER INFORMATION: Sigle strand DNA oligonucleotide

<400> SEQUENCE: 24
agatctggga attcgatttt agaagagt                                         28

<210> SEQ ID NO 25
<211> LENGTH: 26
<212> TYPE: DNA
<213> ORGANISM: Artificial sequence
<220> FEATURE:
<223> OTHER INFORMATION: Sigle strand DNA oligonucleotide

<400> SEQUENCE: 25
tctagaatgg atagggtgtc gaggat                                           26

<210> SEQ ID NO 26
<211> LENGTH: 28
<212> TYPE: DNA
<213> ORGANISM: Artificial sequence
<220> FEATURE:
```

<223> OTHER INFORMATION: Sigle strand DNA oligonucleotide

<400> SEQUENCE: 26
agatctgcgg gaattcgatt ttaaaaga                                           28

<210> SEQ ID NO 27
<211> LENGTH: 4
<212> TYPE: PRT
<213> ORGANISM: Cucumis melo

<400> SEQUENCE: 27

Leu Ile Val Ala
1

<210> SEQ ID NO 28
<211> LENGTH: 432
<212> TYPE: PRT
<213> ORGANISM: Malus domestica
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (328)..(329)
<223> OTHER INFORMATION: Xaa can be any naturally occurring amino acid

<400> SEQUENCE: 28

Met Glu Arg Val Leu Met Ala Val His Leu Ala Asn Gln Val Xaa Xaa
1               5                   10                  15

Gly Gly Glu Ser Leu Leu Gly Thr Ile Lys Ile Ala Val Leu Pro Ile
            20                  25                  30

Ala Lys Val Phe Thr Val Cys Ala Leu Gly Leu Leu Met Ala Ser Lys
        35                  40                  45

Tyr Val Asn Ile Phe Pro Ala Ser Gly Arg Lys Leu Leu Asn Gly Leu
    50                  55                  60

Val Phe Ser Leu Leu Leu Pro Cys Leu Ile Phe Ser Gln Leu Gly Gln
65                  70                  75                  80

Ala Ile Thr Leu Lys Lys Met Leu Glu Trp Trp Phe Ile Pro Val Asn
                85                  90                  95

Val Val Ile Gly Ser Thr Thr Gly Ser Met Ile Gly Tyr Ile Val Ala
            100                 105                 110

Ser Ile Val Arg Pro Pro Tyr Pro Phe Phe Lys Phe Thr Ile Ile Gln
        115                 120                 125

Ile Gly Ile Gly Asn Ile Gly Asn Val Pro Leu Val Leu Ile Ala Ala
    130                 135                 140

Leu Cys Arg Asp Lys Ser Asn Pro Phe Gly Asp Thr Cys Lys Ala Asp
145                 150                 155                 160

Gly Thr Ala Tyr Ile Ser Phe Gly Gln Trp Val Gly Ala Ile Ile Leu
                165                 170                 175

Tyr Thr Tyr Val Phe Gln Met Leu Ser Pro Pro Glu Gly Thr Phe
            180                 185                 190

Asp Ile Glu Glu Lys Asp Leu Pro Ile Lys Ser Pro Gln Asn Ser Thr
        195                 200                 205

Ser Met Thr Pro Glu Gln Ile Pro Leu Leu Thr Asn Asp Glu Asn Asn
    210                 215                 220

Glu Glu Thr Thr Arg Gln Glu Val Ala Glu Thr Lys Glu Asp Ala
225                 230                 235                 240

Glu Thr Asn Ser Asn Asp Thr Asp Lys Pro Lys Ile Thr Lys Phe Phe

```
            245                 250                 255
Val Phe Ile Tyr Glu Lys Leu Lys Leu Lys Gln Val Leu Gln Pro Pro
                260                 265                 270

Ile Ile Ala Ser Ile Leu Ala Met Val Leu Val Ala Ile Pro Phe Leu
            275                 280                 285

Lys Lys Leu Ile Phe Thr Ser Asp Gly Pro Leu Phe Phe Thr Asp
    290                 295                 300

Ser Cys Ser Ile Leu Gly Glu Ala Met Ile Pro Cys Ile Leu Leu Ala
305                 310                 315                 320

Leu Gly Gly Asn Leu Ile Asp Xaa Xaa Gly Pro Gly Ser Ser Lys Leu
                325                 330                 335

Gly Leu Arg Thr Thr Ala Ala Ile Ile Phe Ala Arg Leu Val Leu Val
                340                 345                 350

Pro Pro Val Gly Leu Gly Ile Val Met Leu Ala Asp Lys Leu Gly Phe
                355                 360                 365

Leu Pro Ala Asn Asp Lys Met Phe Arg Phe Ile Leu Leu Gln Asn
    370                 375                 380

Thr Met Pro Thr Ser Val Leu Ala Gly Ala Val Ala Asn Leu Arg Gly
385                 390                 395                 400

Cys Gly Arg Glu Ala Ala Ala Val Leu Phe Trp Val His Ile Phe Ala
                405                 410                 415

Ile Phe Ser Met Ala Gly Trp Ile Val Leu Tyr Leu Asn Leu Leu Phe
                420                 425                 430

<210> SEQ ID NO 29
<211> LENGTH: 376
<212> TYPE: PRT
<213> ORGANISM: Vitis vinifera

<400> SEQUENCE: 29

Met Cys Phe Leu Gly Phe Leu Met Ala Ser Lys Tyr Val Asn Ile Leu
1               5                   10                  15

Pro Ala Ser Gly Arg Lys Leu Leu Asn Gly Leu Val Phe Ser Leu Leu
                20                  25                  30

Leu Pro Cys Leu Ile Phe Ser Gln Leu Gly Gln Ala Val Thr Leu Gln
            35                  40                  45

Lys Met Ile Glu Trp Trp Phe Ile Pro Thr Asn Val Ile Cys Gly Thr
    50                  55                  60

Ile Ala Gly Ser Leu Ile Gly Leu Val Ala Thr Ile Ile Arg Pro
65                  70                  75                  80

Pro Tyr Pro Phe Phe Lys Phe Thr Val Ile His Val Gly Ile Gly Asn
                85                  90                  95

Ile Gly Asn Val Pro Leu Val Leu Leu Thr Ala Leu Cys Arg Asp Gln
            100                 105                 110

Asn Asn Pro Phe Gly Asp Val Asp Thr Cys Thr Lys Gln Gly Thr Ala
        115                 120                 125

Tyr Ile Ser Phe Gly Gln Trp Val Gly Ala Ile Val Leu Tyr Thr Tyr
    130                 135                 140

Val Phe Gln Met Leu Ala Pro Pro Glu Gly Thr Phe Asp Leu Asp
145                 150                 155                 160

Glu Gln His Leu Pro Ile Lys Gly Cys Pro Lys Asp Gly Ser Pro Glu
                165                 170                 175

Gln Val Pro Leu Ile Thr Gln Glu Val Leu Ser Ser Asp Leu Asn Ala
            180                 185                 190
```

```
Ser Lys Gln Gly Lys Ile Lys Asp Phe Leu Val Tyr Met Tyr Asp Lys
            195                 200                 205

Leu Lys Ile Lys Gln Ile Leu Gln Pro Pro Ile Ala Ser Ile Leu
        210                 215                 220

Ala Leu Ala Ile Gly Ala Ile Pro Phe Leu Lys Lys Leu Ile Phe Thr
225                 230                 235                 240

Pro Asn Ala Pro Leu Phe Phe Phe Thr Asp Ser Leu Ile Ile Leu Gly
                245                 250                 255

Glu Ala Met Ile Pro Cys Ile Leu Ala Leu Gly Gly Asn Leu Val
            260                 265                 270

Asp Gly Pro Gly Ser Ser Lys Leu Gly Leu Arg Thr Thr Thr Ala Ile
        275                 280                 285

Ile Phe Gly Arg Leu Val Leu Val Pro Pro Ala Gly Ile Gly Ile Val
290                 295                 300

Leu Leu Ala Asp Lys Leu Gly Phe Leu Pro Pro Asp Asp Lys Met Phe
305                 310                 315                 320

Arg Phe Val Leu Leu Leu Gln His Ser Met Pro Thr Ser Val Leu Ser
                325                 330                 335

Gly Ala Ile Ala Asn Leu Arg Gly Cys Gly Arg Glu Ser Ala Ala Val
            340                 345                 350

Leu Phe Trp Val His Ile Phe Ala Ile Phe Ser Met Ala Gly Trp Ile
        355                 360                 365

Val Leu Tyr Leu His Ile Leu Phe
            370                 375

<210> SEQ ID NO 30
<211> LENGTH: 1362
<212> TYPE: DNA
<213> ORGANISM: Cucumis sativus

<400> SEQUENCE: 30
atggaaaact tctctcagc catcgtctcg gaagttcaag cgggagggaa ctctctgctt      60
gtcaccatta agattgctgt gttacccata gccaaagttt tcactatgtg ttttctgggt     120
tttcttatgg catctaaata tgtcaacatc ttgcctgcaa gtggaaggaa gcttttgaat     180
gggttggtct tttcgctttt gcttccatgt ttaatattct ctcagctcgg gcaagctatt     240
actctcgaga aaatgcttaa atggtggttt attccggcaa atgttgttct ggcttcgata     300
tcaggttccc taattggatt aattgttgca tcaattgttc gtcctccata cccattcttc     360
aagttcacga ttgtacaaat tggaattggg acattggaa atgtgcctct cgttctcatt     420
gcagctctat gtagagatga tatgaatcct tttggtgatg aagagaagtg tagcactgat     480
gggattgctt atatttcata tggccagtgg gttggtgcaa ttatcctcta cacctatgtt     540
tatgcgatgt tggcacctcc acctgagggt acatttgaca tcaaagatca aatatttca      600
gttaagaacc ttctaaagga taatacacct gcgcatgttc ccttgctcat tcaggaggta     660
ccttcaacat atccggatgc tcctaagaag gaagagaagt atgatatgga atatgaaaaa     720
tgtaataacg acaacaaaac ctccacctat ttccacaacg gtataatact tccactttg      780
ggcatatttc ctcatagcct tacttttgga atcacccaaa agactaaggg ctttcttatt     840
tattggtttg acaaattgaa gctcaagcaa atgtttcagc ctcctattgt tgcttcggtc     900
ctagctatgt tattgggtgc aactccattc ttaaggcggt tgattttac tcctgatgct     960
ccattgtttt tcttcactga tagctgcata atgctcgggg aggctatgat tccatgcatc    1020
ctgttggcat tgggaggaaa cctcgttgaa ggtcctggaa gttcaaaact tgggctacgg    1080
```

-continued

| | |
|---|---|
| actaccgctg ctattatttt tgcacggttg gttttggtgc ctcctgcagg acttggcata | 1140 |
| gtcatgttag ctgacaagct tggcttcctt cctccagatg ataaaatgtt ccgattcgtt | 1200 |
| cttcttcttc agcattcgat gccaacgtct gtcctctcaa gtgctgtggc tactttgagg | 1260 |
| ggttgtggta aagattctgc tgctattctt ttctgggttc atatattttc tgtcatctca | 1320 |
| atggcagggt ggttcatcct ctatttcagg atactcttct aa | 1362 |

<210> SEQ ID NO 31
<211> LENGTH: 1276
<212> TYPE: DNA
<213> ORGANISM: Lycopersicon esculentum

<400> SEQUENCE: 31

| | |
|---|---|
| atggataggg tgtcgaggat tcttttagt gttctgacag aaccgcaacg aggaggacag | 60 |
| tctttcatca cgtcgattaa gattgctgtt ttaccgattg cgaaagtgtt tacactatgc | 120 |
| ttcttgggat ttttgatggc ctccaagtat gtcaatattc ttccagcaaa tggacggaag | 180 |
| cttttaaatg ggttggtgtt ttcacttttg ctgccatgct tgatattctc tcaacttgga | 240 |
| caagccatta cgtatgagaa attgcttcag tggtggttca tccctgttaa cattgttttg | 300 |
| gccaccatat ttggttctat tattggttta attgttgcta cgatagtccg tccgccatac | 360 |
| ccttatttca agtttaccat tatacagatt ggcattggga acataggaaa tgttccactt | 420 |
| gttctgatag ctgcgttatg tcgtgaccca tcaaatcctt ttggtgactc tgagatatgt | 480 |
| gcgcgagatg gaaatgcata catctctttt ggacagtggg ttggtgcaat tatcctctac | 540 |
| acctttgtat tccaaatgct ctcacctcct cctgaaggtt ccttcgatgt tgaagatgca | 600 |
| aaccttccta tcaaggttcc taacaaagaa agattaccga gtcatccatc aggtagttct | 660 |
| gcagagcaag ttccattact tgcaacaaat gttgcaccag ccgactctag tagttcaaat | 720 |
| aaagaaaagg ttaaacagtt ctttaaattt ctctatgaga cactgaagct caagcaactt | 780 |
| attcaacctc ccattatagc ttctatcata gcgattatca taggatgtgt gccggtcctg | 840 |
| aaacgcctca tctttacttc tgatgctcca ctttacttct tcactgacag ctgtttaatt | 900 |
| cttggggatg ccatgattcc ctgcatattg ttggccttag gaggcaatct cgttgacggg | 960 |
| ccaggacctg gaagttcaaa aattggtctt aagacaactg ttgcgattgt gtttgcaccg | 1020 |
| gttgtgtttg gttcctccaa ctggactcag tattgtcatg ttagctgata agcttggctt | 1080 |
| ccttcctgct gatgataaaa tgttcagatt cgttcttctt cttcagtatt caatgcccac | 1140 |
| atccatactt gctggtgcgg ttgccaactt gagagggtgt gggaaggagg cagcttcaat | 1200 |
| cttgttttgg gttcatatat ttgctgtgat ctctatggct ggatggatca tcctctacct | 1260 |
| caacatactc ttttaa | 1276 |

<210> SEQ ID NO 32
<211> LENGTH: 1296
<212> TYPE: DNA
<213> ORGANISM: Arabidopsis thaliana

<400> SEQUENCE: 32

| | |
|---|---|
| atgattgctc ggatccttgc cgccttagcc gattccatgg agatgccggt ggctgccggt | 60 |
| ggtggatcag tgctcggtac catcaaaatc gctgtgatgc caattgcaaa ggtattcacc | 120 |
| atgtgcttct gggtcttcct catggcctcc aagtacgtta acatcttgcc tccctctggc | 180 |
| cgcaaaactct tgaacggggtt ggtcttctcg cttttgcttc cctgcttgat cttttcccag | 240 |

```
ctcggacaag ccgtcactct ccaaaaaatg cttcagtggt ggttcattcc cgttaacgtc      300
gttcttggca ccatctctgg ctccataatc ggtttcatcg ttgcttccat cgttcgtccg      360
ccttacccct acttcaagtt tacaatcata caaattggag ttggcaacat tggcaatgtg      420
cctcttgttt tacttgcggc tctttgtagg gacacttcca accctttttgg tgactccgaa     480 aaatgtagca ttgatggcac tgcttatatc tcctttggtc aatgggttgg tgccatcatc      540
ctctatacat atgtgtacca gatgtttgct cctcctccag aagggtttga tgctgaagaa      600
gaaaatcttg ctttaaaaac ccttccagta gatgctgctc cagagcaagt ccccttgctt      660
actcagaatt ttcccaagga cttttcgccg actcaagatc ttttgcctgt acagagcacc      720
gaacctaggg gaagaggggt ttcaaggaaa ggcaagattg cacagatctt tgttttcctc      780
tatgagaagc tgaaactgaa gcaaattgtc cagcctgcaa ttgttgcttc gatccttgcc      840
atgatactcg gagcaatacc tttcacaaag aagttgatat tcacaaatgg tgcacctcta      900
ttcttcttca cagacagctg catgattctt ggggacgcga tgataccgtg tatcttactg      960
gcactggggg gaaatctcat taacggacca ggaagttcaa acttggtttt caagacaaca     1020
gcagctatta taattggacg gttggtgtta gtgccaccag taggactagg aatcgtgaca     1080
gtagcagaca aacttgggtt ccttcctgct gatgataaga tgttccgatt tgtgttactc     1140
cttcagcaca caatgcctac atcagtgctc tcaggagctg ttgccaacct tagaggctgt     1200
ggaagggaat cagctgctgt gctcttctgg gtccacattt tcgccatctt ctcaatggct     1260
ggatggatgg tactctacat taacatactc ttctga                              1296

<210> SEQ ID NO 33
<211> LENGTH: 1131
<212> TYPE: DNA
<213> ORGANISM: Vitis vinifera

<400> SEQUENCE: 33
atgtgctttc tgggctttct gatggcttcc aagtatgtca atattttgcc tgccagtgga       60
aggaaacttt tgaatgggtt ggttttttca cttttgcttc cgtgtttgat attctctcaa      120
ctgggtcaag ccgttacttt gcagaaaatg attgagtggt ggtttattcc tactaatgtt      180
atttgcggca ccatagcagg gtcgctaata gggttagtcg tagctaccat tattcgtccg      240
ccatacccat tctttaagtt tacagttata catgttggaa tcgggaacat cgggaatgtg      300
cctcttgtcc tgcttacagc tttatgcaga gaccagaaca accctttttgg tgatgtagac     360 acttgcacca aacaagggac tgcctatatc tcattcggcc aatgggttgg tgcaattgtt      420
ttgtacacct atgtatttca aatgcttgca cctcctcctg aaggtacctt tgaccttgat      480
gaacaacatc ttcccatcaa gggctgtcca aaggatggct cccctgagca agttccgtta      540
attacacagg aggttttatc atctgatcta aatgcctcaa acaagggaa gattaaagat      600 tttttggttt atatgtatga taaattgaag atcaagcaaa ttcttcaacc gcctattatt      660
gcttctatcc tagcattggc aattggtgca attccatttt tgaagaagct gatctttaca      720
cccaatgctc cgcttttctt cttcactgac agcctcatta ttcttgggga ggccatgatt      780
ccatgcattt tgttggcatt gggaggcaac ttggtcgatg gaccaggaag ttcaaaactt      840
ggtctacgga cgactactgc tattattttc gggcggttgg ttttggttcc tcctgctgga      900
attggcatag tcttgctggc tgataagctt ggctttctcc cccctgatga caagatgttc      960
cgatttgtcc tcctcctcca acattccatg cccacatctg tgcttctgg tgctatcgcc     1020 aatttaagag ggtgcggaag agagtcagct gctgtcctct tctgggttca tatctttgca     1080
```

```
atcttctcca tggctggatg gatcgttctt tatctccata tcctcttctg a          1131
```

<210> SEQ ID NO 34
<211> LENGTH: 1287
<212> TYPE: DNA
<213> ORGANISM: Malus domestica

<400> SEQUENCE: 34

```
atggagaggg ttttgatggc ggtgcatctg gcgaatcaag tcggaggggga atcgttactt    60
gggacgatca agatcgcggt gcttcccata gcaaaggttt ttactgtgtg cgccttgggg   120
cttctaatgg cttccaagta tgtcaacatc ttcccagcca gtggaagaaa actcttgaat   180
gggttggtct tctcgctatt gcttccatgt tgatattttt ctcagcttgg acaagccatc   240
accctaaaga aaatgctcga gtggtggttt attcccgtga atgtcgtgat ggtagcact    300
acaggctcca tgataggtta tatcgttgca tcaattgtcc gaccaccgta ccccttcttc   360
aagtttacaa ttatacagat tggaatagga acatcggga atgtgccact ggttctaatt   420
gcagctttgt gtagagacaa atcaaaccct ttcggtgata cgtgtaaagc agatgggact   480
gcctatattt catttggcca gtgggttggt gcaatcattc tatacacgta tgtatttcaa   540
atgctgtccc cccctcctga aggtaccttt gacattgagg agaaagatct cccaatcaaa   600
agccctcaaa acagcacgag catgacacct gaacaaattc cgttgcttac aaatgatgaa   660
aataatgaag agacaacacg tcaagaagag gttgcagaaa ctaaagagga tgcagaaact   720
aactcaaatg atacagataa acctaagatt acaaagttct tcgtatttat atacgaaaag   780
ttgaagctca aacaagttct ccaaccacct ataatagctt ctatcctggc catggtactt   840
gtagcgatac cattttaaa gaaattgatc tttacatctg atggtccact tttcttcttc    900
accgatagct gcagtatcct tggggaagcc atgattccgt gcattctgtt ggcattaggt   960
ggcaacctta ttgatggtcc gggaagttca aaacttggtc tacggacaac tgctgcaatt  1020
atatttgcac gactagtctt ggtgccccccg gtaggacttg gcattgtaat gttagccgat  1080
aagcttggct tcctcctgc caatgacaaa atgtttcgat ttatcctgct gctccagaac  1140
acaatgccta catctgtcct tgctggtgct gttgcaaatt taagaggctg tggtagagag  1200
gcagctgccg tcctgttctg ggtgcacata ttcgccatct tctccatggc cgggtggatc  1260
gtcttgtacc tcaacctact cttctga                                      1287
```

<210> SEQ ID NO 35
<211> LENGTH: 1245
<212> TYPE: DNA
<213> ORGANISM: Populus trichocarpa

<400> SEQUENCE: 35

```
atggagagat ttttattagc tgtggacacc atgggagcaa atcaggtggg aggaggacag    60
actctcttgg gcaccatcaa aattgctgtt ctgcccattg ccaagttttt taccatgtgc   120
ttcttgggat ttctcatggc ctccaagtat gttaacatct gcctgctag tggaaggaaa   180
ctcttaaatg ggttggtgtt ttcacttttg cttccttgtt tgatattttc tcaacttgga   240
caagctgtca ctttacagaa aatgttggag tggtggttta ttcccgtgaa tgttgttctt   300
agctccatct gtggctcgct aataggtttt attgttgcat ccattgtccg gccaccttac   360
ccattcttca aattttcaat tgtacaaatc ggaattggga atattgggaa tgtgccactt   420
gtcttgattg cagctttatg tagagataca tccaaccctt ttggtgactc ggaaaaatgt   480
```

```
agcacagatg ggactgctta catctcgttt ggccagtggg ttggtgcaat cattctatac    540
acatatgtat ttaacatgtt ggcacctcca ccggaaggta cctttgatat tgatgaaccg    600
aatcttccca tcaagaagcc agccaaagat gctcccatgg agcaagtccc cttgcttgcc    660
caggaggagg caccggcaga accagatgct ccaaagagag gaagatcaa acagattctt     720 gtctttctct atgacaagtt gaagctcaag caaattcttc agcccctat cattgcttcg     780 atcctagcta tgttccttgg tgcagtaccg ttcttgaagc aattgatctt tacaactgat    840
tctccccttt tcttttcac tgacagctgc aatattcttg gggaggccat gattccatgc     900
attttgttgg cgctaggagg caatctcgtt gatggacctg gaagttctaa acttgggttt    960
cggacaactg ctgctattat ttttggtcgg ttggttttgg tgccacctac tggacttggc   1020
attgttatgt tggctgataa gcttggcttc cttcctgctg gtgataagat gttccggttt   1080
gttctgcttc tgcagcatac gatgcctaca tctgtccttt ctggtgctgt ggccaaccta   1140
agaggatgtg aagagaagc tgctgctgtc ctattctggg ttcatatttt tgctattttc    1200
tcaatggctg gatggattgt cctttatctc aacatactct tctga                   1245

<210> SEQ ID NO 36
<211> LENGTH: 506
<212> TYPE: DNA
<213> ORGANISM: Petunia hybrida

<400> SEQUENCE: 36
caactgggct tagcatagtt atgttagctg ataagcttgg cttccttccc cctgatgata     60
aaatgttcag atttgtttta cttctgcagc atacaatgcc cacatccgta ctttctggtg    120
ctgttgccaa cttgagaggc tgtgggaagg aagcagcttc tgtcttgttc tgggttcata    180
tctttgctat gttctctatg ccggatgga tcaccctcta tctcaagatt ctcttttgag     240
ttagaatcag cggtgttgca gccaagcaaa ggatctcgat ggagaaattt tgttcctctt    300
ccaagatcgt gcctgtctgt ccaaagttgc ttttggttc aattccaagc cattgttgtc     360
tatagtacaa aacagatgta ttgattatgt aggatgacca actacaacta taaataattg    420
ttgatagtga agaattgatc ttattgcttg ttcaaactta aaaaaaaaaa aaaccaaaaa    480
actacgacaa gtgagtagac aggacc                                         506

<210> SEQ ID NO 37
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 37
ctgggcttag catagttatg t                                               21

<210> SEQ ID NO 38
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 38
ttgagataga gggtgatcca t                                               21

<210> SEQ ID NO 39
<211> LENGTH: 223
```

```
<210> SEQ ID NO 39
<211> LENGTH: 223
<212> TYPE: DNA
<213> ORGANISM: Artificial sequence
<220> FEATURE:
<223> OTHER INFORMATION: Petunia derived amplicon

<400> SEQUENCE: 39
ctgggcttag catagttatg ttagctgata agcttggctt ccttcccct gatgataaaa      60 tgttcagatt tgttttactt ctgcagcata caatgcccac atccgtactt tctggtgctg    120
ttgccaactt gagaggctgt gggaaggaag cagcttctgt cttgttctgg gttcatatct    180
ttgctatgtt ctctatggcc ggatggatca ccctctatct caa                     223

<210> SEQ ID NO 40
<211> LENGTH: 50
<212> TYPE: DNA
<213> ORGANISM: Artificial sequence
<220> FEATURE:
<223> OTHER INFORMATION: Single strand DNA oligonucleotide

<400> SEQUENCE: 40
ggggacaagt ttgtacaaaa aagcaggctc tgggcttagc atagttatgt                50

<210> SEQ ID NO 41
<211> LENGTH: 50
<212> TYPE: DNA
<213> ORGANISM: Artificial sequence
<220> FEATURE:
<223> OTHER INFORMATION: Single strand DNA oligonucleotide

<400> SEQUENCE: 41
ggggaccact ttgtacaaga aagctgggtt tgagatagag ggtgatccat                50

<210> SEQ ID NO 42
<211> LENGTH: 12
<212> TYPE: DNA
<213> ORGANISM: Cucumis melo
<220> FEATURE:
<221> NAME/KEY: misc_feature
<223> OTHER INFORMATION: Duplicated in non-sour melon

<400> SEQUENCE: 42
ttaattgttg ca                                                         12
```

ISOLATED POLYNUCLEOTIDES AND METHODS AND PLANTS USING SAME FOR REGULATING PLANT ACIDITY

RELATED APPLICATIONS

This application is a National Phase of PCT Patent Application No. PCT/IL2011/000554 having International filing date of Jul. 12, 2011, which claims the benefit of priority under 35 USC §119(e) of U.S. Provisional Patent Application No. 61/363,291 filed on Jul. 12, 2010. The contents of the above applications are all incorporated by reference as if fully set forth herein in their entirety.

FIELD AND BACKGROUND OF THE INVENTION

The present invention, in some embodiments thereof, relates to novel isolated polynucleotides and polypeptides which control acidity of a plant, and, more particularly, but not exclusively, to methods of using same for modulating acidity of plants, and for marker-assisting breeding of plants having desired acidity.

It has long been recognized that the acid level of fruits is an important determinant of quality, together with the sugar and volatile components. In many cases quality is actually determined by the sugar to acid ratio, as for example for grapes and citrus. Most fruit develop a fruit acid content in the acidic range, which contributes to taste: the pH values of expressed fruit juice is generally in the acidic range of 4-5 and certain fruit, such as lemons or ripe cucumbers can reach even higher levels of acidity with pH levels below 3.

The sweet melons (Cucumis melo) are fairly unique among fleshy fruit in that they have an unusually low level of acidity, and the values for all cultivated sweet melons are in the near neutral range of about 6-7. Accordingly, sweet melons have an unusually low organic acid content. Citric acid, the major organic acid in sweet melon cultivars studied to date, contributes only about 0.2% of the fruit fresh weight. This is in contrast to ripe fruit such as strawberry, pineapple or apricot, which can contain about 5 times the amount of organic acid.

One of the useful characteristics of Cucumis melo is that there exist primitive varieties within the species that have acidic fruit with nearly 1% organic acid concentration. The trait has been studied and the inheritance determined to be controlled by a single major locus, termed So (Sour) or pH (Danin-Poleg et al., 2002, Euphytica, 125: 373-384; Burger et al., 2003, J. Amer. Soc. Hort. Sci. 128: 537-540). Sour, low pH fruit, is dominant over non-sour fruit and the evolution under domestication of the sweet melons was apparently accompanied by selection for the non-sour recessive mutant soso (Burger et al., 2003, Supra). All of the cultivated sweet, high sugar melon varieties, irrespective of the fruit group (cantaloupe, honeydew, galia, charantais) have a low acidic content while all the acidic primitive cultivated and non-cultivated varieties have low sugar content. However, there is a global need in the markets for fruit having sweet and sour taste.

Despite the importance of organic acid accumulation and metabolism in fruit, little is known regarding the pathways and their control of the large temporal and genetic differences. The complexity of the pathway, its multi-components and multi-compartmentation of the pathway makes the study of individual enzymes Sisyphean in its approach.

There also exists genetic variability for acid levels in other species, such as citrus, tomato, grape and peach varieties, wherein changes in organic acids and sugars during early stages of development of acidic and acidless citrus fruit have been described.

U.S. Pat. No. 5,476,998 describes a sour tasting Cucumis melo F1 hybrid melon, derived from the breeding line produced from a plant grown from a seed having dominant allele that produces flesh with a mean pH value below 5.4 and at least one dominant allele for expression of juicy character in the flesh.

Boualem A., et al. 2008 (Science 231: 836-838) describe a mutation in ethylene biosynthesis enzyme which leads to andromonoecy in melons.

Harel-Beja et al. 2010 (Theor. Appl. Genet, 121: 511-533) describe a genetic map of melon highly enriched with fruit quality Quantitative trait loci (QTLs) and expressed sequence tag (EST) markers including sugar and carotenoid metabolism genes.

In the flower industry, the flower color is one of the most important traits of flowers. Although cultivars of various colors have been bred using conventional breeding by crossing, it is rare that a single plant species has cultivars of all colors. The main components of flower color are a group of flavonoid compounds termed anthocyanins, the color of which depends partly on their structures. In addition, since anthocyanins are present in the vacuole of the cell, the pH of vacuoles has a great impact on the color of flowers. It is thought that the vacuole of plant cells is regulated by vacuolar proton-transporting ATPase and vacuolar proton-transporting pyrophosphatase, but the mechanism of how these proton pumps are involved in the color of flowers has not been elucidated. In addition, a sodium ion-proton antiporter exits in plant vacuoles and transports sodium ions into vacuoles, depending on the proton concentration gradient between the outside and the inside of vacuoles, whereupon protons are transported outside of vacuoles resulting in a reduced proton concentration gradient. It is believed that if the pH of vacuoles could be modified, e.g., raised, flower color could be turned blue. Representative plant species that lack blue colors include roses, chrysanthemums, carnations, gerberas and the like, which are very important cut flowers.

U.S. Pat. No. 6,803,500 discloses genes encoding proteins regulating the pH of vacuoles.

Quattrocchio F., 2006 (The Plant Cell, Vol. 18, 1274-1291) describe the identification of PH4 of Petunia, an R2R3MYB Protein, that activates vacuolar acidification through interactions with basic-helix-loop-helix transcription factors of the anthocyanin pathway.

The pH of fruit affects the post harvest quality of the fruit. Thus, reduction of pH may have positive effects on fruit storage and on inhibition of pathogenic attacks, for example in tomato paste products [Clayero, M. R. S. 2001, Acta Horticulturae, 542: 75-81]. In addition, the chemical control of enzymatic blackening or browning of cut fruit and vegetable requires the inhibition of PPO activity by adjustment of pH [Ferrar, P. H., Walker, J. R. L. Inhibition of diphenol oxidases—a comparative study, J. Food Biochem. 1996, 20, 15-30; Walker, J. R. L.; Ferrar, P. H. Diphenol oxidases, enzyme-catalyzed browning and plant disease resistance, Biotechnol. Genetic Eng. ReV. 1998, 15, 457-498].

The pH of roots and of the surrounding soil impacts on nutrient uptake from the soil. For example, Aluminum uptake is strongly increased at pH below 5 and leads to aluminum toxicity of the plant [Panda S K, et al. Aluminum stress signaling in plants. Plant Signal Behav. 2009 4:592-7]. Furthermore, with decreased soil pH, dramatic increases in heavy metal desorption from soil constituents and dissolution in soil solution were observed for Cd, Pb and Zn. In addition, a negative correlation between soil pH and heavy metal mobility and availability to plants has been well documented in numerous studies (Zeng F, 2011 The influence of pH and organic matter content in paddy soil on heavy metal availability and their uptake by rice plants. Environ Pollut. 159:84-9).

Modifying rhizosphere pH can also positively contribute to the uptake of non-toxic necessary elements making certain nutrients available to the plant [Haynes R J, and Swift R S, 1985. Effects of soil acidification on the chemical extractability of Fe, Mn, Zn and Cu and the growth and micronutrient uptake of high bush blueberry plants. Plant Soil 84, 201-212; Silber, A., Ben Yones, L. and Dori, I. (2004). Rhizosphere pH as a result of nitrogen level and NH4/NO3 ratio and its effect on Zn availability and on growth of rice flower (*Ozothamnus diosmifolius*). Plant Soil, 262, 205-213].

Additional background art includes Peters J. L. et al., 2003 (Trends in Plant Science, 8: 484-491); Henikoff S., et al. 2004 (TILLING. Traditional Mutagenesis Meets Functional Genomics. Plant Physiology, 135: 630-636).

SUMMARY OF THE INVENTION

According to an aspect of some embodiments of the present invention there is provided an isolated polynucleotide comprising a nucleic acid sequence encoding a polypeptide having at least 60% identity to a polypeptide selected from the group consisting of SEQ ID NO:2, 4, 5, 6, 8, 9 10, 28 and 29, wherein the polypeptide modulates acidity of a plant.

According to an aspect of some embodiments of the present invention there is provided an isolated polynucleotide capable of down-regulating expression of the isolated polynucleotide of some embodiments of the invention in a host cell.

According to an aspect of some embodiments of the present invention there is provided a nucleic acid construct comprising the isolated polynucleotide of some embodiments of the invention and a cis acting regulatory element for directing transcription of the nucleic acid sequence in a host cell.

According to an aspect of some embodiments of the present invention there is provided an isolated polynucleotide primer pair capable of specifically amplifying the isolated polynucleotide of some embodiments of the invention.

According to an aspect of some embodiments of the present invention there is provided a plant cell exogenously expressing the isolated polynucleotide of some embodiments of the invention, or the nucleic acid construct of some embodiments of the invention.

According to an aspect of some embodiments of the present invention there is provided an isolated polypeptide comprising an amino acid sequence having at least 60% identity to a polypeptide selected from the group consisting of SEQ ID NO:2, 4, 5, 6, 8, 9 10, 28 and 29, wherein the polypeptide is capable of modulating acidity of a plant.

According to an aspect of some embodiments of the present invention there is provided a plant cell exogenously expressing the polypeptide of some embodiments of the invention.

According to an aspect of some embodiments of the present invention there is provided a plant comprising the nucleic acid construct of some embodiments of the invention or the plant cell of some embodiments of the invention.

According to an aspect of some embodiments of the present invention there is provided a food or feed comprising the plant of some embodiments of the invention or a part thereof.

According to an aspect of some embodiments of the present invention there is provided a method of generating a transgenic plant, comprising expressing within the plant the isolated polynucleotide of some embodiments of the invention, or the nucleic acid construct of some embodiments of the invention, thereby generating the transgenic plant.

According to an aspect of some embodiments of the present invention there is provided a method of regulating acidity of a plant, comprising modulating an expression level of a polypeptide having at least 60% identity to a polypeptide selected from the group consisting of SEQ ID NO:2, 4, 5, 6, 8, 9 10, 28 and 29, thereby regulating the acidity of the plant.

According to an aspect of some embodiments of the present invention there is provided a method of affecting post harvest fruit storage, comprising regulating acidity of the fruit according to the method of some embodiments of the invention, wherein when the regulating comprises increasing acidity of the fruit then the post harvest fruit storage is increased, and wherein when the regulating comprises decreasing acidity of the fruit then the post harvest fruit storage is decreased, thereby affecting the post harvest fruit storage.

According to an aspect of some embodiments of the present invention there is provided a method of affecting nutrient uptake of a plant, comprising regulating acidity of the roots according to the method of some embodiments of the invention, wherein when the regulating comprises increasing acidity of the roots then the nutrient uptake is increased, and wherein when the regulating comprises decreasing acidity of the roots then the nutrient uptake is decreased or unchanged, thereby affecting the nutrient uptake of the plant.

According to an aspect of some embodiments of the present invention there is provided a method of selecting a melon plant for breeding, comprising determining in a tissue of the plant a presence or an absence of a LIVA (SEQ ID NO:27) duplication at amino acids 107-110 of SEQ ID NO:4, wherein the presence of the LIVA duplication indicates that a fruit of the melon plant is expected to be non-sour, and wherein the absence of the LIVA duplication indicates that a fruit of the melon plant is expected to be sour, thereby selecting the melon plant for breeding.

According to an aspect of some embodiments of the present invention there is provided a method of identifying a nucleic acid variation associated with decreased acidity of a plant, comprising: identifying in at least one plant of a plurality of plants a loss-of-function mutation in a polypeptide having at least 60% identity to a polypeptide selected from the group consisting of SEQ ID NO:2, 4, 5, 6, 8, 9 10, 28 and 29, wherein the polypeptide modulates acidity of a plant, thereby identifying the nucleic acid variation associated with decreased acidity of the plant.

According to an aspect of some embodiments of the present invention there is provided a method of affecting flower petal color, comprising regulating acidity of the flower petal according to the method of some embodiments of the invention, to thereby change the flower petal color.

According to some embodiments of the invention, wherein when the regulating comprises increasing acidity of the flower petal then the flower petal color is more red than in a non-transgenic or in a non-transformed plant of the same species under identical growth conditions, and wherein when the regulating comprises decreasing acidity of the flower petal then the flower petal color is more blue than in a non-transgenic or in a non-transformed plant of the same species under identical growth conditions.

According to some embodiments of the invention, the polynucleotide is at least 60% identical to a polynucleotide selected from the group consisting of SEQ ID NOs: 1, 3, 30, 31, 32, 33, 34 and 35.

According to some embodiments of the invention, the regulating comprises increasing acidity of the plant, and the modulating comprises up-regulating the expression level of the polypeptide.

According to some embodiments of the invention, the regulating comprises decreasing acidity of the plant, and the modulating comprises down-regulating the expression level of the polypeptide.

According to some embodiments of the invention, the up-regulating is effected by transforming a plant cell of the plant with a polynucleotide encoding the polypeptide.

According to some embodiments of the invention, the down-regulating is effected by transforming a plant cell of the plant with a polynucleotide capable of downregulating expression level of the polypeptide.

According to some embodiments of the invention, the plant comprises a fruit.

According to some embodiments of the invention, the fruit is a ripe fruit.

According to some embodiments of the invention, the fruit is of a plant family selected from the group consisting of: Solanaceae, Cucurbitaceae, Rutaceae, Rosaceae, and Vitaceae.

According to some embodiments of the invention, the modulating the expression level is effected using a fruit specific promoter.

According to some embodiments of the invention, the modulating is effected using a developmental-specific promoter for modulating expression of the polypeptide before ripening of the fruit.

According to some embodiments of the invention, the plant comprises a non-fruit portion.

According to some embodiments of the invention, the non-fruit portion comprises roots.

According to some embodiments of the invention, the loss-of-function mutation is identified on DNA of the plurality of plants.

According to some embodiments of the invention, the loss-of-function mutation is selected from the group consisting of a nonsense mutation, a frameshift mutation, an insertion, a duplication mutation or a deletion mutation.

According to some embodiments of the invention, the non-fruit portion comprises flower petal.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D depict the mRNA and amino acid sequences of the pH gene, from two varieties of melon, characterized by low and high pH, respectively. FIG. 1A—mRNA sequence of pH gene from sour melon beginning with ATG and ending with stop codon TAA (SEQ ID NO:1); FIG. 1B—Translated protein sequence of membrane transporter from sour melon (SEQ ID NO:2); FIG. 1C—mRNA sequence of pH gene from non-sour melon beginning with ATG and ending with stop codon TAA (SEQ ID NO:3; the TTAATT GTTGCA (SEQ ID NO: 42) sequence which is subject to duplication is shown in yellow, and the duplicated sequence is shown in bold); FIG. 1D—protein sequence of membrane transporter from non-sour melon [SEQ ID NO:4; the original LIVA sequence which is subject to duplication is shown in yellow, and the duplicated sequence is shown in bold].

FIG. 1E depicts alignment between amino acid sequences of sour (SEQ ID NO:2) and non sour (SEQ ID NO:4) melon varieties.

FIGS. 2A-F depict the amino acid sequences of orthologous pH genes from tomato (FIG. 2A, Tomato TC200226, SEQ ID NO:5), cucumber (FIG. 2B, Cucumber Csa01116, SEQ ID NO:6), sweet melon (FIG. 2C, SEQ ID NO:7), apple (FIG. 2D, apple TC80539, SEQ ID NO:8), poplar (FIG. 2E, Poplar EEF05451, SEQ ID NO:9) and *Arabidopsis* (FIG. 2F, *Arabidopsis* NP_195819, SEQ ID NO:10). Sequences are from the NCBI [World Wide Web (dot) ncbi (dot) nlm (dot) nih (dot) gov/] and TIGR [Hypertext Transfer Protocol://compbio (dot) dfci (dot) Harvard (dot) edu/tgi/plant (dot) html] databases and accession numbers are listed following the plant name.

FIG. 3 depicts the sequence alignment of the orthologous pH genes from sweet melon, sour melon, apple, tomato, cucumber, poplar and *Arabidopsis*. Clustal alignment was carried out by the Clustal 2W program at Hypertext Transfer Protocol://World Wide Web (dot) ebi (dot) ac (dot) uk/Tools/. CLUSTAL 2.0.12 multiple sequence alignment—The mutation/duplication in the sweet, non-sour melon is underlined in bold.

FIGS. 4A-D depict protein modeling (TMhMM) [Hypertext Transfer Protocol://World Wide Web (dot) cbs (dot) dtu (dot) dk/services/TMHMM-2.0/] of the transmembrane domains of the protein from the sour melon (FIGS. 4A-B) and the non-sour melon (FIGS. 4C-D) containing the four amino acid mutation/duplication. FIG. 4A—Summary of protein modeling sour melon; FIG. 4B—schematic presentation of the protein modeling sour melon, TMHMM posterior probabilities for Sequence. Red=transmembrane; blue=inside; pink—outside. FIG. 4C-Summary of protein modeling non-sour melon; FIG. 5D—schematic presentation of the protein modeling non-sour melon. TMHMM posterior probabilities for Sequence. Red=transmembrane; blue=inside; pink—outside. Note that the LIVA duplication mutation occurs at the third transmembrane domain.

Figure 5:
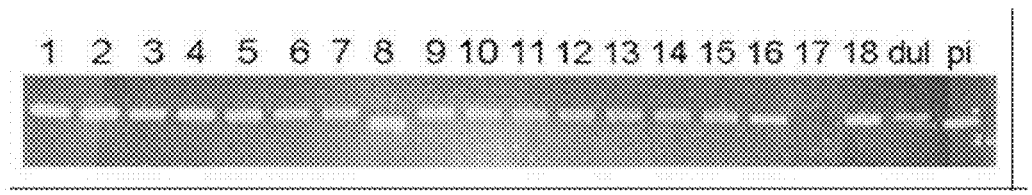

FIG. 5 is a gel image depicting DNA-PCR for genotyping plants of 20 representative melon varieties for the presence or absence of the LIVA duplication mutation. Leaf DNA from melon varieties were subjected to PCR using primers specific for the duplication mutation (SEQ ID NO:12 and 13). For control, the cv. Dulce (dul) and the breeding line PI414723 (pi) parental lines were included in the analysis and are presented in the two most right lanes, wherein the Dulce line includes the LIVA duplication and exhibits a higher molecular weight band (137 base-pairs (bp)) and the PI414723 does not have the LIVA duplication and exhibits a lower molecular weight band (125 bp). Lanes correspond to the following melon varieties: 1—PSR; 2—TVT; 3—HBJ; 4—PI 157080; 5—INB; 6—PDS; 7—ESL; 8—PI 157071; 9—KRY; 10—CHT; 11—CHF; 12—DUD2; 13-DUD3; 14—MAK; 15—OGE; 16—PH406; 17—Blank lane; 18—Rochet; 19—Dulce control; 20-PI414723 control. Genotyping results are summarized in Table 5 in Example 5 of the Examples section which follows.

Figure 6:
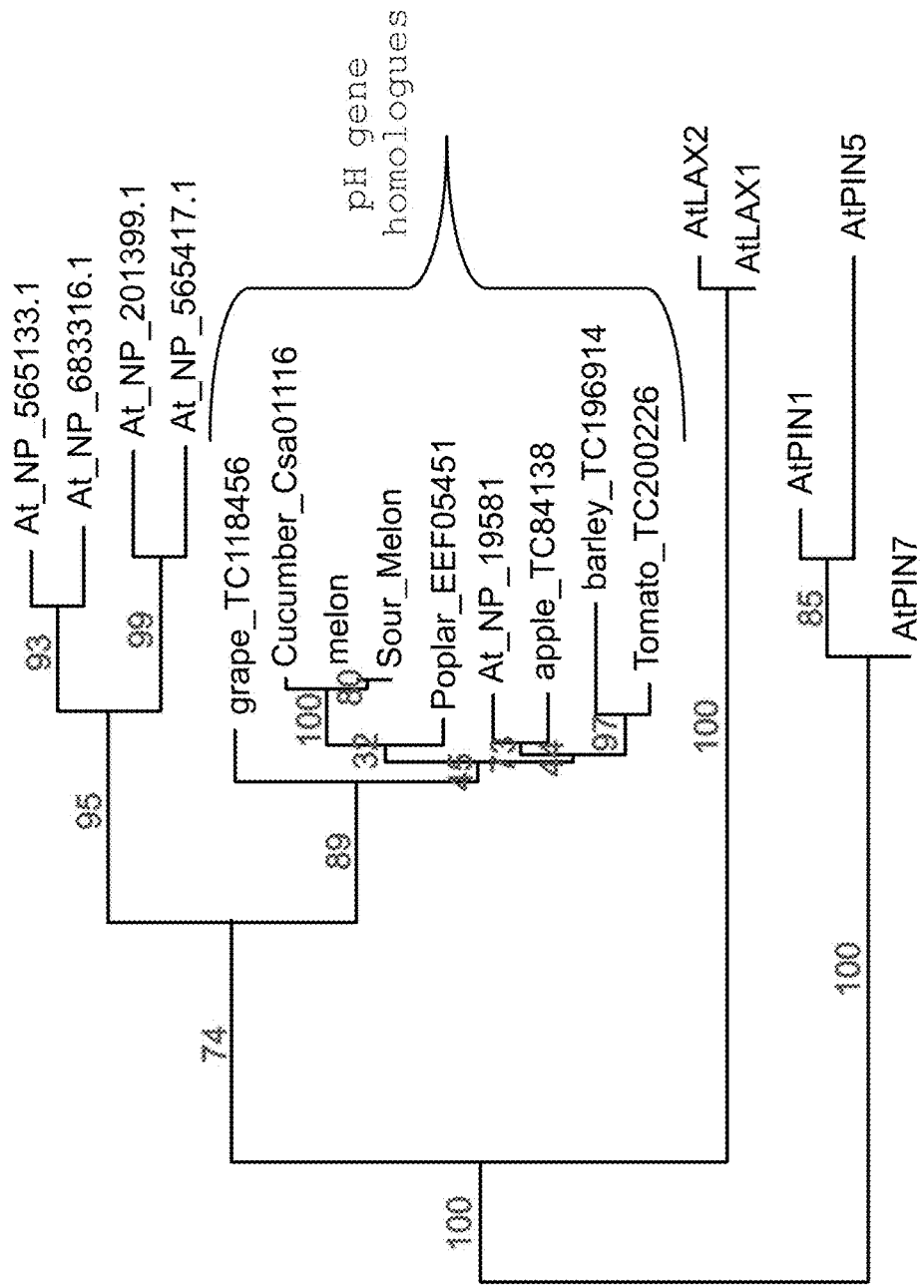

FIG. 6 depicts a phylogenetic tree [produced by World Wide Web (dot) phylogeny (dot) fr, Dereeper A., Audic S., Clayerie J. M., Blanc G. *BLAST-EXPLORER helps you building datasets for phylogenetic analysis*. BMC Evol Biol. 2010 Jan. 12; 10:8] indicating the clade of sequences associated with the melon and tomato sequences reported herein. The sequences referred to as PIN, LAX are known auxin/proton transporters. The five sequences from *Arabidopsis* presented in the uppermost clade are a closely related clade of sequences of unknown function, annotated as putative auxin efflux transporters. Numbers (shown in red) represent branch support, or bootstrap values in % as determined by the World Wide Web (dot) phylogeny (dot) fr program. The bootstrap value of 100 separating the clades of the LAX and PIN families from the family of the pH gene indicates that these clades are significantly distinct.

DESCRIPTION OF SPECIFIC EMBODIMENTS OF THE INVENTION

The present invention, in some embodiments thereof, relates to isolated polynucleotides and polypeptide encoded thereby, nucleic acid constructs, host cells and transgenic plants comprising same, and more particularly, but not exclusively, to methods of using same for modulating the acidity of a plant for controlling the acidity of a fruit, the nutrient uptake by the roots and the flower petal color.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have uncovered, following laborious experimentations the gene controlling acidity of a plant (termed hereinafter as the "pH gene").

Thus, as shown in the Examples section which follows, the gene was identified in melons by map-based cloning using recombinant inbred lines having defined pH values (Table 1, Example 1), and the mRNA and genomic sequences of the pH gene were identified [SEQ ID NOs:14 (genomic sequence), 1 (sour melon mRNA), and 2 (sour melon protein)]. Homologues in tomatoes and cucumber were also identified [SEQ ID NOs:31 and 5 (tomato mRNA and protein, respectively); and SEQ ID NOs: 30 and 6 (cucumber mRNA and protein, respectively)]. Sequence comparison between the gene isolated from sour and non-sour melons revealed the presence of a genetic mutation which is present in non-sour melons and is absent in sour melon. The mutation is a duplication of 12 nucleic acids at nucleotide positions 325-336 as set forth in SEQ ID NO:3 (325_336dupTTAATTGTTGCA) encoding a duplication mutation of the LIVA (SEQ ID NO:27) amino acid sequence at amino acid positions 107-110 as set forth in SEQ ID NO:4 (107_110dupLIVA) (FIGS. 1A-E, Example 2). Multiple sequence alignments showed that the novel pH gene is present in various unrelated plants (FIGS. 2A-F and 3, Example 3) with significant sequence similarity (Table 3, Example 3) and identity (Table 4, Example 3). Further protein modeling analysis revealed that the LIVA duplication mutation found in non-sour melon is expected to change the conformation of the pH protein (FIGS. 4A-D, Example 4). Moreover, thorough genotype and phenotype analyses demonstrated a direct correlation between presence of the LIVA duplication mutation and a decrease in fruit acidity (i.e., higher pH values) in melon varieties (FIG. 5, Tables 5 and 6, Example 5). A phylogenetic tree generated using the novel pH gene showed that a clade of highly similar sequences related to the melon pH gene is completely separated from a closely related clade of proteins of undetermined function (which are partially annotated as "auxin transporters" or as hypothetical or putative proteins) which are more distantly related to the characterized auxin transporter families of PIN and AUX (FIG. 6, Example 6). In addition, members of the closely related clade of the pH gene are expressed in plants, in both fruit tissue and non-fruit tissues such as leaves, flowers, roots and stems (Table 7, Example 6). The present inventors have further constructed transgenic plants transformed to express a silencing vector directed at down-regulating the pH genes in melon and tomato, which exhibit a decreased acidity (i.e., higher pH values) (Table 8, Example 7). On the other hand, transgenic tomato plants over-expressing the pH gene from either tomato or sour melon were found to exhibit a significant increase in plant's acidity as shown by the decrease in the measured pH values (Table 9, Example 8). These results demonstrate that the isolated pH gene identified herein can be used to regulate plant's acidity.

Thus, according to an aspect of some embodiments of the invention there is provided an isolated polynucleotide comprising a nucleic acid sequence encoding a polypeptide having at least 60% identity to a polypeptide selected from the group consisting of SEQ ID NO:2, 4, 5, 6, 8, 9 10, 28 and 29, wherein the polypeptide modulates acidity of a plant.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

The term "isolated" refers to at least partially separated from the natural environment e.g., from a plant cell.

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

According to some embodiments of the invention, the isolated polynucleotide comprising a nucleic acid sequence encoding a polypeptide having at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, e.g., 100% identity or homology to a polypeptide selected from the group consisting of SEQ ID NO:2, 4, 5, 6, 8, 9 10, 28 and 29, wherein the polypeptide modulates acidity of a plant.

Percentage of identity (e.g., global identity between amino acid sequences of two proteins), or homology (e.g., percent homology) can be determined using any homology comparison software, including for example, the BLAST® (Basic Local Alignment Search Tool, National Library of Medicine) or the TBLASTN® (Basic Local Alignment Search Tool, National Library of Medicine) software of the National Center of Biotechnology Information (NCBI) such as by using default parameters, when starting from a polypeptide sequence; the tBLASTX® (Basic Local Alignment Search Tool, National Library of Medicine) algorithm (available via the NCBI) such as by using default parameters, which compares the six-frame conceptual translation products of a nucleotide query sequence (both strands) against a protein sequence database; or the EMBOSS NEEDLE program of pairwise alignment available from Hypertext Transfer Protocol://World Wide Web (dot) ebi (dot) ac (dot) uk/Tools/psa/emboss_needle/nucleotide (dot) html, using default parameters (Matrix: BLOSUM62; GAP OPEN: 10; GAP extend: 0.5; Output format: pair; END GAP penalty: false; ENP GAP OPEN: 10; END GAP extend: 0.5).

Homologous sequences include both orthologous and paralogous sequences. The term "paralogous" relates to gene-duplications within the genome of a species leading to paralogous genes. The term "orthologous" relates to homologous genes in different organisms due to ancestral relationship.

One option to identify orthologues in monocot plant species is by performing a reciprocal BLAST® (Basic Local Alignment Search Tool, National Library of Medicine) search. This may be done by a first BLAST® (Basic Local Alignment Search Tool, National Library of Medicine) involving blasting the sequence-of-interest against any sequence database, such as the publicly available NCBI database which may be found at: Hypertext Transfer Protocol://World Wide Web (dot) ncbi (dot) nlm (dot) nih (dot) gov. If orthologues in rice were sought, the sequence-of-interest would be blasted against, for example, the 28,469 full-length cDNA clones from *Oryza sativa* Nipponbare available at NCBI. The BLAST® (Basic Local Alignment Search Tool, National Library of Medicine) results may be filtered. The full-length sequences of either the filtered results or the non-filtered results are then blasted back (second BLAST® (Basic Local Alignment Search Tool, National Library of Medicine)) against the sequences of the organism from which the sequence-of-interest is derived. The results of the first and second BLAST®s are then compared. An orthologue is identified when the sequence resulting in the highest score (best hit) in the first BLAST, (Basic Local Alignment Search Tool, National Library of Medicine) identifies in the second BLAST® (Basic Local Alignment Search Tool, National Library of Medicine) the query sequence (the original sequence-of-interest) as the best hit. Using the same rational a paralogue (homolog to a gene in the same organism) is found. In case of large sequence families, the ClustalW program may be used [Hypertext Transfer Protocol://World Wide Web (dot) ebi (dot) ac (dot) uk/Tools/clustalw2/index (dot) htmll, followed by a neighbor-joining tree (Hypertext Transfer Protocol://en (dot) wikipedia (dot) org/wiki/Neighbor-joining) which helps visualizing the clustering.

According to some embodiments of the invention, the homology is a global homology, i.e., an homology over the entire amino acid or nucleic acid sequences of the invention and not over portions thereof.

Identity (e.g., percent homology) can be determined using any homology comparison software, including for example, the BLASTN® (Basic Local Alignment Search Tool, National Library of Medicine) software of the National Center of Biotechnology Information (NCBI) such as by using default parameters.

According to some embodiments of the invention, the identity is a global identity, i.e., an identity over the entire amino acid or nucleic acid sequences of the invention and not over portions thereof.

According to some embodiments of the invention, the isolated polynucleotide encodes a polypeptide selected from the group consisting of SEQ ID NO:2, 4, 5, 6, 8, 9 10, 28 and 29.

Nucleic acid sequences encoding the polypeptides of the some embodiments of the invention may be optimized for expression. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N [(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A Table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization Tables such as those provided on-line at the Codon Usage Database through the NIAS (National Institute of Agrobiological Sciences) DNA bank in Japan (Hypertext Transfer Protocol://World Wide Web (dot) kazusa (dot) or (dot) jp/codon/). The Codon Usage Database contains codon usage tables for a number of different species, with each codon usage Table having been statistically determined based on the data present in Genbank.

By using the above Tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene.

According to some embodiments of the invention, the isolated polynucleotide comprising a nucleic acid sequence which is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, e.g., 100% identical to the polynucleotide selected from the group consisting of SEQ ID NOs: 1, 3, 30, 31, 32, 33, 34 and 35.

According to some embodiments of the invention the nucleic acid sequence modulates acidity of a plant.

According to an aspect of some embodiments of the invention, there is provided an isolated polynucleotide capable of down-regulating expression of the isolated polynucleotide of some embodiments of the invention a host cell.

According to some embodiments of the invention, the down-regulating polynucleotide prevents at least about 20%, e.g., at least about 30%, at least about 40%, at least about 50%, at least about 60%, at least about 70%, at least about 80%, at least about 85%, at least about 90%, at least about 95%, e.g., 100% of the expression level of the polynucleotide selected from the group consisting of SEQ ID NOs: 1, 3, 30, 31, 32, 33, 34 and 35.

Down-regulating polynucleotides can be used for example, in co-suppression, antisense suppression, RNA interference and ribozyme molecules as is further described hereinunder and in Examples 7 and 9 of the Examples section which follows. Methods and assays for qualifying the effect of the downregulating polynucleotide on the expression level of a polynucleotide-of-interest are known in the art and further described hereinunder.

Non-limiting examples of suitable down-regulating polynucleotides include those set forth by SEQ ID NOs: 15-16 (for downregulating the melon pH gene); SEQ ID NOs: 17-18 (for down-regulating of the tomato pH gene); and SEQ ID NOs: 40-41 (for downregulating the petunia pH gene.

According to an aspect of some embodiments of the invention, there is provided an isolated polynucleotide primer pair capable of specifically amplifying the isolated polynucleotide of some embodiments of the invention.

Non-limiting of primer pairs which can amplify the isolated polynucleotide of some embodiments of the invention include those depicted in SEQ ID NOs: 7 and 11; and 12 and 13.

Thus, the invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

The invention provides an isolated polypeptide comprising an amino acid sequence at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, e.g., 100% identical or homologous to a polypeptide selected from the group consisting of SEQ ID NOs:2, 4, 5, 6, 8, 9 10, 28 and 29, wherein the polypeptide modulates acidity of a plant.

According to some embodiments of the invention, the polypeptide comprising an amino acid sequence selected from the group consisting of SEQ ID NOs:2, 4, 5, 6, 8, 9 10, 28 and 29.

According to some embodiments of the invention, the polypeptide is set forth by SEQ ID NO:2, 4, 5, 6, 8, 9 10, 28 or 29.

The invention also encompasses fragments of the above described polypeptides and polypeptides having mutations, such as deletions, insertions or substitutions of one or more amino acids, either naturally occurring or man induced, either randomly or in a targeted fashion.

According to an aspect of some embodiments of the invention, there is provided a method of generating a transgenic plant, comprising expressing within the plant the isolated polynucleotide of some embodiments of the invention, or the nucleic acid construct of some embodiments of the invention, thereby generating the transgenic plant.

The phrase "expressing within the plant an exogenous polynucleotide" as used herein refers to upregulating the expression level of an exogenous polynucleotide within the plant by introducing the exogenous polynucleotide into a plant cell or plant and expressing by recombinant means, as further described herein below.

As used herein "expressing" refers to expression at the mRNA and optionally polypeptide level.

As used herein, the phrase "exogenous polynucleotide" refers to a heterologous nucleic acid sequence which may not be naturally expressed within the plant or which overexpression in the plant is desired. The exogenous polynucleotide may be introduced into the plant in a stable or transient manner, so as to produce a ribonucleic acid (RNA) molecule and/or a polypeptide molecule. It should be noted that the exogenous polynucleotide may comprise a nucleic acid sequence which is identical or partially homologous to an endogenous nucleic acid sequence of the plant.

The term "endogenous" as used herein refers to any polynucleotide or polypeptide which is present and/or naturally expressed within a plant or a cell thereof.

The term "plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising Acacia spp., Acer spp., Actinidia spp., Aesculus spp., Agathis australis, Albizia amara, Alsophila tricolor, Andropogon spp., Arachis spp, Areca catechu, Astelia fragrans, Astragalus cicer, Baikiaea plurijuga, Betula spp., Brassica spp., Bruguiera gymnorrhiza, Burkea africana, Butea frondosa, Cadaba farinosa, Calliandra spp, Camellia sinensis, Canna indica, Capsicum spp., Cassia spp., Centroema pubescens, Chacoomeles spp., Cinnamomum cassia, Coffea arabica, Colophospermum mopane, Coronillia varia, Cotoneaster serotina, Crataegus spp., Cucumis spp., Cupressus spp., Cyathea dealbata, Cydonia oblonga, Cryptomeria japonica, Cymbopogon spp., Cynthea dealbata, Cydonia oblonga, Dalbergia monetaria, Davallia divaricata, Desmodium spp., Dicksonia squarosa, Dibeteropogon amplectens, Dioclea spp, Dolichos spp., Dorycnium rectum, Echinochloa pyramidalis, Ehraffia spp., Eleusine coracana, Eragrestis spp., Erythrina spp., Eucalypfus spp., Euclea schimperi, Eulalia vi/losa, Pagopyrum spp., Feijoa sellowlana, Fragaria spp., Flemingia spp, Freycinetia banksli, Geranium thunbergii, GinAgo biloba, Glycine javanica, Gliricidia spp, Gossypium hirsutum, Grevillea spp., Guibourtia coleosperma, Hedysarum spp., Hemaffhia altissima, Heteropogon contoffus, Hordeum vulgare, Hyparrhenia rufa, Hypericum erectum, Hypeffhelia dissolute, Indigo incamata, Iris spp., Leptarrhena pyrolifolia, Lespediza spp., Lettuca spp., Leucaena leucocephala, Loudetia simplex, Lotonus bainesli, Lotus spp., Macrotyloma axillare, Malus spp., Manihot esculenta, Medicago saliva, Metasequoia glyptostroboides, Musa sapientum, Nicotianum spp., Onobrychis spp., Ornithopus spp., Oryza spp., Peltophorum africanum, Pennisetum spp., Persea gratissima, Petunia spp., Phaseolus spp., Phoenix canariensis, Phormium cookianum, Photinia spp., Picea glauca, Pinus spp., Pisum sativam, Podocarpus totara, Pogonarthria fleckii, Pogonaffhria squarrosa, Populus spp., Prosopis cineraria, Pseudotsuga menziesii, Pterolobium stellatum, Pyrus communis, Quercus spp., Rhaphiolepsis umbellata, Rhopalostylis sapida, Rhus natalensis, Ribes grossularia, Ribes spp., Robinia pseudoacacia, Rosa spp., Rubus spp., Salix spp., Schyzachyrium sanguineum, Sciadopitys vefficillata, Sequoia sempervirens, Sequoiadendron giganteum, Sorghum bicolor, Spinacia spp., Sporobolus fimbriatus, Stiburus alopecuroides, Stylosanthos humilis, Tadehagi spp, Taxodium distichum, Themeda triandra, Trifolium spp., Triticum spp., Tsuga heterophylla, Vaccinium spp., Vicia spp., Vitis vinifera, Watsonia pyramidata, Zantedeschia aethiopica, Zea mays, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, eucalyptus, a tree, an ornamental plant, a perennial grass and a forage crop. Alternatively algae and other non-Viridiplantae can be used for the methods of the present invention.

According to some embodiments of the invention, the plant has a gene, which is an orthologue of the identified melon pH gene (e.g., SEQ ID NOs: 1-4), and which is normally expressed in developing fruit, thereby likely functioning in acid accumulation.

According to some embodiments of the invention, the plant used according to some embodiments of the invention is of a plant family selected from the group consisting of: Solanaceae, Cucurbitaceae, Rutaceae, Rosaceae, and Vitaceae.

According to some embodiments of the invention, the plant used according to some embodiments of the invention is selected from the group consisting of melon, tomato, apple, grape, strawberry, orange, peach, and petunia.

According to some embodiments of the invention, expressing the exogenous polynucleotide of the invention within the plant is effected by transforming one or more cells of the plant with the exogenous polynucleotide, followed by generating a mature plant from the transformed cells and cultivating the mature plant under conditions suitable for expressing the exogenous polynucleotide within the mature plant.

According to some embodiments of the invention, the transformation is effected by introducing to the plant cell a nucleic acid construct which includes the exogenous polynucleotide of some embodiments of the invention and at least one cis-acting regulatory element (e.g., promoter) for directing transcription of the exogenous polynucleotide in a host cell (a plant cell). Further details of suitable transformation approaches are provided hereinbelow.

According to some embodiments of the invention, there is provided a nucleic acid construct comprising the isolated polynucleotide of the invention, and a cis-acting regulatory element (e.g., a promoter sequence) for directing transcription of the nucleic acid sequence of the isolated polynucleotide in a host cell.

According to some embodiments of the invention, there is provided a plant cell exogenously expressing the polynucleotide of some embodiments of the invention, the nucleic acid construct of some embodiments of the invention and/or the polypeptide of some embodiments of the invention.

According to some embodiments of the invention, the isolated polynucleotide is operably linked to the promoter sequence.

A coding nucleic acid sequence is "operably linked" to a regulatory sequence (e.g., promoter) if the regulatory sequence is capable of exerting a regulatory effect on the coding sequence linked thereto.

As used herein, the term "promoter" refers to a region of DNA which lies upstream of the transcriptional initiation site of a gene to which RNA polymerase binds to initiate transcription of RNA. The promoter controls where (e.g., which portion of a plant) and/or when (e.g., at which stage or condition in the lifetime of an organism) the gene is expressed.

Any suitable promoter sequence can be used by the nucleic acid construct of the present invention. According to some embodiments of the invention, the promoter is a constitutive promoter, a tissue-specific, an inducible promoter (e.g., abiotic stress-inducible), or a developmental specific promoter.

Non-limiting examples of suitable promoters are described in Jones H D, Sparks C A. Promoter sequences for defining transgene expression. Methods Mol. Biol. 2009; 478:171-84, which is fully incorporated herein by reference.

Suitable constitutive promoters include, for example, CaMV 35S promoter (Odell et al., Nature 313:810-812, 1985); maize Ubi 1 (Christensen et al., Plant Sol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al, Plant J November; 2(6):837-44, 1992); ubiquitin (Christensen et al, Plant Mol. Biol. 18: 675-689, 1992); Rice cyclophilin (Bucholz et al, Plant Mol. Biol. 25(5):837-43, 1994); Maize H3 histone (Lepetit et al, Mol. Gen. Genet. 231: 276-285, 1992); Actin 2 (An et al, Plant J. 10(1); 107-121, 1996) and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597: 5,466,785; 5,399,680; 5,268,463; and 5,608,142.

Suitable tissue-specific promoters include, but not limited to, leaf-specific promoters [such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993], seed-preferred promoters [e.g., Napin (originated from *Brassica napus* which is characterized by a seed specific promoter activity; Stuitje A. R. et. al. Plant Biotechnology Journal 1 (4): 301-309), from seed specific genes (Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson' et al., Plant Mol. Biol. 18: 235-245, 1992), legumin (Ellis, et al. Plant Mol. Biol. 10: 203-214, 1988), Glutelin (rice) (Takaiwa, et al., Mol. Gen. Genet. 208: 15-22, 1986; Takaiwa, et al., FEBS Letts. 221: 43-47, 1987), Zein (Matzke et al Plant Mol Biol, 143). 323-32 1990), napA (Stalberg, et al, Planta 199: 515-519, 1996), Wheat SPA (Albanietal, Plant Cell, 9: 171-184, 1997), sunflower oleosin (Cummins, et al., Plant Mol. Biol. 19: 873-876, 1992)], endosperm specific promoters [e.g., wheat LMW and HMW, glutenin-1 (Mol Gen Genet. 216:81-90, 1989; NAR 17:461-2), wheat a, b and g gliadins (EMBO 3:1409-15, 1984), Barley ltrl promoter, barley B1, C, D hordein (Theor Appl Gen 98:1253-62, 1999; Plant J 4:343-55, 1993; Mol Gen Genet. 250:750-60, 1996), Barley DOF (Mena et al, The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al, Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorghum gamma-kafirin (PMB 32:1029-35, 1996)], embryo specific promoters [e.g., rice OSH1 (Sato et al, Proc. Natl. Acad. Sci. USA, 93: 8117-8122), KNOX (Postma-Haarsma et al., Plant Mol. Biol. 39:257-71, 1999), rice oleosin (Wu et at, J. Biochem., 123:386, 1998)], and flower-specific promoters [e.g., AtPRP4, chalene synthase (chsA) (Van der Meer, et al., Plant Mol. Biol. 15, 95-109, 1990), LAT52 (Twell et al Mol. Gen. Genet. 217:240-245; 1989), apetala-3], and root promoters such as the ROOTP promoter.

The nucleic acid construct of some embodiments of the invention can further include an appropriate selectable marker and/or an origin of replication. According to some embodiments of the invention, the nucleic acid construct utilized is a shuttle vector, which can propagate both in *E. coli* (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

According to an aspect of some embodiments of the invention, there is provided a plant comprising the nucleic acid construct of some embodiments of the invention or the plant cell of some embodiments of the invention.

According to some embodiments of the invention, the plant is transformed with the nucleic acid construct or transfected with the nucleic acid construct of some embodiments of the invention.

According to some embodiments of the invention, the plant exogenously expressing the isolated polynucleotide, the isolated polypeptide or the nucleic acid construct of some embodiments of the invention.

The nucleic acid construct of some embodiments of the invention can be utilized to stably or transiently transform plant cells. In stable transformation, the exogenous polynucleotide is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338:274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S, and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

According to some embodiments of the invention, the transgenic plants are generated by transient transformation of leaf cells, meristematic cells or the whole plant.

Transient transformation can be effected by any of the direct DNA transfer methods described above or by viral infection using modified plant viruses.

Viruses that have been shown to be useful for the transformation of plant hosts include CaMV, Tobacco mosaic virus (TMV), brome mosaic virus (BMV) and Bean Common Mosaic Virus (BV or BCMV). Transformation of plants using plant viruses is described in U.S. Pat. No. 4,855,237 (bean golden mosaic virus; BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261.

According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; Takamatsu et al. FEBS Letters (1990) 269:73-76; and U.S. Pat. No. 5,316,931.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression. A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the exogenous polynucleotide includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

The isolated polynucleotide of some embodiments of the invention can be expressed along with an additional gene-of-interest. Expressing a plurality of exogenous polynucleotides in a single host plant can be effected by co-introducing multiple nucleic acid constructs, each including a different exogenous polynucleotide, into a single plant cell. The transformed cell can then be regenerated into a mature plant using the methods described hereinabove.

Alternatively, expressing a plurality of exogenous polynucleotides in a single host plant can be effected by co-introducing into a single plant-cell a single nucleic-acid construct including a plurality of different exogenous polynucleotides. Such a construct can be designed with a single promoter sequence which can transcribe a polycistronic messenger RNA including all the different exogenous polynucleotide sequences. To enable co-translation of the different polypeptides encoded by the polycistronic messenger RNA, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the different polypeptides described above will be translated from both the capped 5' end and the two internal IRES sequences of the polycistronic RNA molecule to thereby produce in the cell all different polypeptides. Alternatively, the construct can include several promoter sequences each linked to a different exogenous polynucleotide sequence.

The plant cell transformed with the construct including a plurality of different exogenous polynucleotides, can be regenerated into a mature plant, using the methods described hereinabove.

Alternatively, expressing a plurality of exogenous polynucleotides in a single host plant can be effected by introducing different nucleic acid constructs, including different exogenous polynucleotides, into a plurality of plants. The regenerated transformed plants can then be cross-bred and resultant progeny selected for superior abiotic stress tolerance, water use efficiency, fertilizer use efficiency, growth, biomass, yield and/or vigor traits, using conventional plant breeding techniques.

According to some embodiments of the invention, the plant cell forms a part of a plant.

Thus, the invention encompasses plants exogenously expressing the polynucleotide(s), the nucleic acid constructs and/or polypeptide(s) of the invention. Once expressed within the plant cell or the entire plant, the level of the polypeptide encoded by the exogenous polynucleotide can be determined by methods well known in the art such as, activity assays, Western blots using antibodies capable of specifically binding the polypeptide, Enzyme-Linked Immuno Sorbent Assay (ELISA), radio-immuno-assays (RIA), immunohistochemistry, immunocytochemistry, immunofluorescence and the like.

Methods of determining the level in the plant of the RNA transcribed from the exogenous polynucleotide are well known in the art and include, for example, Northern blot analysis, reverse transcription polymerase chain reaction (RT-PCR) analysis (including quantitative, semi-quantitative or real-time RT-PCR) and RNA-in situ hybridization.

The identification of the pH gene and protein disclosed herein, together with the polymorphism responsible for its lack of function and subsequent lack of acid accumulation, can be used for the transgenic production of melons or other fruit types with altered fruit acidity, either by overexpressing or reducing expression by the known technologies of molecular biology.

For example, as shown in Table 8 (Example 7 of the Examples section which follows) and Table 9 (Example 8 of the Examples section which follows) by down-regulating or up-regulating the expression level of the pH gene in the plant the acidity of the plant tissue (e.g., fruit) can be decreased (i.e., higher pH values) or increased (i.e., lower pH values), respectively, as compared to native plants of the same species which are grown under the same growth conditions and which are not modified with the biomolecules (polynucleotide or polypeptides) of some embodiments of the invention.

According to an aspect of some embodiments of the invention, there is provided a method of regulating acidity of a plant. The method is effected by modulating an expression level of a polypeptide having at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, e.g., 100% identity or homology to a polypeptide selected from the group consisting of SEQ ID NO:2, 4, 5, 6, 8, 9 10, 28 and 29, thereby modulating the acidity of the plant.

As used herein the phrase "acidity of a plant" refers to the acidity (pH value, proton concentration) of at least a portion of a plant.

According to some embodiments of the invention, the portion of the plant is a hydratic portion.

According to some embodiments of the invention, the portion of the plant can be, but is not limited to, fruit, root, leaf, stem, flower and petal.

The acidity of a plant can be determined in pH values as detected by a pH meter. The overall scale of pH values ranges between 0-14, wherein a lower pH value indicates a higher acidity; and wherein a higher pH value indicates a lower acidity [e.g., more neutral (around pH 7) or basic].

As used herein the term "regulating" refers to either "increasing" or "decreasing" the acidity of the plant by at least about 0.1 pH value, e.g., by at least about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2, about 2.5, about 3, about 3.5, about 4, about 4.5, about 5, about 5.5, about 6, about 6.5, or about 7 or more pH values as compared to a native plant [i.e., a plant not modified with the biomolecules (polynucleotide or polypeptides) of some embodiments of the invention, e.g., a non-transformed plant of the same species which is grown under the same growth conditions].

According to some embodiments of the invention, regulating comprises increasing acidity of the plant, and modulating comprises up-regulating the expression level of the polypeptide.

According to some embodiments of the invention, up-regulating the expression level of the polypeptide is performed by expressing within the plant an exogenous polynucleotide encoding the polypeptide of some embodiments of the invention as described hereinabove.

According to some embodiments of the invention, regulating comprises decreasing acidity of the plant, and modulating comprises down-regulating the expression level of the polypeptide is performed by transforming a plant cell of the plant with a polynucleotide capable of downregulating expression level of the polypeptide.

Downregulation (gene silencing) of the transcription or translation product of an endogenous gene (e.g., the pH gene) can be achieved by co-suppression, antisense suppression, RNA interference and ribozyme molecules.

Co-Suppression (Sense Suppression)—Inhibition of the endogenous gene can be achieved by co-suppression, using an RNA molecule (or an expression vector encoding same) which is in the sense orientation with respect to the transcription direction of the endogenous gene. The polynucleotide used for co-suppression may correspond to all or part of the sequence encoding the endogenous polypeptide and/or to all or part of the 5' and/or 3' untranslated region of the endogenous transcript; it may also be an unpolyadenylated RNA; an RNA which lacks a 5' cap structure; or an RNA which contains an unsplicable intron. In some embodiments, the polynucleotide used for co-suppression is designed to eliminate the start codon of the endogenous polynucleotide so that no protein product will be translated. Methods of co-suppression using a full-length cDNA sequence as well as a partial cDNA sequence are known in the art (see, for example, U.S. Pat. No. 5,231,020).

According to some embodiments of the invention, down-regulation of the endogenous gene is performed using an amplicon expression vector which comprises a plant virus-derived sequence that contains all or part of the target gene but generally not all of the genes of the native virus. The viral sequences present in the transcription product of the expression vector allow the transcription product to direct its own replication. The transcripts produced by the amplicon may be either sense or antisense relative to the target sequence [see for example, Angell and Baulcombe, (1997) EMBO J. 16:3675-3684; Angell and Baulcombe, (1999) Plant J. 20:357-362, and U.S. Pat. No. 6,646,805, each of which is herein incorporated by reference].

Antisense Suppression—Antisense suppression can be performed using an antisense polynucleotide or an expression vector which is designed to express an RNA molecule complementary to all or part of the messenger RNA (mRNA) encoding the endogenous polypeptide and/or to all or part of the 5' and/or 3' untranslated region of the endogenous gene. Over expression of the antisense RNA molecule can result in reduced expression of the native (endogenous) gene. The antisense polynucleotide may be fully complementary to the target sequence (i.e., 100% identical to the complement of the target sequence) or partially complementary to the target sequence (i.e., less than 100% identical, e.g., less than 90%, less than 80% identical to the comple-ment of the target sequence). Antisense suppression may be used to inhibit the expression of multiple proteins in the same plant (see e.g., U.S. Pat. No. 5,942,657). In addition, portions of the antisense nucleotides may be used to disrupt the expression of the target gene. Generally, sequences of at least about 50 nucleotides, at least about 100 nucleotides, at least about 200 nucleotides, at least about 300, at least about 400, at least about 450, at least about 500, at least about 550, or greater may be used. Methods of using antisense suppression to inhibit the expression of endogenous genes in plants are described, for example, in Liu, et al., (2002) Plant Physiol. 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal [See, U.S. Patent Publication No. 20020048814, herein incorporated by reference].

RNA intereference—RNA interference can be achieved using a polynucleotide, which can anneal to itself and form a double stranded RNA having a stem-loop structure (also called hairpin structure), or using two polynucleotides, which form a double stranded RNA.

For hairpin RNA (hpRNA) interference, the expression vector is designed to express an RNA molecule that hybridizes to itself to form a hairpin structure that comprises a single-stranded loop region and a base-paired stem.

In some embodiments of the invention, the base-paired stem region of the hpRNA molecule determines the specificity of the RNA interference. In this configuration, the sense sequence of the base-paired stem region may correspond to all or part of the endogenous mRNA to be downregulated, or to a portion of a promoter sequence controlling expression of the endogenous gene to be inhibited; and the antisense sequence of the base-paired stem region is fully or partially complementary to the sense sequence. Such hpRNA molecules are highly efficient at inhibiting the expression of endogenous genes, in a manner which is inherited by subsequent generations of plants [See, e.g., Chuang and Meyerowitz, (2000) Proc. Natl. Acad. Sci. USA 97:4985-4990; Stoutjesdijk, et al., (2002) Plant Physiol. 129:1723-1731; and Waterhouse and Helliwell, (2003) Nat. Rev. Genet. 4:29-38; Chuang and Meyerowitz, (2000) Proc. Natl. Acad. Sci. USA 97:4985-4990; Pandolfini et al., BMC Biotechnology 3:7; Panstruga, et al., (2003) Mol. Biol. Rep. 30:135-140; and U.S. Patent Publication No. 2003/0175965; each of which is incorporated by reference].

According to some embodiments of the invention, the sense sequence of the base-paired stem is from about 10 nucleotides to about 2,500 nucleotides in length, e.g., from about 10 nucleotides to about 500 nucleotides, e.g., from about 15 nucleotides to about 300 nucleotides, e.g., from about 20 nucleotides to about 100 nucleotides, e.g., or from about 25 nucleotides to about 100 nucleotides.

According to some embodiments of the invention, the antisense sequence of the base-paired stem may have a length that is shorter, the same as, or longer than the length of the corresponding sense sequence.

According to some embodiments of the invention, the loop portion of the hpRNA can be from about 10 nucleotides to about 500 nucleotides in length, for example from about 15 nucleotides to about 100 nucleotides, from about 20 nucleotides to about 300 nucleotides or from about 25 nucleotides to about 400 nucleotides in length.

According to some embodiments of the invention, the loop portion of the hpRNA can include an intron (ihpRNA), which is capable of being spliced in the host cell. The use of an intron minimizes the size of the loop in the hairpin RNA molecule following splicing and thus increases efficiency of the interference [See, for example, Smith, et al., (2000) Nature 407:319-320; Wesley, et al., (2001) Plant J. 27:581-590; Wang and Waterhouse, (2001) Curr. Opin. Plant Biol. 5:146-150; Helliwell and Waterhouse, (2003) Methods 30:289-295; Brummell, et al. (2003) Plant J. 33:793-800; and U.S. Patent Publication No. 2003/0180945; WO 98/53083; WO 99/32619; WO 98/36083; WO 99/53050; US 20040214330; US 20030180945; U.S. Pat. Nos. 5,034,323; 6,452,067; 6,777,588; 6,573,099 and 6,326,527; each of which is herein incorporated by reference].

In some embodiments of the invention, the loop region of the hairpin RNA determines the specificity of the RNA interference to its target endogenous RNA. In this configuration, the loop sequence corresponds to all or part of the endogenous messenger RNA of the target gene. See, for example, WO 02/00904; Mette, et al., (2000) EMBO J. 19:5194-5201; Matzke, et al., (2001) Curr. Opin. Genet. Devel. 11:221-227; Scheid, et al., (2002) Proc. Natl. Acad. Sci., USA 99:13659-13662; Aufsaftz, et al., (2002) Proc. Nat'l. Acad. Sci. 99(4):16499-16506; Sijen, et al., Curr. Biol. (2001) 11:436-440), each of which is incorporated herein by reference.

For double-stranded RNA (dsRNA) interference, the sense and antisense RNA molecules can be expressed in the same cell from a single expression vector (which comprises sequences of both strands) or from two expression vectors (each comprising the sequence of one of the strands). Methods for using dsRNA interference to inhibit the expression of endogenous plant genes are described in Waterhouse, et al., (1998) Proc. Natl. Acad. Sci. USA 95:13959-13964; and WO 99/49029, WO 99/53050, WO 99/61631, and WO 00/49035; each of which is herein incorporated by reference.

According to some embodiments of the invention, RNA interference is effected using an expression vector designed to express an RNA molecule that is modeled on an endogenous micro RNAs (miRNA) gene. Micro RNAs (miRNAs) are regulatory agents consisting of about 22 ribonucleotides and highly efficient at inhibiting the expression of endogenous genes [Javier, et al., (2003) Nature 425:257-263]. The miRNA gene encodes an RNA that forms a hairpin structure containing a 22-nucleotide sequence that is complementary to the endogenous target gene.

Ribozyme—Catalytic RNA molecules, ribozymes, are designed to cleave particular mRNA transcripts, thus preventing expression of their encoded polypeptides. Ribozymes cleave mRNA at site-specific recognition sequences. For example, "hammerhead ribozymes" (see, for example, U.S. Pat. No. 5,254,678) cleave mRNAs at locations dictated by flanking regions that form complementary base pairs with the target mRNA. The sole requirement is that the target RNA contains a 5'-UG-3' nucleotide sequence. Hammerhead ribozyme sequences can be embedded in a stable RNA such as a transfer RNA (tRNA) to increase cleavage efficiency in vivo [Perriman et al. (1995) Proc. Natl. Acad. Sci. USA, 92(13):6175-6179; de Feyter and Gaudron Methods in Molecular Biology, Vol. 74, Chapter 43, "Expressing Ribozymes in Plants", Edited by Turner, P. C, Humana Press Inc., Totowa, N.J.; U.S. Pat. No. 6,423,885]. RNA endoribonucleases such as that found in Tetrahymena thermophila are also useful ribozymes (U.S. Pat. No. 4,987,071).

Plant lines transformed with any of the downregulating molecules described hereinabove are screened to identify those that show the greatest inhibition of the endogenous polypeptide-of-interest, and thereby the increase of the desired plant trait (e.g., change in plant acidity).

According to some embodiments of the invention, the plant comprises a fruit.

According to some embodiments of the invention, the fruit is a ripe fruit.

According to some embodiments of the invention, regulating the expression level of the polynucleotide or the polypeptide encoded thereby is effected using a fruit specific promoter.

According to some embodiments of the invention, regulating is effected using a developmental-specific promoter for modulating expression of the polypeptide before ripening of the fruit.

For example, modifying the acidity of a cucumber fruit can be performed before fruit ripening.

As described in the Background section, the pH of fruit affects the post harvest quality of the fruit. Thus, reduction of pH (increased acidity) is likely to exert a positive effect on fruit storage and on inhibition of pathogenic attacks.

According to an aspect of some embodiments of the invention, there is provided a method of affecting post harvest fruit storage. The method is effected by regulating acidity of the fruit according to the method of some embodiments of the invention, wherein when the regulating comprises increasing acidity of the fruit then the post harvest fruit storage is increased, and wherein when the regulating comprises decreasing acidity of the fruit then the post harvest fruit storage is decreased.

According to some embodiments of the invention, the plant comprises a non-fruit portion.

According to some embodiments of the invention, the non-fruit portion comprises roots.

It should be noted that the plant's roots pH affects the pH of the rhizosphere, and thereby can increase or decrease uptake of nutrients. Thus, increased acidity of the plant's roots can increase nutrient uptake through the roots since the acidity increases the solubility of nutrients such as iron (Fe), manganese (Mn), and copper (Cu), toxic metals such as aluminum, or heavy metals such Cadmium (Cd), Lead (Pb) and zinc (Zn) within the soil. Thus, reducing root's acidity can relieve aluminum or heavy metal toxicity.

According to an aspect of some embodiments of the invention, there is provided a method of affecting nutrient, toxic chemicals or heavy metals uptake of a plant, comprising regulating acidity of the roots according to the method of some embodiments of the invention, wherein when the regulating comprises increasing acidity of the roots then the nutrient, toxic chemicals or heavy metals uptake is increased, and wherein when the regulating comprises decreasing acidity of the roots then the nutrient, toxic chemicals or heavy metals uptake is decreased or unchanged.

It should be noted that increasing the acidity of plant's roots is desirable when there is a need to increase uptake of nutrients such as iron, magnesium and copper. In addition, the increased uptake of nutrients may also increase fertilizer (e.g., nitrogen, micronutrients) use efficiency of a plant, especially when grown under limiting fertilizer (e.g., nitrogen) concentrations. Alternatively, in heavy metal soils increasing root pH (i.e., decreasing acidity of the roots) can reduce uptake of heavy metals, which are toxic to the plant.

According to some embodiments of the invention, the plant with increased root(s)' acidity is not a pine tree.

The effect of the transgene (the exogenous polynucleotide encoding the polypeptide) on fertilizer use efficiency (e.g., nitrogen use efficiency) can be determined using known methods such as detailed below and in the Examples section which follows.

Fertilizer Use Efficiency—To analyze whether the transgenic plants are more responsive to fertilizers, plants are grown in agar plates or pots with a limited amount of fertilizer, as described, for example, in Yanagisawa et al (Proc Natl Acad Sci USA. 2004; 101:7833-8). The plants are analyzed for their overall size, time to flowering, yield, protein content of shoot and/or grain. The parameters checked are the overall size of the mature plant, its wet and dry weight, the weight of the seeds yielded, the average seed size and the number of seeds produced per plant. Other parameters that may be tested are: the chlorophyll content of leaves (as nitrogen plant status and the degree of leaf verdure is highly correlated), amino acid and the total protein content of the seeds or other plant parts such as leaves or shoots, oil content, etc. Similarly, instead of providing nitrogen at limiting amounts, phosphate or potassium can be added at increasing concentrations. Again, the same parameters measured are the same as listed above. In this way, nitrogen use efficiency (NUE), phosphate use efficiency (PUE) and potassium use efficiency (KUE) are assessed, checking the ability of the transgenic plants to thrive under nutrient restraining conditions.

Nitrogen Use Efficiency—To analyze whether the transgenic plants (e.g., *Arabidopsis* plants) are more responsive to nitrogen, plant are grown in 0.75-3 millimolar (mM, nitrogen deficient conditions) or 6-10 mM (optimal nitrogen concentration). Plants are allowed to grow for additional 25 days or until seed production. The plants are then analyzed for their overall size, time to flowering, yield, protein content of shoot and/or grain/seed production. The parameters checked can be the overall size of the plant, wet and dry weight, the weight of the seeds yielded, the average seed size and the number of seeds produced per plant. Other parameters that may be tested are: the chlorophyll content of leaves (as nitrogen plant status and the degree of leaf greenness is highly correlated), amino acid and the total protein content of the seeds or other plant parts such as leaves or shoots and oil content. Transformed plants not exhibiting substantial physiological and/or morphological effects, or exhibiting higher measured parameters levels than wild-type plants, are identified as nitrogen use efficient plants.

Nitrogen Use Efficiency Assay Using Plantlets—The assay is done according to Yanagisawa-S. et al. with minor modifications ("Metabolic engineering with Dof1 transcription factor in plants: Improved nitrogen assimilation and growth under low-nitrogen conditions" *Proc. Natl. Acad. Sci. USA* 101, 7833-7838). Briefly, transgenic plants which are grown for 7-10 days in 0.5×MS [Murashige-Skoog] supplemented with a selection agent are transferred to two nitrogen-limiting conditions: MS media in which the combined nitrogen concentration ($NH_4NO_3$ and $KNO_3$) was 0.75 mM (nitrogen deficient conditions) or 6-15 mM (optimal nitrogen concentration). Plants are allowed to grow for additional 30-40 days and then photographed, individually removed from the Agar (the shoot without the roots) and immediately weighed (fresh weight) for later statistical analysis. Constructs for which only T1 seeds are available are sown on selective media and at least 20 seedlings (each one representing an independent transformation event) are carefully transferred to the nitrogen-limiting media. For constructs for which T2 seeds are available, different transformation events are analyzed. Usually, 20 randomly selected plants from each event are transferred to the nitrogen-limiting media allowed to grow for 3-4 additional weeks and individually weighed at the end of that period. Transgenic plants are compared to control plants grown in parallel under the same conditions. Mock-transgenic plants expressing the uidA reporter gene (GUS) under the same promoter or transgenic plants carrying the same promoter but lacking a reporter gene are used as control.

Nitrogen Determination—The procedure for N (nitrogen) concentration determination in the structural parts of the plants involves the potassium persulfate digestion method to convert organic N to $NO_3^-$ (Purcell and King 1996 Argon. J. 88:111-113, the modified $Cd^-$ mediated reduction of $NO_3^-$ to $NO_2^-$ (Vodovotz 1996 Biotechniques 20:390-394) and the measurement of nitrite by the Griess assay (Vodovotz 1996, supra). The absorbance values are measured at 550 nm against a standard curve of $NaNO_2$. The procedure is described in details in Samonte et al. 2006 Agron. J. 98:168-176.

According to some embodiments of the invention, the non-fruit portion comprises flower petal.

As described in Example 9 of the Examples section which follows, the flower petal color of petunia with a silenced expression of the endogenous pH gene (i.e. downregulation of the pH gene) is expected to result in a bluer hue as compared to the control non-infected plants.

According to an aspect of some embodiments of the present invention there is provided a method of affecting flower petal color, comprising regulating acidity of the flower petal according to the method of some embodiments of the invention, to thereby change the flower petal color.

According to some embodiments of the invention, wherein when the regulating comprises increasing acidity of the flower petal then the flower petal color is more red than in a non-transgenic or in a non-transformed plant of the same species under identical growth conditions, and wherein when the regulating comprises decreasing acidity of the flower petal then the flower petal color is more blue than in a non-transgenic or in a non-transformed plant of the same species under identical growth conditions.

As is further shown in FIGS. 1E and 4A-D and Tables 5-6 and described in Examples 2 and 4 of the Examples section which follows, the presence or absence of the LIVA duplication mutation in a melon variety genome indicates whether the melon variety exhibits less or more fruit acidity, respectively. These results suggest the use of the LIVA duplication mutation for selecting a melon variety for breeding.

The identification of the pH gene and protein disclosed herein, together with the polymorphism responsible for its lack of function and subsequent lack of acid accumulation, can be used in breeding for melon fruit with either low or high acid content. Since the polymorphism is within the gene itself, the marker based on the polymorphism is more reliable than previously used linked markers, which suffer from the probability of crossovers and incorrect genotyping.

According to an aspect of some embodiments of the invention, there is provided a method of selecting a melon plant for breeding, comprising determining in a tissue of the plant a presence or an absence of a LIVA (SEQ ID NO:27) duplication at amino acids 107-110 of SEQ ID NO:4, wherein the presence of the LIVA duplication indicates that a fruit of the melon plant is expected to be non-sour, and wherein the absence of the LIVA duplication indicates that a fruit of the melon plant is expected to be sour, thereby selecting the melon plant for breeding.

The sequence information and annotations uncovered by the present teachings can be harnessed in favor of classical breeding. Thus, sub-sequence data of those polynucleotides described above, can be used as markers for marker assisted selection (MAS), in which a marker is used for indirect selection of a genetic determinant or determinants of a trait of interest [e.g., increased or decreased acidity of the plant; change (increased or decreased) nutrient uptake; or change in petal color]. Nucleic acid data of the present teachings (DNA or RNA sequence) may contain or be linked to polymorphic sites or genetic markers on the genome such as restriction fragment length polymorphism (RFLP), microsatellites and single nucleotide polymorphism (SNP), DNA fingerprinting (DFP), amplified fragment length polymorphism (AFLP), expression level polymorphism, polymorphism of the encoded polypeptide and any other polymorphism at the DNA or RNA sequence.

It should be noted that once the gene controlling the acidity in melon (the pH gene) has been identified, and the loss-of-function mutation responsible for changing a sour melon (SEQ ID NO:2) to a non-sour melon (SEQ ID NO:4) has been characterized, such sequence information can be used to select for nucleic acid variations in homologous genes from other plants and to identify loss-of-function mutations which control the acidity in additional plants.

According to an aspect of some embodiments of the invention, there is provided a method of identifying a nucleic acid variation associated with decreased acidity of a plant, comprising identifying in at least one plant of a plurality of plants a loss-of-function mutation in a polypeptide having at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, e.g., 100% identity or homology to a polypeptide selected from the group consisting of SEQ ID NO:2, 4, 5, 6, 8, 9 10, 28 and 29, wherein the polypeptide modulates acidity of a plant, thereby identifying the nucleic acid variation associated with decreased acidity of the plant.

According to some embodiments of the invention, the method further comprising subjecting a plurality of plants to mutagenesis prior to identifying the loss-of-function mutation in the polypeptide, to thereby induce a nucleic acid variation which results in a loss-of-function mutation in the polypeptide having at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, e.g., 100% identity or homology to a polypeptide selected from the group consisting of SEQ ID NO:2, 4, 5, 6, 8, 9 10, 28 and 29.

As used herein, the phrase "nucleic acid variation" refers to any mutation in the DNA sequence of a plant (e.g., of a plant cell) which can result in downregulation of the expression level and/or activity of isolated polypeptide of some embodiments of the invention (e.g., the polypeptide encoded by the isolated polynucleotide of the invention). Non-limiting examples of such nucleic acid variations include a missense mutation, i.e., a mutation which changes an amino acid residue in the protein with another amino acid residue and thereby abolishes the enzymatic activity of the protein; a nonsense mutation, i.e., a mutation which introduces a stop codon in a protein, e.g., an early stop codon which results in a shorter protein devoid of the enzymatic activity; a frameshift mutation, i.e., a mutation, usually, deletion or insertion of nucleic acid(s) which changes the reading frame of the protein, and may result in an early termination by introducing a stop codon into a reading frame (e.g., a truncated protein, devoid of the enzymatic activity), or in a longer amino acid sequence (e.g., a readthrough protein) which affects the secondary or tertiary structure of the protein and results in a non-functional protein, devoid of the enzymatic activity of the "wild-type" or non-mutated polypeptide; a readthrough mutation due to a frameshift mutation or a modified stop codon mutation (i.e., when the stop codon is mutated into an amino acid codon), with an abolished enzymatic activity; a promoter mutation, i.e., a mutation in a promoter sequence, usually 5' to the transcription start site of a gene, which results in down-regulation of a specific gene product; a regulatory mutation, i.e., a mutation in a region upstream or downstream, or within a gene, which affects the expression of the gene product; a deletion mutation, i.e., a mutation which deletes coding nucleic acids in a gene sequence and which may result in a frameshift mutation or an in-frame mutation (within the coding sequence, deletion of one or more amino acid codons); an insertion mutation, i.e., a mutation which inserts coding or non-coding nucleic acids into a gene sequence, and which may result in a frameshift mutation or an in-frame insertion of one or more amino acid codons; an inversion, i.e., a mutation which results in an inverted coding or non-coding sequence; a splice mutation, i.e., a mutation which results in abnormal splicing or poor splicing; and a duplication mutation, i.e., a mutation which results in a duplicated coding or non-coding sequence, which can be in-frame or can cause a frameshift.

As used herein the phrase "loss-of-function mutation" refers to a mutation which abolishes at least one activity of a polypeptide. It should be noted that the mutation can be detected at the DNA level and/or at the protein level. Those of ordinary skills in the art can translate the effect of a nucleic acid variation in a polynucleotide-of-interest on the encoded polypeptide using the Genetic Code Table.

Various computer programs are available to predict the effect of an amino acid sequence variation on the predicted structure-function of the polypeptide. These include, for example, protein modeling software such as TMhMM [Hypertext Transfer Protocol://World Wide Web (dot) cbs (dot) dtu (dot) dk/services/TMHMM-2.0/] (see for example, FIGS. 4A-D, Example 4 of the Examples section which follows), and PDBeXplore, PDBePISA and PDBeMotif, which can be found at Hypertext Transfer Protocol://World Wide Web (dot) ebi (dot) ac (dot) uk/Tools/structural (dot) html. Pair wise and multiple sequence alignments may also be used to identify mutations in conserved amino acids and can be found at Hypertext Transfer Protocol://World Wide Web (dot) ebi (dot) ac (dot) uk/Tools/.

As described in Example 4 of the Examples section which follows, the present inventors have uncovered that the polypeptide encoded by the pH gene is a transmembrane protein which likely transports protons to the plant vacuoles and thereby increases acidity of the plant.

According to some embodiments the "loss-of-function" mutation abolishes at least about 10%, at least about 20%, at least about 30%, at least about 40%, 50%, at least about 60%, at least about 70%, at least about 80%, at least about 90%, at least about 95%, e.g., at least about 96%, 97%, 98%, 99% or 100% of the enzymatic activity of the polypeptide as measured using a suitable assay such as an enzymatic activity assay, or a protein expression assay (which indirectly reflecting activity).

Methods of qualifying the degree of the transport activity of the polypeptide of some embodiments of the invention are known in the art and include cloning of the mutated coding sequence into an expression vector (e.g., pYES) and transfecting yeast cells. The cells can be further subjected to various assays which determine the proton-dependent transfer activity of the mutated protein as compared to the non-mutated (e.g., wild-type) polypeptide, as described, for example, for the pH dependent nucleoside transporter from *Arabidopsis* in Wormit et al., 2004 [Characterization of three novel members of the *Arabidopsis thaliana* equilibrative nucleoside transporter family. Biochem. J. 383:19-26], which is fully incorporated herein by reference in its entirety.

According to some embodiments of the invention, the loss-of-function mutation occurs in the third transmembrane domain of the isolated polypeptide of some embodiments of the invention.

According to some embodiments of the invention, the loss-of-function mutation is in a transmembrane domain and may affect protein localization, protein-protein interaction, signal transduction and the like.

According to some embodiments of the invention, the loss-of-function mutation occurs in an amino acid sequence of the isolated polypeptide of the invention which is homologous to amino acids 107-110 of SEQ ID NO:4.

According to some embodiments of the invention, the loss-of-function mutation is identified on DNA of the plurality of plants.

According to some embodiments of the invention, the loss-of-function mutation is selected from the group consisting of a nonsense mutation, a frameshift mutation, an insertion, a duplication mutation or a deletion mutation.

To determine nucleic acid or amino acid sequence alterations [e.g., a single nucleotide polymorphism (SNP)] in the pH gene, DNA is first obtained from a plant tissue. Non-limiting examples of suitable plant tissues include, leaves, roots, petal, flower, fruit, seed, and roots.

Once the plant sample is obtained, DNA is extracted using methods which are well known in the art, such as by tissue mincing, cell lysis, protein extraction and DNA precipitation using 2 to 3 volumes of 100% ethanol, rinsing in 70% ethanol, pelleting, drying and resuspension in water or any other suitable buffer (e.g., Tris-EDTA). According to some embodiments of the invention, following such procedure, DNA concentration is determined such as by measuring the optical density (OD) of the sample at 260 nm (wherein 1 unit OD=50 µg/ml DNA). To determine the presence of proteins in the DNA solution, the OD 260/OD 280 ratio is determined. Preferably, only DNA preparations having an OD 260/OD 280 ratio between 1.8 and 2 are used in the following procedures described hereinbelow.

It should be noted that for PCR-based detection methods, the DNA comprised in the plant tissue need no further purification, and once the tissue is boiled, it can further be subjected to protein digestion (e.g., using alkaline phosphatase), following which the DNA is directly sampled and used in a PCR amplification reaction.

The nucleic acid sequence alteration (e.g., SNP) of some embodiments of the invention can be identified using a variety of methods. One option is to determine the entire gene sequence of a PCR reaction product (see sequence analysis, hereinbelow). Alternatively, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or the precise nucleotide sequence can be determined by partial chemical degradation or by primer extension in the presence of chain-terminating nucleotide analogs.

Additionally or alternatively, the nucleic acid sequence variation can be detected by Restriction fragment length polymorphism (RFLP); direct determination of the identity of the nucleotide at the alteration site by a sequencing assay, an enzyme-based mismatch detection assay, or a hybridization assay; Microsequencing analysis; Mismatch detection assays based on polymerases and ligases (the "Oligonucleotide Ligation Assay" (OLA, Nickerson et al. (1990) Proc. Natl. Acad. Sci. U.S.A. 87:8923-8927); ligase/Polymerase-mediated Genetic Bit Analysis™; Hybridization Assay Methods such as PCR, RT-PCR, RNase protection, in-situ hybridization, primer extension, Southern blot, Northern Blot and dot blot analysis; Hybridization to oligonucleotide arrays [see Hacia et al., (1996) Nat Genet. 1996; 14(4):441-447; Shoemaker et al., (1996) Nat Genet. 1996; 14(4):450-456; Kozal et al., (1996) Nat Med 1996; 2(7):753-759]; Integrated Systems (e.g., as described in U.S. Pat. No. 5,589,136, which describes the integration of PCR amplification and capillary electrophoresis in chips, which is fully incorporated herein by reference); Allele specific oligonucleotide (ASO; as described e.g., in Conner et al., Proc. Natl. Acad. Sci., 80:278-282, 1983, which is fully incorporated herein by reference); Denaturing/Temperature Gradient Gel Electrophoresis (DGGE/TGGE); Single-Strand Conformation Polymorphism (SSCP) reviewed by Hayashi, PCR Meth. Appl., 1:34-38, 1991, which is fully incorporated herein by reference); Dideoxy fingerprinting (ddF) (e.g., as described in Liu and Sommer, PCR Methods Appli., 4:97, 1994, which is fully incorporated herein by reference); Pyrosequencing™ analysis (Pyrosequencing, Inc. Westborough, Mass., USA); Acycloprime™ analysis (Perkin Elmer, Boston, Mass., USA); and Reverse dot blot.

It will be appreciated that advances in the field of SNP detection have provided additional accurate, easy, and inexpensive large-scale SNP genotyping techniques, such as dynamic allele-specific hybridization (DASH, Howell, W. M. et al., 1999. Dynamic allele-specific hybridization (DASH). Nat. Biotechnol. 17: 87-8), microplate array diagonal gel electrophoresis [MADGE, Day, I. N. et al., 1995. High-throughput genotyping using horizontal polyacrylamide gels with wells arranged for microplate array diagonal gel electrophoresis (MADGE). Biotechniques. 19: 830-5], the TaqMan system (Holland, P. M. et al., 1991. Detection of specific polymerase chain reaction product by utilizing the 5'→3' exonuclease activity of *Thermus aquaticus* DNA polymerase. Proc Natl Acad Sci USA. 88: 7276-80), as well as various DNA "chip" technologies such as the GeneChip microarrays (e.g., Affymetrix SNP chips) which are disclosed in U.S. Pat. No. 6,300,063 to Lipshutz, et al. 2001, which is fully incorporated herein by reference, Genetic Bit Analysis (GBA™) which is described by Goelet, P. et al. (PCT Appl. No. 92/15712), peptide nucleic acid (PNA, Ren B, et al., 2004. Nucleic Acids Res. 32: e42) and locked nucleic acids (LNA, Latorra D, et al., 2003. Hum. Mutat. 22: 79-85) probes, Molecular Beacons (Abravaya K, et al., 2003. Clin Chem Lab Med. 41: 468-74), intercalating dye [Germer, S, and Higuchi, R. Single-tube genotyping without oligonucleotide probes. Genome Res. 9:72-78 (1999)], FRET primers (Solinas A et al., 2001. Nucleic Acids Res. 29: E96), AlphaScreen (Beaudet L, et al., Genome Res. 2001, 11(4): 600-8), SNPstream (Bell P A, et al., 2002. Biotechniques. Suppl.: 70-2, 74, 76-7), Multiplex minisequencing (Curcio M, et al., 2002. Electrophoresis. 23: 1467-72), SnaPshot (Turner D, et al., 2002. Hum Immunol. 63: 508-13), MassEXTEND (Cashman J R, et al., 2001. Drug Metab Dispos. 29: 1629-37), GOOD assay (Sauer S, and Gut I G. 2003. Rapid Commun. Mass. Spectrom. 17: 1265-72), Microarray minisequencing (Liljedahl U, et al., 2003. Pharmacogenetics. 13: 7-17), arrayed primer extension (APEX) (Tonisson N, et al., 2000. Clin. Chem. Lab. Med. 38: 165-70), Microarray primer extension (O'Meara D, et al., 2002. Nucleic Acids Res. 30: e75), Tag arrays (Fan J B, et al., 2000. Genome Res. 10: 853-60), Template-directed incorporation (TDI) (Akula N, et al., 2002. Biotechniques. 32: 1072-8), fluorescence polarization (Hsu T M, et al., 2001. Biotechniques. 31: 560, 562, 564-8), Colorimetric oligonucleotide ligation assay (OLA, Nickerson D A, et al., 1990. Proc. Natl. Acad. Sci. USA. 87: 8923-7), Sequence-coded OLA (Gasparini P, et al., 1999. J. Med. Screen. 6: 67-9), Microarray ligation, Ligase chain reaction, Padlock probes, Rolling circle amplification, Invader assay (reviewed in Shi M M. 2001. Enabling large-scale pharmacogenetic studies by high-throughput mutation detection and genotyping technologies. Clin Chem. 47: 164-72), coded microspheres (Rao K V et al., 2003. Nucleic Acids Res. 31: e66) MassArray (Leushner J, Chiu N H, 2000. Mol. Diagn. 5: 341-80), heteroduplex analysis, mismatch cleavage detection, and other conventional techniques as described in Sheffield et al. (1991), White et al. (1992), Grompe et al. (1989 and 1993), exonuclease-resistant nucleotide derivative (U.S. Pat. No. 4,656,127).

Sequence alterations can also be determined at the protein level. While chromatography and electrophoretic methods are preferably used to detect large variations in the molecular weight of the polypeptide of some embodiments of the invention, such as detection of the truncated protein generated by a frameshift, deleted or non-sense sequence alteration, immunodetection assays such as ELISA and western blot analysis, immunohistochemistry and the like, which may be effected using antibodies specific to sequence alterations are preferably used to detect point mutations and subtle changes in molecular weight.

The polynucleotides and polypeptides described hereinabove can be used in a wide range of economical plants, in a safe and cost effective manner.

Plant lines exogenously expressing the polynucleotide or the polypeptide of the invention are screened to identify those that show the greatest increase of the desired plant trait.

According to an aspect of some embodiments of the invention, there is provided a food or feed comprising the plant of some embodiments of the invention or a part thereof.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Maliga P. et al., (1995) Methods in Plant Molecular Biology: A Laboratory Course Manual (A Cold Spring Harbor Laboratory Course Manual); Clark, M. (1996) Plant Molecular Biology: A Laboratory Manual (Springer Lab Manuals). Other general references are provided throughout this document. The procedures therein are believed to be well known in the art and are provided for the convenience of the reader. All the information contained therein is incorporated herein by reference.

Example 1

Identification of the pH Gene Using Map-Based Cloning

The present inventors have mapped the gene responsible for controlling acidity (pH) in a plant using a fine mapping strategy (see e.g., Peters J. et al., 2003, Trends in Plant Science, 8:484-491). The novel gene was cloned using segregating populations of melon, which were derived from crosses between sour and non-sour genotypes. The populations were selected from a Random Introgression Line population derived from a cross of the non-sour variety Dulce and a sour genotype PI414723, as well as near-isogenic lines derived from a cross of the sour Faqqus variety and the non-sour Noy Yizre'el variety. The technique used to span the introgression was selected from BAC (bacterial artificial chromosome) walking and marker development and a combination of techniques thereof. By identifying polymorphisms and correlating them with the phenotype of fruit acidity, the introgression controlling fruit acidity was limited to ~40 kb of genomic sequence. This introgression contained a candidate gene for the trait of fruit acidity, which encodes for an undefined membrane transporter.

Experimental Results

Mapping of the Gene Controlling pH in Plants—Recombinant inbred lines (RIL) were generated by crossing the Dulce (non-sour) and PI414723 (sour) melon parental lines and by subsequent selfing of the F2, F3, F4 and F5 generations thereof, as described in Harel-Beja et al., 2010, Theor Appl Genet., 121:511-33. Epub 2010 Apr. 17. The acidity levels of the RILs' fruits were tested for linkage analysis with polymorphic markers mapped over the genomes of the various RILs, as described in Harel-Beja et al. The pH values of the RILs and of the parental lines are provided in Table 1, hereinbelow. Each RILs line was analyzed in up to four replications.

TABLE 1

| RIL | pH |
|---|---|
| 1 | 6.39 |
| 1 | 6.32 |
| 1 | 6.54 |
| 1 | 6.55 |
| 2 | 5.1 |
| 2 | 5.2 |
| 2 | 6.35 |
| 2 | 6.1 |
| 3 | 6.59 |
| 3 | 4.8 |
| 4 | 6.3 |
| 4 | 6.2 |
| 5 | 6.73 |
| 6 | 5.7 |
| 6 | 5.7 |
| 6 | 5.2 |
| 6 | 5 |
| 6 | 4.7 |
| 7 | 5.6 |
| 7 | 6.1 |
| 7 | 5.7 |
| 9 | 5.7 |
| 9 | 6.32 |
| 9 | 6.04 |
| 10 | |
| 10 | 4.9 |
| 10 | 4.8 |
| 11 | 6.24 |
| 11 | 6.4 |
| 11 | 6.6 |
| 11 | 6.4 |
| 12 | 6.05 |
| 12 | 5.79 |
| 13 | 5.2 |
| 13 | 5.0 |
| 13 | 5.0 |
| 13 | 5 |
| 13 | 4.8 |
| 14 | 5.6 |
| 14 | 5.8 |
| 14 | 6.1 |
| 15 | 4.5 |
| 15 | 5.0 |
| 15 | 4.65 |
| 15 | 4.8 |
| 16 | 5.1 |
| 16 | 4.9 |
| 16 | 5.1 |
| 16 | 4.8 |
| 17 | 4.8 |

TABLE 1-continued

| RIL | pH |
|---|---|
| 17 | 5.2 |
| 17 | 4.7 |
| 17 | 4.9 |
| 18 | 6.18 |
| 18 | 6.1 |
| 18 | 6.3 |
| 18 | 6.41 |
| 19 | 4.45 |
| 19 | 5.85 |
| 19 | 4.9 |
| 19 | 5.9 |
| 20 | 4.8 |
| 20 | 5.3 |
| 20 | 4.8 |
| 20 | 4.8 |
| 20 | 4.8 |
| 21 | 6.0 |
| 21 | 6.2 |
| 21 | 6.3 |
| 21 | 6.1 |
| 22 | 5.07 |
| 22 | 5.2 |
| 22 | 5.26 |
| 23 | 4.88 |
| 23 | 5 |
| 23 | 4.8 |
| 23 | 4.95 |
| 24 | 6 |
| 24 | 6 |
| 24 | 5.92 |
| 24 | 6.07 |
| 25 | 4.8 |
| 25 | 4.85 |
| 25 | 4.9 |
| 26 | 6.3 |
| 26 | 6.08 |
| 26 | 6.3 |
| 26 | 6.4 |
| 27 | 5.9 |
| 27 | 6.18 |
| 27 | 6.1 |
| 27 | 5.9 |
| 28 | 6 |
| 28 | 6 |
| 28 | 6.6 |
| 29 | 4.8 |
| 29 | 4.6 |
| 29 | 4.7 |
| 30 | 6.0 |
| 30 | 5.6 |
| 30 | 5.3 |
| 30 | 5.9 |
| 31 | 4.65 |
| 31 | 4.7 |
| 31 | 4.8 |
| 31 | 5.29 |
| 31 | 5.30 |
| 31 | 5.30 |
| 32 | 6.3 |
| 32 | 6 |
| 32 | 6.1 |
| 32 | 6 |
| 34 | 6.1 |
| 34 | 6 |
| 34 | 6.1 |
| 35 | 5.6 |
| 35 | 5.6 |
| 35 | 5.6 |
| 35 | 5.2 |
| 36 | 6.1 |
| 36 | 5.7 |
| 36 | 6.06 |
| 36 | 6.01 |
| 37 | 4.5 |
| 37 | 4.77 |
| 37 | 4.9 |
| 37 | 5 |
| 38 | 6.08 |
| 38 | 6.4 |
| 38 | 6.3 |
| 38 | |
| 39 | 6.23 |
| 39 | 6.24 |
| 39 | 6.18 |
| 39 | 5.8 |
| 40 | 6.35 |
| 40 | 6.23 |
| 40 | 6.16 |
| 40 | 6.25 |
| 41 | 5.7 |
| 41 | 5.6 |
| 41 | 5.9 |
| 41 | 5.8 |
| 41 | 5.7 |
| 41 | 5.8 |
| 41 | 5.8 |
| 42 | 4.98 |
| 42 | 4.9 |
| 42 | 4.94 |
| 42 | 5.1 |
| 43 | 5.7 |
| 43 | 5.8 |
| 43 | 5.8 |
| 44 | 4.5 |
| 44 | 4.8 |
| 44 | 4.8 |
| 44 | 4.7 |
| 44 | 4.60 |
| 45 | 5.0 |
| 45 | 5.2 |
| 45 | 5.32 |
| 45 | 4.93 |
| 46 | 5.0 |
| 46 | 4.75 |
| 46 | 5.1 |
| 48 | 5.5 |
| 48 | 5.4 |
| 48 | 5.6 |
| 48 | 5.5 |
| 49 | 5.84 |
| 49 | 5.91 |
| 49 | 5.74 |
| 49 | 5.86 |
| 50 | 5.9 |
| 50 | 5.9 |
| 50 | 5.8 |
| 50 | 5.8 |
| 50 | 6 |
| 51 | 5.0 |
| 51 | 5.1 |
| 51 | 4.89 |
| 52 | 6.3 |
| 52 | 6.21 |
| 53 | 4.72 |
| 53 | 4.73 |
| 53 | 4.65 |
| 53 | 4.63 |
| 54 | 4.85 |
| 54 | 4.74 |
| 54 | 4.93 |
| 54 | 4.8 |
| 54 | 4.8 |
| 55 | 5.0 |
| 55 | 5.12 |
| 55 | 4.9 |
| 55 | 4.94 |
| 61 | 6.3 |
| 61 | 5.7 |
| 61 | 5.5 |
| 61 | 5.6 |
| 62 | 5.8 |
| 62 | 6.28 |
| 62 | 6.43 |
| 62 | 6.4 |
| 62 | 6.13 |
| 63 | 6.0 |

TABLE 1-continued

| RIL | pH |
|---|---|
| 63 | 6.2 |
| 63 | 6 |
| 63 | 5.9 |
| 64 | 4.63 |
| 64 | 4.65 |
| 64 | 4.83 |
| 64 | 4.71 |
| 65 | 6.1 |
| 65 | 6.02 |
| 65 | 6.09 |
| 65 | 5.7 |
| 66 | 5.08 |
| 66 | 4.8 |
| 66 | 4.7 |
| 68 | 6.2 |
| 68 | 6.3 |
| 68 | 6.3 |
| 68 | 6.1 |
| 69 | 6.55 |
| 69 | 5.7 |
| 69 | 6.3 |
| 69 | 6.2 |
| 69 | 6.5 |
| 71 | 4.72 |
| 71 | 4.6 |
| 71 | 4.85 |
| 71 | 5 |
| 72 | 6.2 |
| 72 | 6.4 |
| 72 | 6.51 |
| 72 | 6.47 |
| 73 | 6 |
| 73 | 6.2 |
| 73 | 6.32 |
| 73 | 6.2 |
| 74 | 6 |
| 74 | 5.9 |
| 76 | 4.7 |
| 76 | 5 |
| 76 | 4.9 |
| 76 | 4.8 |
| 77 | 6.3 |
| 77 | 6.3 |
| 77 | 5.9 |
| 77 | 5.7 |
| 79 | 5.4 |
| 79 | 5.2 |
| 79 | 4.92 |
| 79 | 5.3 |
| 79 | 5.25 |
| 79 | 5.4 |
| 79 | 5.2 |
| 80 | 5.8 |
| 80 | 5.6 |
| 80 | 5.2 |
| 80 | 5.79 |
| 81 | 5.12 |
| 81 | 5 |
| 81 | 5.07 |
| 81 | 4.88 |
| 82 | 6.3 |
| 82 | |
| 83 | 4.9 |
| 83 | 4.6 |
| 83 | 4.7 |
| 83 | 4.88 |
| 84 | 6.0 |
| 84 | 6.1 |
| 84 | 5.9 |
| 84 | 6 |
| 84 | 5.9 |
| 85 | 5.80 |
| 85 | 5.65 |
| 85 | 5.7 |
| 85 | 4.8 |
| 87 | 5.06 |
| 87 | 4.9 |
| 87 | 5 |
| 89 | 6.30 |
| 89 | 5.90 |
| 89 | 6.11 |
| 91 | 5.33 |
| 91 | 4.80 |
| 91 | 5.20 |
| 91 | 4.8 |
| 91 | 5.1 |
| 92 | 4.50 |
| 92 | 4.90 |
| 92 | 4.50 |
| 92 | 4.80 |
| 92 | 4.6 |
| 92 | 4.6 |
| 92 | 5 |
| 92 | 4.6 |
| 93 | 5.20 |
| 93 | 4.65 |
| 93 | 4.80 |
| 93 | 4.70 |
| 93 | 4.65 |
| 93 | 4.65 |
| 93 | 4.8 |
| 93 | 4.9 |
| 94 | 5.9 |
| 94 | 5.97 |
| 94 | 4.8 |
| 94 | 5.97 |
| 95 | 5.08 |
| 95 | 5.10 |
| 95 | 5.2 |
| 95 | 4.9 |
| 96 | 5.00 |
| 96 | 5.30 |
| 96 | 5.45 |
| 97 | 6.61 |
| 97 | 6.37 |
| 97 | 6.30 |
| 97 | 6.30 |
| 98 | 4.70 |
| 98 | 4.50 |
| 98 | 4.9 |
| 98 | 4.9 |
| 99 | 5.00 |
| 99 | 5 |
| 99 | 5.30 |
| 99 | 4.84 |
| 100 | 4.80 |
| 100 | 4.60 |
| 100 | 4.7 |
| 101 | 4.8 |
| 101 | 4.8 |
| 102 | 5.22 |
| 102 | 5.35 |
| 102 | 5.15 |
| 102 | 5 |
| 103 | 6.40 |
| 103 | 5.13 |
| 103 | 5.08 |
| 107 | 5.00 |
| 107 | 5.00 |
| 107 | 5.13 |
| 107 | 4.84 |
| 108 | 5.13 |
| 108 | 4.56 |
| 108 | 4.9 |
| 108 | 4.86 |
| 110 | 6.51 |
| 110 | 6.21 |
| 111 | 6.33 |
| 111 | 6.1 |
| 111 | 6.18 |
| 111 | 6.70 |
| 113 | 4.77 |

TABLE 1-continued

| RIL | pH |
|---|---|
| 113 | 4.85 |
| 114 | 4.9 |
| 114 | 4.7 |
| 114 | 4.6 |
| 115 | 4.9 |
| 115 | 5.3 |
| 115 | 5.0 |
| 115 | 4.8 |
| 115 | 5 |
| 115 | 4.9 |
| 117 | 5.12 |
| 117 | 4.76 |
| 117 | 4.7 |
| 117 | 5.06 |
| 117 | 4.7 |
| mean | 5.5 |
| SDEV | 0.6 |
| max | 6.7 |
| min | 4.5 |
| D1 | 6.00 |
| D1 | 6.40 |
| D1 | 6.3 |
| D1 | 6.1 |
| D1 | 6.00 |
| D2 | 6.44 |
| D2 | 6.50 |
| D2 | 6.20 |
| D2 | 6.25 |
| D2 | 6.69 |
| D3 | 6.3 |
| D3 | 6.0 |
| D3 | 6.2 |
| D3 | 6.4 |
| mean | 6.3 |
| SDEV | 0.2 |
| P1 | 5 |
| P1 | |
| P2 | 4.80 |
| P2 | 5.10 |
| P3 | 4.80 |
| P3 | 4.70 |
| P3 | 4.9 |
| mean | 4.9 |
| SDEV | 0.1 |
| P2 | 4.9 |
| P3 | 4.85 |
| 'Dulce' mean ± SD | 6.3 ± 0.2 |
| PI 414723 mean ± SD | 4.9 ± 0.1 |

Table 1. Provided are the RIL numbers and the pH values of each of the RILs and parental lines 'Dulce' and "PI 414723" tested.

Cloning of the pH Gene—The gene responsible for controlling the acidity (pH) of the fruit had been mapped to a position between the CMAT141 and CMCTTN181 markers, at a genetic distance of 2 and 3 centimorgan (cM), respectively from the pH trait (Harel-Beja et al. 2010). The pH gene was cloned by a mapped based cloning approach using the strategy of chromosome walking (see e.g., Peters J. et al., 2003, Trends in Plant Science, 8:484-491). For physical mapping of the pH gene, filters from a melon genomic BAC (bacterial artificial chromosome) library CM_MBaB (Clemson University Genomic Institute, USA) were screened with radioactive probes labeled using the NEBlot™ Kit (#N1500S) (New England BioLabs, Inc.) according to the supplier's instructions. Labeled BAC colonies on filters were detected using a Fuji Film phosphoimager (FLA-5000). For the development of the contiguous BAC series, the selected BACs were end-sequenced using SP6 and T7 primers and a PCR product was developed from these end sequences. The purified PCR product was labeled as above and used as a probe for the identification of the contiguous BACs. Analysis of polymorphisms between the two parental lines for each new sequence obtained together with the comparison of the polymorphisms with those of the RILs lines allowed for the limitation of the introgression to BAC CM_MBaB 69P20 which harbored the putative pH gene, as determined by sequencing.

In order to compare the sequences of the pH gene from sour and non-sour melons, RNA was extracted from two parental lines of melon: the sour melon variety C. melo var. PI414723 and the non-sour melon variety C. melo var. Dulce (described in Harel-Beja et al. 2010, Theor Appl Genet., 121:511-33) and was used to produce cDNA and clone the pH gene using the following primers: Melon transporter Forward: 5'-ATG GAC ATG GAA AGA TTT CTC T (SEQ ID NO:7); and Melon transporter Reverse: 5'-TTA-GAAGAGTATCCTGAAGTAGA (SEQ ID NO:11). DNA was sequenced using the ABI sequencer (Hylabs, Inc., Rehovot, Israel). The cloned DNA sequences were analyzed and translated to amino acids using DNAMAN program (version 4.20). The cloned DNA sequences of the sour and non-sour varieties are presented in FIGS. 1A and 1C, respectively. The amino acid sequences of the sour and non-sour varieties are presented in FIGS. 1B and 1D, respectively. The genomic sequence of the pH gene from non-sour melon was identified based on the sequencing of BAC CM_MBaB 69P20 (SEQ ID NO:14). This sequence was not annotated before, and only a partial sequence thereof was available [Melon Unigene ID: MU46248; World Wide Web (dot) icugi (dot) org], yet without any specific annotation.

Identification of Homologues in Tomatoes and Cucumbers—Subsequent genomic analysis revealed that homologues to the pH gene are found in tomatoes and cucumber and lie on chromosomal locations SL2.40ch10: 57831763 . . . 57835784 in tomatoes [via Hypertext Transfer Protocol://solgenomics (dot) net/] and on chromosome No. 4: 12462425 . . . 12456602 in cucumbers [via Hypertext Transfer Protocol://World Wide Web (dot) icugi (dot) org/].

Example 2

Identification of a Duplication Mutation which Modifies the pH of Melon Fruits

Comparative sequencing of the novel pH gene from the acid and non-acid genotypes indicated that the non-acid sequence contained a 12 bp duplication, which encoded for a duplication of four amino acids in the derived protein.

Experimental Results

The present inventors have compared the sequence of the sour genotype with that of a sweet cultivated genotype (Dulce) and observed a duplication of four amino acids in part of the hydrophobic transmembrane span #3, as follows.

Identification of a Duplication Mutation Present in Non-Sour Melons—Sequence alignment between the amino acid sequence encoded by the pH gene from sour (SEQ ID NO:2) and non-sour (SEQ ID NO:4) melon varieties revealed that the sequences are identical except for the presence of a four-amino acid duplication "LIVA" (SEQ ID NO:27) at amino acid positions 107-110 of SEQ ID NO:4, which appears in the non-sour melon variety and which is absent from the sour melon variety (FIG. 1E).

Example 3

Similarity and Identity of the pH Gene Between Various Plants

Bioinformatics Analysis

Comparison of the Sequence of the Protein Encoded by the Melon pH Gene with Homologous from Additional Plants—Multiple sequence alignment was performed on sequences derived from Tomato TC200226 (SEQ ID NO:5; FIG. 2A), Cucumber Csa01116 (SEQ ID NO:6; FIG. 2B), apple TC80539 (SEQ ID NO:8, FIG. 2D), Poplar EEF05451 (SEQ ID NO:9; FIG. 2E), and *Arabidopsis* NP_195819 (SEQ ID NO:10, FIG. 2F) and the protein sequences from these species were compared to that of sour and non-sour melons using the Clustal 2W program alignment. As shown in FIG. 3 and in Tables 2-3 hereinbelow, sequences of the pH gene from all plant species exhibit high homology to the pH gene from the sour melon. In addition, the LIVA duplication was found only in the pH gene from non-sour melon (FIG. 3).

The sequences, which were used for multiple alignments, are provided in Table 2, hereinbelow.

TABLE 2

Table 2. Sequence type explicitly set to Protein. Sequence format is Pearson.

| | |
|---|---|
| Sequence 1: Sour_Melon | 411 aa SEQ ID NO: 2 |
| Sequence 2: Tomato_TC200226 | 424 aa SEQ ID NO: 5 |
| Sequence 3: Cucumber_Csa01116 | 453 aa SEQ ID NO: 6 |
| Sequence 4: Poplar_EEF05451 | 414 aa SEQ ID NO: 9 |
| Sequence 5: apple|TC84138 | 432 aa SEQ ID NO: 28 |
| Sequence 7: melon | 419 aa SEQ ID NO: 4 |
| Sequence 9: grape|TC118456 | 376 aa SEQ ID NO: 29 |

Tables 3 and 4 depict the percent (%) similarity (Table 3) and identity (Table 4) between of 6 full amino acid sequences using the BLOSSUM NEEDLE pairwise alignment program [Hypertext Transfer Protocol://World Wide Web (dot) ebi (dot) ac (dot) uk/Tools/psa/emboss_needle/].

TABLE 3 percentage similarity

| | sour melon | tomato | cucumber | poplar | apple | grape |
|---|---|---|---|---|---|---|
| sour melon | 100 | 82.3 | 89.6 | 86.7 | 81.6 | 81 |
| tomato | | 100 | 75.3 | 83.8 | 80.4 | 76.9 |
| cucumber | | | 100 | 78.3 | 77.8 | 73.7 |
| poplar | | | | 100 | 85.1 | 81.9 |
| apple | | | | | 100 | 77.5 |
| grape | | | | | | 100 |

Table 3: Percent similarity (derived from EMBOSS NEEDLE program of pairwise alignment).

TABLE 4 percentage identity

| | sour melon | tomato | cucumber | poplar | apple | grape |
|---|---|---|---|---|---|---|
| sour melon | 100 | 69.1 | 87.9 | 79 | 70.8 | 69.8 |
| tomato | | 100 | 62.7 | 70.7 | 66.6 | 62 |
| cucumber | | | 100 | 70.9 | 66 | 62.5 |
| poplar | | | | 100 | 77.8 | 72.9 |
| apple | | | | | 100 | 66 |
| grape | | | | | | 100 |

Table 4: Percent identity (derived from EMBOSS NEEDLE program of pairwise alignment).

Identity and similarity were measured using the EMBOSS NEEDLE program using default parameters: Matrix: BLOSUM62; GAP OPEN: 10; GAP extend: 0.5; Output format: pair; END GAP penalty: false; ENP GAP OPEN: 10; END GAP extend: 0.5.

It is noted that the % identity and % similarity between cucumber and tomato are 62.7 and 75.3, respectively.

Example 4

The LIVA Duplication is Predicted to Change the Conformation of the pH Protein Protein modeling analysis TMHMM [Hypertext Transfer Protocol://World Wide Web (dot) cbs (dot) dtu (dot) dk/services/TMHMM-2.0/], which compares between the pH protein from sour and non-sour melons, revealed that the pH gene from sour melon encodes for a membrane protein with 10 transmembrane helical domains (THDs) (FIGS. 4A and B), which is indicative of membrane transporters. In contrast, protein modeling of the sequence derived from non-sour melon (having the LIVA duplication) reveals presence of only 9 THDs, with a flipped direction of the protein (inside and outside) as compared to the sequence from sour melon (FIGS. 4C and D), which would lead to a defective protein.

Example 5

Correlation Between Presence of the "LIVA" Duplication Mutation and the pH of Fruits in Additional Melon Varieties Experimental Results Determining the Genotype of the pH Gene Among Sour and Non-Sour Melon Varieties—DNA from 52 varieties of *C. melon* was extracted from leaves of young plantlets. Genotyping was based on DNA-PCR analysis using the following primers: Forward primer: 5'-CTCGGGCAAGC-TATTACT (SEQ ID NO:12); and Reverse primer: 5'-GTATGGAGGACGAACAAT (SEQ ID NO:13), which distinguish between the two alleles of the pH gene which include or not the 12 base-pair (bp) duplication as shown in a representative gel in FIG. 5 and in Table 5 below which summarizes the genotyping results for the 20 samples shown in FIG. 5.

TABLE 5 genotyping for the LIVA duplication in melon varieties

| | Melon Variety Name | Fruit pH | Genotype of the pH gene |
|---|---|---|---|
| 1 | PSR | 6.1 | 2 |
| 2 | TVT | 6.1 | 2 |
| 3 | HBJ | 6.6 | 2 |
| 4 | PI 157080 | 5.7 | 2 |
| 5 | INB | 6 | 2 |
| 6 | PDS | 5.9 | 2 |
| 7 | ESL | 5.9 | 2 |

TABLE 5-continued genotyping for the LIVA duplication in melon varieties

| | Melon Variety Name | Fruit pH | Genotype of the pH gene |
|---|---|---|---|
| 8 | PI 157071 | 6.2 | 1 |
| 9 | KRY | 7.3 | 2 |
| 10 | CHT | 6.3 | 2 |
| 11 | CHF | 6.8 | 2 |
| 12 | DUD2 | 5.9 | 2 |
| 13 | DUD3 | 6.2 | 2 |
| 14 | MAK | 7.1 | 2 |
| 15 | OGE | 5.9 | 2 |
| 16 | PH406 | 6 | 2 |
| 17 | Blank lane | | |
| 18 | Rochet | 6.7 | 2 |
| 19 | Dulce control | | 2 |
| 20 | PI414723 control | | 1 |

Table 5: genotyping results of the samples shown in FIG. 5. Genotypes were scored as "1" (small band, 125 bp) or "2" (larger band, 137 bp).

Classification of Fruits as Sour or Non-Sour Based on pH Levels—pH of ripe fruit (average of 3 fruit) of each variety was measured on extracted juice from the flesh of ripe fruit and measured using a standard laboratory pH meter which was calibrated using commercial solutions of pH 4 and pH 7.

Correlation Between Genotype and Phenotype in Melon Varieties—A survey of 42 accessions of *C. melo*, representing the broad spectrum of the species showed that all non-sour melon genotypes are characterized by the identical mutation irrespective of geographical origin or systematic classification. The sour genotypes are all characterized by the absence of the duplication, similarly irrespective of geographical origin or systematic classification. Table 6, hereinbelow, provides genotyping data for 42 melon varieties along with the correlation to fruit's acidity (pH values).

TABLE 6

| Subspecies | Variety Group | Market class | Variety Name | Melon Variety Name | Fruit pH | Genotype of the pH gene |
|---|---|---|---|---|---|---|
| *melo* | *Flexuosus* | Snake melon, Pickling melon | Faqqous Doya | DOYA | 4.6 | 1 |
| *agrestis* | *Conomon* | ? | Freeman Cucumber | FRC 37 | 4.9 | 1 |
| *melo* | *Flexuosus* | Snake melon, Pickling melon | Faqqous | FAQ | 4.8 | 1 |
| *agrestis* | *Momordica* | ? | PI 414723 | PI 414 | 4.8 | 1 |
| *agrestis* | *Conomon* | ? | Tokyo Giant | TOG | 4.3 | 1 |
| *melo* | *Flexuosus* | Snake melon, Pickling melon | Armenian Yard Long | AYL | 4.8 | 1 |
| melo | Inodorus | Casaba (Piel De Sapo) | Piel De Sapo Redon | PSR | 6.1 | 2 |
| melo | Inodorus | Casaba (Negro tendral) | Tendral Verde Tardio | TVT | 6.1 | 2 |
| melo | Reticulatus | US cantaloupe | Hale's Best Jumbo | HBJ | 6.6 | 2 |
| agrestis | Makuwa | ? | PI 157080 | 157080 | 5.7 | 2 |
| melo | Chandalak | ? | Indian Best | INB | 6 | 2 |
| melo | Inodorus | Casaba (Piel De Sapo) | Piel De Sapo | PDS | 5.9 | 2 |
| agrestis | Makuwa | ? | Early Silver Line | ESL | 5.9 | 2 |
| melo | Reticulatus | Galia | Krymka | KRY | 7.3 | 2 |
| melo | Cantalupensis | Charentais | Charentais | CHT | 6.3 | 2 |
| melo | Cantalupensis | Charentais | Charentais F2 | CHF | 6.8 | 2 |
| melo | Dudaim | Dudaim | Dudaim2 | DUD2 | 5.9 | 2 |
| melo | Dudaim | Dudaim | Dudaim3 | DUD3 | 6.2 | 2 |
| melo | Reticulatus | Galia | Magyar Kines | MAK | 7.1 | 2 |
| melo | Cantalupensis | Ha'Ogen | Ogen | OGE | 5.9 | 2 |
| melo | Cantalupensis | Ha'Ogen | PH406 | PH406 | 6 | 2 |
| melo | Inodorus | Casaba (Rochet) | Rochet | Rochet | 6.7 | 2 |
| melo | Cantalupensis | Charentais | Vedrantais | VEP | 7 | 2 |
| melo | Inodorus | Casaba | Golden Beauty | GOB | 5.6 | 2 |
| melo | Cantalupensis | Charentais | Doublon | DOU | 7.2 | 2 |
| melo | Inodorus | Casaba (kirkagac) | Kirkagac | 33410 | 5.8 | 2 |
| melo | Inodorus | Casaba (Yellow canary) | Gold King | GOK | 5.8 | 2 |
| melo | Cantalupensis | Ha'Ogen | Bellegarde | BEL | 5.9 | 2 |
| melo | Inodorus | Casaba (Yellow canary) | Amarillo Oro | AROC | 6 | 2 |
| melo | Reticulatus | American cantaloupe | PMR45 | PMR45 | 6.7 | 2 |
| melo | Inodorus | Casaba (Yellow canary) | Amarillo Pipa Blanka | AMP | 5.5 | 2 |

TABLE 6-continued

| Subspecies | Variety Group | Market class | Variety Name | Melon Variety Name | Fruit pH | Genotype of the pH gene |
|---|---|---|---|---|---|---|
| melo | Reticulatus | American cantaloupe | Dulce | Dulce | 5.9 | 2 |
| melo | Reticulatus | Ananas | Ein Dor | ED | 6 | 2 |
| melo | Cantalupensis | Ha'Ogen | Noy Yizre'el | NY | 5.6 | 2 |
| melo | Reticulatus | Ananas | Ananas Yoqne'am | AY | 6.3 | 2 |
| melo | Inodorus | Casaba (kirkagac) | kirkagac | 201581 | 5.4 | 2 |
| melo | Reticulatus | American cantaloupe | Bender's Surprise | BES | 5.8 | 2 |
| agrestis | Makuwa | ? | Sakata Sweet | SAS | 6.2 | 2 |
| agrestis | Conomon | Pickling melon | Black Skin | BSK | 5.7 | 2 |
| agrestis | Chinensis | ? | PI 161375 | 161375 | 5.8 | 2 |
| melo | Reticulatus | American cantaloupe | Fordhook Gem | FOG | 5.8 | 2 |
| melo | Reticulatus | US cantaloupe | Top Mark | TPM | 6.9 | 2 |

Table 6: Provided are melon genotypes and correlation between the genotypic duplication and fruit pH. Genotypes were scored as "1" (small band, 125 bp) or "2" (larger band, 137 bp).
Bolded text—melon varieties having fruit pH below 5 (acidity; having genotype "1");
Regular text: melon varieties having fruit pH above 5 (less acid or neutral; having genotype "2").
Question marks indicate uncharacterized marketing type.

These results demonstrate that the presence or absence of the LIVA duplication mutation can be used to predict the pH levels of the melon fruit, even when testing young leaf material. In addition, the results show that the LIVA duplication mutation can be used for the breeding of sweet and sour melon varieties. Furthermore, as a paralogous gene is expressed in most fruit it is likely to contribute to fruit acidity. Therefore, the modulation of this gene in other fruit by biotechnological means will impact of the acidity of additional fruits, as well.

Example 6

Phylogenetic Relationships Among Proteins Homologous to The pH Gene

Phylogenetic relationships among proteins homologous to the pH gene—Sequence comparison with the databases places the transporter in an unknown family putatively described as auxin-proton transporter family [predicted or hypothetical proteins (XP_002326270; CBI31149 or XP_002267734) or to proteins having a putative auxin: proton symporter activity (XP_002531815) or auxin efflux carrier component of auxin transport protein (XP_002323690)]. Amino acid sequences of proteins with similarity to the CmpH (melon pH) gene were identified by searching public databases of gene sequences using the BLAST® (Basic Local Alignment Search Tool, National Library of Medicine) program. Public databases used were NCBI, ICuGI (a database of cucurbit expressed genes) and TIGR (expressed sequences from numerous plants). In addition, the gene annotation for sequences with similarity to the CmpH gene is described as "auxin efflux transporter" and members of the membrane transport family [pFAM 03547, (Hypertext Transfer Protocol://pfam (dot) sanger (dot) ac (dot) uk/family/PF03547 (dot) 12), and the Transporter Class 2.A.69 (Hypertext Transfer Protocol://World Wide Web (dot) tcdb (dot) org/search/result (dot) php?tc=2.A.69) including members of the PIN LAX families of proteins] are also included. Alignments and phylogenetic trees were determined using a public web based phylogenetic program using the one-click option (World Wide Web (dot) phylogeny (dot) fr). For the determination of Clustal similarity scores the ClustalW program [Hypertext Transfer Protocol:// World Wide Web (dot) ebi (dot) ac (dot) uk/Tools/msa/ clustalw2/]% similarity and % identity of amino acid sequences a pairwise alignment was carried on using the NEEDLE program at Hypertext Transfer Protocol://World Wide Web (dot) ebi (dot) ac (dot) uk/Tools/psa/emboss_ needle/and values determined.

As shown in FIG. 6, a clade of highly similar sequences related to the melon pH gene which separate from a closely related clade of proteins of undetermined function (which are partially annotated as "membrane transporters", "auxin transporters" or as hypothetical or putative proteins) and are more distantly related to the characterized auxin transporter families of PIN and AUX. The % similarity among members of the closely related clade of pH homologues is higher than 70%. These results conclusively show that the pH gene is distinct from the characterized functional auxin transporters of the PIN and AUX families and can only be described as membrane transporters of uncharacterized activity which determine pH or H+ concentration, thereby presumably being a family of H+ membrane transporters.

Some examples of members of this closely related clade which are expressed in plants, as indicated in the various databases of expressed genes, is presented in Table 7, below, indicating the plant and tissues in which expression has been reported. The data shows that homologues of the melon pH gene is expressed in numerous plants, including their fruit tissue and also non-fruit tissues such as leaves, flowers, roots and stems.

TABLE 7

Table 7: the expression of pH gene homologues in the respective plant tissues, as indicated in the public gene expression databases listed.

| | | TC number | expression | link |
|---|---|---|---|---|
| 1 | *Citrus sinensis* | TC5400 | Sweet orange fruit, development stadium (3 of 6)<br>*Citrus sinensis* phloem | Hypertext Transfer Protocol://compbio(dot)dfci(dot)harvard(dot)edu/cgi-bin/tgi/tc_report.pl?tc=TC5400&species=orange |
| 2 | *Vitis vinifera* | TC152595 | Developmental stage eight (DS8) RDA Berries 14 mm with GA3 (VvS7)<br>Cabernet Sauvignon Berry Stage I<br>Developmental stage eight (DS8) Veraison Grape berries<br>Flower Stage 12 (FLOu0012)<br>CabSau Flower Stage 12 (FLOu0012)<br>Cab Sauv pericarp normalized (WIN09)<br>Ripe Grape Berries | Hypertext Transfer Protocol://compbio(dot)dfci(dot)harvard(dot)edu/cgi-bin/tgi/tc_report.pl?tc=TC152595&species=grape |
| 3 | *Zea mays* | TC466250 | tassel primordium | Hypertext Transfer Protocol://compbio(dot)dfci(dot)harvard(dot)edu/cgi-bin/tgi/tc_report(dot)pl?tc=TC466250&species=maize |
| 4 | *Hordeum vulgare* | TC240224 | *Hordeum vulgare* seedling green leaf<br>Vegetative stage leaves<br>Germination shoots | Hypertext Transfer Protocol://compbio(dot)dfci(dot)harvard(dot)edu/cgi-bin/tgi/tc_report(dot)pl?tc=TC240224&species=barley |
| 5 | *Oryza sativa* | TC528572 | | Hypertext Transfer Protocol://compbio(dot)dfci(dot)harvard(dot)edu/cgi-bin/tgi/tc_report(dot)pl?tc=TC528572&species=rice |
| 6 | *Petunia hybrida* | TC12450 | normalized cDNA library of roots<br>floral post-pollination cDNA library | Hypertext Transfer Protocol://compbio(dot)dfci(dot)harvard(dot)edu/cgi-bin/tgi/tc_report(dot)pl?tc=TC12450&species=petunia |
| 7 | *Solanum lycopersicum* | TC225290 | developing/immature green fruit<br>trichomes<br>root, etiolated radicle<br>breaker fruit<br>developing/immature green fruit ovary<br>maturing fruit | Hypertext Transfer Protocol://compbio(dot)dfci(dot)harvard(dot)edu/cgi-bin/tgi/tc_report(dot)pl?tc=TC225290&species=tomato |
| 8 | *Solanum tuberosum* | TC208951 | sprouting eyes<br>roots and leaves<br>Mixed Floral | Hypertext Transfer Protocol://compbio(dot)dfci(dot)harvard(dot)edu/cgi-bin/tgi/tc_report(dot)pl?tc=TC208951&species=potato |
| 9 | *Arabidopsis thaliana* | TC370336 | 8-day *Arabidopsis* seedlings, aerial tissues | Hypertext Transfer Protocol://compbio(dot)dfci(dot)harvard(dot)edu/cgi-bin/tgi/tc_report(dot)pl?tc=TC370336&species=arab |
| 10 | *Malus × domestica* | TC84138 | root tips<br>xylem<br>partially senescing leaf | Hypertext Transfer Protocol://compbio(dot)dfci(dot)harvard(dot)edu/cgi-bin/tgi/tc_report(dot)pl?tc=TC84138&species=apple |
| 11 | *Medicago truncatula* | TC175110 | glandular trichome | Hypertext Transfer Protocol://compbio(dot)dfci(dot)harvard(dot)edu/cgi-bin/tgi/tc_report(dot)pl?tc=TC175110&species=medicago |
| 12 | *Cucumis sativus* | CU106263 | fruit, flower | Hypertext Transfer Protocol://World Wide Web (dot) icugi (dot) org/cgi-bin/ICuGI/EST/search(dot)cgi?organism=cucumber |

TABLE 7-continued

Table 7: the expression of pH gene homologues in the respective plant tissues, as indicated in the public gene expression databases listed.

| | | TC number | expression | link |
|---|---|---|---|---|
| 13 | Cucumis melo, sour | MU46248 | fruit, cotyledons, roots | &searchtype=unigene&unigene=CU106263 Hypertext Transfer Protocol://World Wide Web (dot)icugi (dot) org/cgi-bin/ICuGI/EST/search (dot) cgi?organism=melon&searchtype=unigene&unigene=MU46248 |
| 14 | Cucumis melo, non-sour | MU46248 | fruit, cotyledons, roots | Hypertext Transfer Protocol://World Wide Web (dot) icugi (dot) org/cgi-bin/ICuGI/EST/search (dot) cgi?organism=melon&searchtype=unigene&unigene=MU46248 |
| 15 | Populus sp. | TC154035 | mixture of leaf, bud, stem, root | Hypertext Transfer Protocol://compbio(dot)dfci(dot)harvard(dot)edu/cgi-bin/tgi/tc_report(dot)pl?tc=TC154035&species=poplar |

This data demonstrates that the pH gene is not limited to melon plants, and that the control of acidity in other plants is also likely affected by homologues of the pH gene.

Example 7

Silencing of the pH Gene Affects Fruit Acidity

In order to test the role of the pH gene in determining fruit acidity, transgenic plants of cucumber and of tomato were developed which had a reduced expression of the respective pH gene using the technology of RNAi. RNAi technology is a well-established technology of silencing gene expression. In short, RNAi is an RNA-dependent gene silencing process that is controlled by the RNA-induced silencing complex (RISC) and is initiated by short double-stranded RNA molecules in a cell's cytoplasm. The RNA interference pathway can be exploited to cause a drastic decrease in the expression of a targeted gene.

Experimental Results

Construction of an RNAi Silencing Polynucleotide—The sequence of the cucumber homologous gene (SEQ ID NO:30) was determined from the ICuGI database and it showed 87.4% identity to the melon gene. The sequence of the homologous tomato gene (SEQ ID NO:31) was derived from the sgn [World Wide Web (dot) sgn] database and it showed a 70.6% identity to the melon gene.

The Melon and tomato LIVA-transporter genes (pH genes) were silenced via RNAi using the Hannibal vector. Amplicons of 524 bp long (melon) and 548 bp long (tomato) were produced via PCR on cDNA by adding two restriction sites to each primer. PCR using the forward and reverse primers from melon (SEQ ID NOs: 15 and 16) and tomatoes (SEQ ID NOs:17 and 18) generated amplicons (RNAi polynucleotides) which include the nucleic acid sequences set forth in SEQ ID NO:19 (for melon RNAi) and SEQ ID NO:20 (for tomatoes RNAi).

The amplicon was cut via restriction enzymes and ligated in the forward and reverse orientation interrupted by the vector's intron in a series of two ligations. The first restriction reaction was facilitated by XbaI and ClaI and the second one by XhoI and KpnI. The resulting construct (including 35-S and OCS terminator) was cut via the restriction enzymes SadI and SpeI and was ligated accordingly into pGreen. Agrobacterium mediated transformation was used to insert the melon and tomato constructs into Cucumber and Tomato, respectively.

The Effect of Silencing the Expression of the pH Gene in Cucumber and Tomato Fruit on Fruit Acidity—RNAi Transgenic tomatoes and melons were developed. Presence of the RNAi transgene was tested by using a PCR reaction of a primer from the pHannibal vector's intron (SEQ ID NO:22, Hannibal intron For), and the forward primer Tom Hannib F (SEQ ID NO:21). Transgenic plants were grown in a greenhouse under standard conditions. Ripe fruit was harvested approximately 50 days after anthesis, when tomato fruit were red-ripe and when cucumber fruit were ripe-yellow. pH was measured on juice extracted from fresh ripe fruit using a laboratory table top pH meter (Copenhagen radiometer).

As shown in Table 8, hereinbelow, while in control plants (devoid of the siRNA transgenic) the pH of the ripe fruits was 3.9 and 4.2 for cucumber and tomato, respectively, the pH of the ripe fruit of the siRNA transgenics was increased (i.e., less acidity) and reached an average level of 4.8 and 5.0 for cucumber and tomato, respectively.

TABLE 8

Table 8. Effect of silencing of the pH gene expression in cucumber and tomato fruit. N represents the number of ripe fruit analyzed. The data for the cucumber siRNA transgenics are from 3 independent transgenic lines. The data for the tomato siRNA transgenics are from 7 independent transgenic lines. From 1 to 4 fruit were analyzed per independent transformed line.

| | pH | |
|---|---|---|
| Species | Control, non-transgenic | siRNA transgenics |
| Ripe cucumber fruit (var. Ilan) | 3.9 ± 0.2 (n = 6) | 4.8 ± 0.2 (n = 10) |
| Ripe tomato fruit (var. MP-1) | 4.2 ± 0.08 (n = 8) | 5.0 ± 0.2 (n = 7) |

Example 8

Effect of Overexpression of the pH Gene from Tomato and from Sour Melon in Tomato Fruit Experimental Methods The sour melon and tomato LIVA-transporters (PH genes) were cloned (each) into the binary plasmid pGA using a PCR reaction that added the restriction sites XbaI and BglII to the following forward and reverse primers (respectively):

```
Mel-pGA For:
                                    (SEQ ID NO: 23)
TCT AGA ATG GAC ATG GAA AGA TTT CTC T;
and Mel-PGA Rev:
                                    (SEQ ID NO: 24)
AGA TCT GGG AAT TCG ATT TTA GAA GAG T;

Tom-pGA For:
                                    (SEQ ID NO: 25)
TCT AGA ATG GATAGG GTG TCG AGG AT;
and Tom-PGA Rev:
                                    (SEQ ID NO: 26)
AGA TCT GCG GGA ATT CGA TTT TAA AAG A.
```

The sour melon and tomato amplicons (including XbaI and BglII restriction sites) were 1,300 bp and 1,278 bp long, respectively. Agrobacterium mediated transformation was used to insert the tomato or melon gene into tomato MP line.

Experimental Results

As shown in Table 9, hereinbelow, overexpression of the pH tomato gene or the sour melon gene in tomato plants resulted in increased acidity (lower pH levels) as compared to wild type, non-transgenic tomato plants. These results conclusively show that the pH gene isolated and identified herein controls the acidity of plants, by reducing the pH levels (increased acidity) within the plant (e.g., in the fruits).

TABLE 9

Over-expression in tomatoes
pH levels in control or transgenic plants over-expressing the pH gene

| | |
|---|---|
| Tomato Control, non-transgenic | 4.2 ± 0.08 |
| Tomato line 51 (tomato gene) | 4.0 |
| Tomato line 32 (tomato gene) | 3.97 |
| Tomato line 34 (tomato gene) | 4.07 |
| Tomato line 45 (sour melon gene) | 3.9 |
| Tomato line 48 (sour melon gene) | 4.0 |

Table 9: Presented are the pH levels of fruit from control (non-transgenic wild type tomatoes), and from tomato lines which overexpress either the tomato pH gene or the sour melon pH gene. Data for control MP line tomatoes is the average of pH values from 8 fruit from 8 individual plants. pH values for the 5 transgenic tomato lines shown are a single pH measurement from a mix of blended juice of 2-5 mature fruit.

Example 9

Silencing of the pH Gene Affects Petal Color in Petunia

In order to test the role of the pH gene in determining petal color, the expression of the respective pH gene is reduced in plants of petunia using the technology of virus-induced gene silencing (VIGS), as described in (Spitzer et al. 2007, Plant Physiology 145:1241-1250, Reverse genetics of floral scent: application of tobacco rattle virus-based gene silencing in Petunia.). VIGs technology is a well-established technology of transiently silencing gene expression.

Construction of an VIGs Silencing Polynucleotide—A partial sequence of the petunia homologous gene (SEQ ID NO:36) was determined from the TIGR database and was found to exhibit 77.6% identity to the melon pH gene DNA sequence.

Petunia total RNA is extracted from a commercial variety of petunia, using peqGOLD TriFast TM (eqlab) and treated with RNase-free DNase (Fermentas). First strand cDNA is synthesized using 1 μg (microgram) total RNA, oligo d(T) primer, and Reverse Transcriptase AMV (Native) (eurX). PCR is performed for 40 cycles (94° C. for 15 minutes and then cycling at 94° C. for 10 seconds, 60° C. for 30 seconds, and 72° C. for 20 seconds) using Taq polymerase and the primers following PCR primers: 5'-CTGGGCTTAG-CATAGTTATGT-3' (SEQ ID NO:37) and 5'-TTGAGATA-GAGGGTGATCCAT-3' (SEQ ID NO:38) producing a 223-bp fragment petunia amplicon (SEQ ID NO:39). The Petunia amplicon is used as a template for an additional PCR amplification with the following VIGs pTRV2-destination primers, which are include the VIGs specific sequence (underlined sequence) as described in Liu 2002 [Liu., Schiff, M. and Dinesh-Kumar, S. P. (2002) Virus-induced gene silencing in tomato. Plant J. 31, 777-786]:

```
petunia VIGS For:
                                    (SEQ ID NO: 40)
5'-GGGGACAAGTTTGTACAAAAAAGCAGGCTCTGGGCTTAGCATAGTTA
TGT-3';
and petunia VIGS Rev:
                                    (SEQ ID NO: 41)
5'-GGGGACCACTTTGTACAAGAAAGCTGGGTTTGAGATAGAGGGTGATC
CAT-3'
```

The resulting PCR product with terminal attB1 and attB2 sequences is precipitated and incubated with the pDONR221 (Invitrogen, Carlsbad, Calif., USA) vector containing the attP1 and attP2 recombination sites and the BP CLONASE enzyme reaction (Invitrogen). To this construct, the pTRV2 destination vector containing the attR1 and attR2 recombination sites and the LR CLONASE enzyme is added. This mixture is transformed into DH10B chemical components cells and selected on kanamycin-containing LB plates. Clones are verified by restriction enzyme digestion and by sequencing the vector-insert junctions.

The Gateway vector is constructed, and transformed to Agrobacterium cells as described in Liu et al., 2002 (Supra). Petunia plantlets (Petunia hybrida) are grown as described by Spitzer et al., 2007 [Ben Spitzer, et al. Reverse Genetics of Floral Scent: Application of Tobacco Rattle Virus-Based Gene Silencing in Petunia. Plant Physiology 145:1241-1250, 2007], and Agro-infiltration is conducted on a 24 hour old flowers as described by Long et al. [Long, M. C., et al., 2009. Involvement of snapdragon benzaldehyde dehydrogenase in benzoic acid biosynthesis. Plant J. 59: 256-265].

The effect of silencing the expression of the pH gene petunia flowers—Petunia plants are grown and flower petal color is observed and compared to control non-infected plants. Without being bound by any theory, it is expected that the flower petal color of the VIGs infected plants will be of a bluer hue as compared to the control non-infected plants. A similar result was also shown in Verweij et al. (2008) [Verweij W, et al. 2008. An H+P-ATPase on the tonoplast determines vacuolar pH and flower color. Nat Cell Bio. 10: 1456-1462].

Analysis and Discussion

The LIVA duplication mutation causing a presumably dysfunctional proton transporter identified herein may have led to the evolution under domestication of the sweet dessert melons. Without being bound by any particular theory, it is assumed that the change in configuration may lead to a dysfunctional transporter and subsequently protons causing acidity not to be transported effectively, leading to a non-sour fruit. Fruits and vegetables such as tomato, apple, grape and cucumber (acidic fruit) have a higher acidity than sweet melons and a highly homologous gene encoding for a similar membrane transporter. The gene sequences of these acidic fruit encode for a protein lacking the duplication/mutation that characterizes the sweet melon and have, rather, a sequence of third transmembrane domain similar to the sour melon.

The mutation, or a similar mutation thereof, which modifies the function of the membrane transporter can be used for the development of fruit with modified acidity. In melons, the sequence of the gene can be used to develop molecular markers which can be used in the breeding of sweet melon with fruit of modified acidity.

In light of the function of the orthologous genes in other fruit, modifying the expression or the function of these orthologs in those fruit will also modify fruit acidity. Therefore, the modulation of this gene in other fruit by biotechnological means impacts the acidity of additional fruits as well.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of decreasing acidity of tomato, the method comprising transforming cells of the plant with a polynucleotide capable of downregulating expression level of a pH gene endogenous to the cells, said pH gene encoding a membrane transporter polypeptide as set forth in SEQ ID NO: 5, said pH gene being capable of modulating acidity of the plant, thereby decreasing the acidity of the plant.

2. A method of increasing acidity of a tomato plant, the method comprising transforming cells of the plant with a nucleic acid construct comprising a nucleic acid sequence encoding a polypeptide being at least 95% identical to a polypeptide set forth in SEQ ID NO:2 or 5, the polypeptide being a membrane transporter and capable of increasing acidity of the plant, thereby increasing the acidity of the plant.

3. The method of claim 2, wherein the polypeptide comprises a LIVA sequence in a non-duplicated manner.

4. The method of claim 2, wherein said nucleic acid sequence encodes a polypeptide as set forth in SEQ ID NO:2 or 5.

5. A method of decreasing acidity of melon, the method comprising transforming cells of a melon plant with a polynucleotide capable of downregulating expression level of a pH gene endogenous to the cells, said pH gene encoding a membrane transporter polypeptide as set forth in SEQ ID NO: 2, said pH gene being capable of modulating acidity of the plant, thereby decreasing the acidity of the plant.

6. A method of decreasing acidity of cucumber, the method comprising transforming cells of a cucumber plant with a polynucleotide capable of downregulating expression level of a pH gene endogenous to the cells, said pH gene encoding a membrane transporter polypeptide as set forth in SEQ ID NO: 6, said pH gene being capable of modulating acidity of the plant, thereby decreasing the acidity of the plant.

* * * * *